US009358398B2

(12) United States Patent
Moffitt et al.

(10) Patent No.: US 9,358,398 B2
(45) Date of Patent: Jun. 7, 2016

(54) COLLECTION OF CLINICAL DATA FOR GRAPHICAL REPRESENTATION AND ANALYSIS

(75) Inventors: Michael A. Moffitt, Valencia, CA (US); John J. Reinhold, Tarzana, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 84 days.

(21) Appl. No.: 13/481,497

(22) Filed: May 25, 2012

(65) Prior Publication Data
US 2012/0302912 A1 Nov. 29, 2012

Related U.S. Application Data

(60) Provisional application No. 61/491,092, filed on May 27, 2011.

(51) Int. Cl.
A61B 5/05 (2006.01)
A61N 1/372 (2006.01)
A61N 1/36 (2006.01)

(52) U.S. Cl.
CPC ........ *A61N 1/37235* (2013.01); *A61N 1/36185* (2013.01); *A61N 1/37241* (2013.01); *A61N 1/37247* (2013.01)

(58) Field of Classification Search
CPC ..... A61B 5/05; A61B 5/4893; A61N 1/36014
USPC .......................................... 600/554
See application file for complete search history.

(56) References Cited

U.S. PATENT DOCUMENTS

| 6,066,163 | A * | 5/2000 | John ........................ 607/45 |
| 6,516,227 | B1 | 2/2003 | Meadows et al. |
| 6,845,267 | B2 | 1/2005 | Harrison et al. |
| 6,895,280 | B2 | 5/2005 | Meadows et al. |
| 6,950,707 | B2 | 9/2005 | Whitehurst |
| 6,993,384 | B2 | 1/2006 | Bradley et al. |
| 7,650,184 | B2 | 1/2010 | Walter |
| 8,019,439 | B2 | 9/2011 | Kuzma et al. |
| 8,527,059 | B2 | 9/2013 | DeMulling et al. |
| 2004/0199218 | A1 | 10/2004 | Lee et al. |

(Continued)

OTHER PUBLICATIONS

PCT International Search Report for PCT/US2012/039709, Applicant: Boston Scientific Neuromodulation Corporation, Form PCT/ISA/210 and 220, dated Feb. 19, 2013 (13pages).

(Continued)

*Primary Examiner* — Sean Dougherty
*Assistant Examiner* — Daniel Cerioni
(74) *Attorney, Agent, or Firm* — Faegre Baker Daniels LLP

(57) ABSTRACT

A method of treating a patient and an external programmer for use with a neurostimulator. Electrical stimulation energy is serially conveyed into tissue of the patient via different combinations of electrodes implanted within the patient, thereby creating one or more clinical effects for each of the different electrode combinations. An influence of each of the different electrode combinations on the clinical effect(s) is determined. A graphical indication of the one or more clinical effects is generated based on the determined electrode combination influences. A graphical representation of the electrodes is displayed. The graphical indication of the clinical effect(s) is displayed adjacent the graphical electrode representation, such that a user can view an extent to which each of the different electrode combinations influences the clinical effect(s).

41 Claims, 29 Drawing Sheets

(56) References Cited

U.S. PATENT DOCUMENTS

| | | | |
|---|---|---|---|
| 2004/0215288 A1 | 10/2004 | Lee et al. | |
| 2005/0085743 A1* | 4/2005 | Hacker | A61B 5/04001 600/554 |
| 2006/0217781 A1* | 9/2006 | John | 607/45 |
| 2007/0129770 A1* | 6/2007 | Younis | 607/45 |
| 2007/0168004 A1 | 7/2007 | Walter | |
| 2007/0168007 A1 | 7/2007 | Kuzma et al. | |
| 2007/0203541 A1 | 8/2007 | Goetz et al. | |
| 2007/0203546 A1* | 8/2007 | Stone et al. | 607/59 |
| 2008/0004675 A1* | 1/2008 | King et al. | 607/59 |
| 2008/0100153 A1 | 5/2008 | Esenwein | |
| 2009/0259137 A1* | 10/2009 | Delic et al. | 600/545 |
| 2010/0010566 A1 | 1/2010 | Thacker et al. | |
| 2010/0100153 A1 | 4/2010 | Carlson et al. | |
| 2010/0121409 A1 | 5/2010 | Kothandaraman et al. | |
| 2011/0106215 A1 | 5/2011 | Moffitt | |
| 2012/0046715 A1 | 2/2012 | Moffitt et al. | |

OTHER PUBLICATIONS

PCT Written Opinion of the International Search Authority for PCT/US2012/039709, Applicant: Boston Scientific Neuromodulation Corporation, Form PCT/ISA/237, dated Feb. 19, 2013 (11pages).
File History of U.S. Appl. No. 13/481,524, entitled: Collection of Clinical Data for Graphical Representation and Analysis, filed May 25, 2012, inventor: Michael A. Moffitt et al.
Communication Relating to the Results of the Partial International Search for PCT/US2012/039709, Applicant: Boston Scientific Neuromodulation Corporation, Form PCT/ISA/206, dated Oct. 1, 2012 (6pages).
U.S. Appl. No. 61/374,879, Title: User Interface for Segmented Neurostimulation Leads, Inventor: Michael A. Moffitt et al., filed Aug. 18, 2010.
Frankemolle, Anneke M.M. et al., Reversing cognitive-motor impairments in Parkinson's disease patients using a computational modelling approach to deep brain stimulation programming, Brain 2010:133;746-761.
Hunka, Karen et al., Nursing Time to Program and Assess Deep Brain Stimulators in Movement Disorder Patients, J. Neurosci Nurs. 37:4; 204-210 (Aug. 2005).
File History of U.S. Appl. No. 13/481,497, entitled: Collection of Clinical Data for Graphical Representation and Analysis, filed May 25, 2012, inventor: Michael A. Moffitt et al.
Final Office Action dated Mar. 13,2014 in U.S. Appl. No. 13/481,497, filed May 25, 2012, inventor: Michael A. Moffitt, (20 pages).
Office Action dated Jan. 2, 2014 in U.S. Appl. No. 13/481,497, filed May 25, 2012, inventor: Michael A. Moffitt, (25 pages).
PCT International Preliminary Report on Patentability (Chapter I of the Patent Cooperation Treaty) for PCT/US2012/039709, Applicant: Boston Scientific Neuromodulation Corporation, Form PCT/IB/326 and 373, dated Dec. 12, 2013 (13 pages).

* cited by examiner

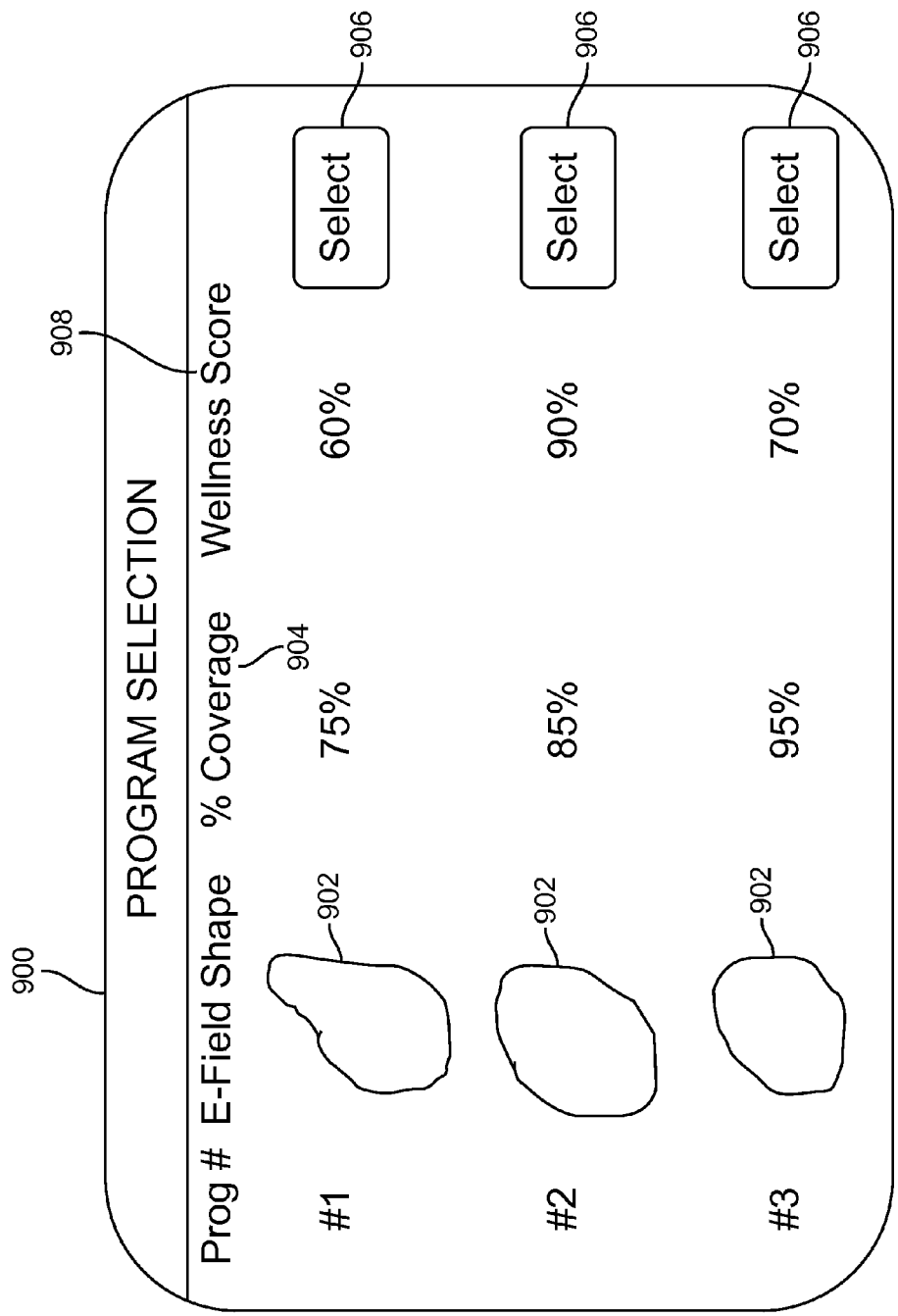

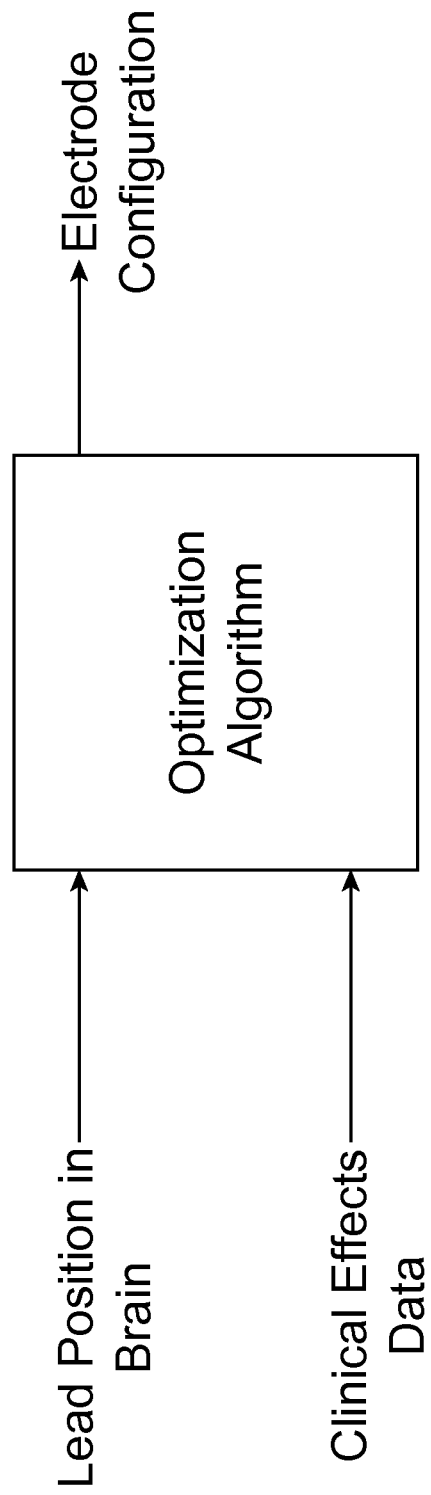

COLLECTION OF CLINICAL DATA FOR GRAPHICAL REPRESENTATION AND ANALYSIS

RELATED APPLICATION DATA

The present application claims the benefit under 35 U.S.C. §119 to U.S. provisional patent application Ser. No. 61/491,092, filed May 27, 2011. The foregoing application is hereby incorporated by reference into the present application in its entirety.

FIELD OF THE INVENTION

The present invention relates to tissue stimulation systems, and more particularly, to user interfaces and methods for controlling the distribution of electrical current on neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Further, in recent investigations, Peripheral Nerve Stimulation (PNS) systems have demonstrated efficacy in the treatment of chronic pain syndromes and incontinence, and a number of additional applications are currently under investigation.

More pertinent to the present inventions described herein, Deep Brain Stimulation (DBS) has been applied therapeutically for well over a decade for the treatment of neurological disorders, including Parkinson's Disease, essential tremor, dystonia, and epilepsy, to name but a few. Further details discussing the treatment of diseases using DBS are disclosed in U.S. Pat. Nos. 6,845,267, 6,845,267, and 6,950,707, which are expressly incorporated herein by reference.

Each of these implantable neurostimulation systems typically includes one or more electrode carrying stimulation leads, which are implanted at the desired stimulation site, and a neurostimulator implanted remotely from the stimulation site, but coupled either directly to the neurostimulation lead(s) or indirectly to the neurostimulation lead(s) via a lead extension. The neurostimulation system may further comprise a handheld external control device to remotely instruct the neurostimulator to generate electrical stimulation pulses in accordance with selected stimulation parameters. Typically, the stimulation parameters programmed into the neurostimulator can be adjusted by manipulating controls on the external control device to modify the electrical stimulation provided by the neurostimulator system to the patient.

Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated (the target tissue region) in order to provide the therapeutic benefit (e.g., treatment of movement disorders), while minimizing the non-target tissue region that is stimulated. A typical stimulation parameter set may include the electrodes that are acting as anodes or cathodes, as well as the amplitude, duration, and rate of the stimulation pulses.

Significantly, non-optimal electrode placement and stimulation parameter selections may result in excessive energy consumption due to stimulation that is set at too high an amplitude, too wide a pulse duration, or too fast a frequency; inadequate or marginalized treatment due to stimulation that is set at too low an amplitude, too narrow a pulse duration, or too slow a frequency; or stimulation of neighboring cell populations that may result in undesirable side-effects.

For example, bilateral DBS of the subthalamic nucleus has been proven to provide effective therapy for improving the major motor signs of advanced Parkinson's disease, and although the bilateral stimulation of the subthalamic nucleus is considered safe, an emerging concern is the potential negative consequences that it may have on cognitive functioning and overall quality of life (see A. M. M. Frankemolle, et al., *Reversing Cognitive-Motor Impairments in Parkinson's Disease Patients Using a Computational Modelling Approach to Deep Brain Stimulation Programming*, Brain 2010; pp. 1-16). In large part, this phenomenon is due to the small size of the subthalamic nucleus, which may range from the size of a pea to the size of a peanut, with varying shapes from spherical to kidney-shape. Even with the electrodes are located predominately within the sensorimotor territory, the electric field generated by DBS is non-discriminately applied to all neural elements surrounding the electrodes, thereby resulting in the spread of current to neural elements affecting cognition. As a result, diminished cognitive function during stimulation of the subthalamic nucleus may occur do to non-selective activation of non-motor pathways within or around the subthalamic nucleus.

Thus, it is crucial that proper location and maintenance of the lead position be accomplished in order to continuously achieve efficacious therapy. Lead displacements of less than a millimeter may have a deleterious effect on the patient's therapy. Because the stimulation region needs to be in the correct location to achieve optimal therapy and minimization of side-effects, stimulation leads typically carry many electrodes (e.g., four), so that at least one of the electrodes is near the target and allow programming of the electrodes to place the stimulation field in that region of interest.

The large number of electrodes available, combined with the ability to generate a variety of complex stimulation pulses, presents a huge selection of stimulation parameter sets to the clinician or patient. In the context of DBS, neurostimulation leads with a complex arrangement of electrodes that not only are distributed axially along the leads, but are also distributed circumferentially around the neurostimulation leads as segmented electrodes, can be used.

To facilitate such selection, the clinician generally programs the external control device, and if applicable the neurostimulator, through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback and to subsequently program the external control device with the optimum stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. Once the leads are correctly positioned, a fitting procedure, which may be referred to as a navigation session, may be performed using the computerized programming system to program the external control device, and if applicable the neurostimulator, with a set of stimulation parameters that best addresses the neurological disorder(s).

As physicians and clinicians become more comfortable with implanting neurostimulation systems and time in the operating room decreases, post-implant programming sessions are becoming a larger portion of process. Furthermore, because the body tends to adapt to the specific stimulation parameters currently programmed into a neurostimulation system, or the full effects of stimulation are not manifest in a short period of time (i.e., not observed within a programming session), follow-up programming procedures are often needed.

For example, in the context of DBS, the brain is dynamic (e.g., due to disease progression, motor re-learning, or other changes), and a program (i.e., a set of stimulation parameters) that is useful for a period of time may not maintain its effectiveness and/or the expectations of the patient may increase. Further, physicians typically treat the patient with stimulation and medication, and proper amounts of each are required for optimal therapy. Thus, after the DBS system has been implanted and fitted, the patient may have to schedule another visit to the physician in order to adjust the stimulation parameters of the DBS system if the treatment provided by the implanted DBS system is no longer effective or otherwise is not therapeutically or operationally optimum due to, e.g., disease progression, motor re-learning, or other changes.

Regardless of the skill of the physician or clinician, neurostimulation programming sessions can be especially lengthy when programming complicated neurostimulation systems, such as DBS systems, where patients usually cannot feel the effects of stimulation, and the effects of the stimulation may be difficult to observe, are typically subjective, or otherwise may take a long time to become apparent. Clinical estimates suggest that 18-36 hours per patient are necessary to program and assess DBS patients with current techniques (see Hunka K., et al., *Nursing Time to Program and Assess Deep Brain Stimulators in Movement Disorder Patients*, J. Neursci Nurs. 37: 204-10), which is an extremely large time commitment for both the physician/clinician and the patient.

Significantly contributing to the lengthy process of programming neurostimulation system is the fact the location of the electrodes relative to the target tissue region is not exactly known when the neurostimulation lead or leads are initially implanted within the brain of the patient. In a typical programming session, the boundaries of a targeted region or structure relative to the electrodes can be determined by observing and recording a substantial amount of clinical information observed during the programming session of each patient is recorded. Typically this is accomplished by incrementally increasing the amplitude of electrical stimulation energy on each individual electrode one at a time, for each amplitude increment, observing and manually recording on a relatively large paper spread sheet, clinical information, such as the types of therapeutic effects and side-effects, the threshold values of these therapeutic effects and side-effects, the extent of these therapeutic effects and side-effects. Based on this observed information, the physician or clinician may determine the electrodes having the greatest influence on the surrounding tissue, whether such influence causes a therapeutic effect or a side-effect, the neurostimulation system can be programmed with the best stimulation parameter sets (i.e., those that maximize the volume of target tissue, while minimizing the volume of non-target tissue).

Notably, as the stimulation level of the electrodes that within the targeted region is incrementally increased, first a therapeutic level is reached, and then unwanted side-effects are reached. The boundaries of the target tissue region are determined to be around the therapeutic level, but below the side-effects level. The electrodes located outside of the target tissue region (in theory) have not therapeutic level, only a side-effect level. Once the boundaries the target tissue region are determined, the neurostimulation system can be programmed, such that the resulting electrical stimulation field covers the target tissue region (i.e., the shape and size of the electrical stimulation matches the shape and size of the target tissue region).

While the manual recording of this clinical information has some utility in facilitating programming sessions, the recorded clinical information is not represented to the physician or clinician in a manner that the physician or clinician can readily taken advantage of in the current programming session, and certainly during subsequent programming sessions where the same physician or clinician will not have access to this recorded clinical information.

To facilitate determination of the location of the electrodes relative to the target tissue region or regions, and even the non-target tissue region or regions, a computerized programming system may optionally be capable of storing one or more anatomical regions of interest, which may be registered within the neurostimulation leads when implanted with the patient.

The anatomical region of interest may be a target tissue region, the stimulation of which is known or believed to provide the needed therapy to the patient. For example, if the DBS indication is Parkinson's disease, the target tissue region may be the subthalamic nucleus (STN) or the globus pallidus (GPi). If the DBS indication is Essential Tremor, the target tissue region may be the thalamus. If the DBS indication is depression, the target tissue region may be one or more of the nucleus acumbens, ventral striatum, ventral capsule, anterior capsule, or the Brodmann's area 25. If the DBS indication is epilepsy, the target tissue region may be preferably the anterior nucleus. If the DBS indication is a gait disorder, the target tissue region may be the pedunculopontine nucleus (PPN). If the DBS indication is dementia, Alzheimer's disease or memory disorders, the target tissue region may be anywhere in the Papez circuit.

The anatomical region of interest may be a non-target tissue region, the stimulation of which is known or believed to provide an undesirable side-effect for the patient. For example, stimulation of medial to the STN may cause eye deviations, and stimulation of the substantia nigra may cause symptoms of depression.

Notably, the anatomical region of interest may not be strictly anatomical, but rather may simply represent some arbitrary volume of tissue that, when stimulated, provides therapy or creates a side-effect. The anatomical region of interest may be naturally defined (e.g., an anatomical structure corresponding to the target tissue volume may naturally provide the boundaries that delineate it from the surrounding tissue) or may be defined by a graphical marking). The anatomical region of interest may be obtained from a generally available atlas, and in the case of DBS, a brain atlas, which may be derived from the general population or a previous patient, or may be obtained from a patient specific atlas derived from, e.g., a magnetic resonant imager (MRI), computed tomography (CT), X-ray, fluoroscopy, ventriculography, ultrasound, or any other imaging modality or a merging of any or all of these modalities.

Although the use of a generalized atlas may be quite helpful when optimizing the stimulation parameters that are ultimately programmed into the neurostimulation system, these types of atlases are not patient specific, and thus, cannot account for patient specific physiology. Even if a patient-specific atlas is used, any errors in registration with the neurostimulation leads may prevent optimized programming of the neurostimulation system.

There, thus, remains a need for a user interface that more efficiently allows the programming of neurostimulation systems.

SUMMARY OF THE INVENTION

In accordance with a first aspect of the present inventions, a method of treating a patient is provided. The method comprises serially conveying electrical stimulation energy into tissue (e.g., brain tissue) of the patient via different combinations of electrodes implanted within the patient, thereby creating one or more clinical effects (e.g., a therapeutic effect and/or a side-effect) for each of the different electrode combinations. In one embodiment, each electrode combination has only one electrode. In another embodiment, at least one of the electrode combinations comprises a fractionalized electrode combination.

The method further comprises determining an influence of each of the different electrode combinations on the clinical effect(s), and generating a graphical indication of the clinical effect(s) based on the determined electrode combination influences. The method further comprises displaying a graphical representation of the electrodes, and displaying the graphical indication of the clinical effect(s) adjacent the graphical electrode representation, such that a user can determine an extent to which each of the different electrode combinations influences the clinical effect(s). The electrical stimulation energy may be conveyed from a neurostimulator, in which case, the method may further comprise programming the neurostimulator based on the determined extent to which the each different electrode combination influences the clinical effects(s). The method may further comprise recording data in computer memory indicating the determined influence of the each different electrode combination on the clinical effect(s).

One method further comprises incrementally increasing an intensity level of the conveyed electrical stimulation energy for each of the different electrode combinations, wherein the influence of the each different electrode combination on the clinical effect(s) is determined for each of the incremental intensity levels. In this case, the clinical effect(s) may include one or more therapeutic effects, and the influence of the each different electrode combination on the therapeutic effect(s) may be determined by determining the range of incremental intensity levels at which a metric of the therapeutic effect(s) (e.g., a perception threshold of the therapeutic effect(s)) occurs.

In this method, the clinical effect(s) may further comprise one or more side-effects, and the influence of the each different electrode combination on the side-effect(s) may be determined by determining the incremental intensity level at which a metric of the side-effect(s) (e.g., a perception threshold of the side-effect(s), an uncomfortable threshold of the side-effect(s), or an intolerable threshold of the side-effect(s)) initially occurs. In this case, the influence of the each different electrode combination on the therapeutic effect(s) may further be determined by determining the highest intensity level at which the therapeutic effect metric(s) occur prior to the initial occurrence of the side-effect metric(s). The graphical indication of the clinical effect(s) may comprise a bar map having a plurality of bars, each of which indicates for the each different electrode combination the highest intensity level at which the therapeutic effect metric(s) occur prior to the initial occurrence of the side-effect metric(s).

In this method, the therapeutic effect metric may alternatively be a relative level of the therapeutic effect(s), in which case, the graphical indication of the clinical effect(s) may comprise a bar map for each of the electrode combinations, each bar map having a bar indicating the relative level of the therapeutic effect(s) at the each incremental intensity level. The therapeutic effect(s) may comprise a plurality of therapeutic effects, and the relative level may be a composite score as a function of individual scores of the therapeutic effects.

In this method, the influence of the each different electrode combination on the clinical effect(s) may alternatively be determined by determining the electrode combinations that most influence the therapeutic effect(s), and wherein the graphical indication of the clinical effect(s) comprises at least one target tissue region displayed adjacent the electrode combinations in the graphical electrode representation determined to most influence the therapeutic effect(s). In this case, the influence of the each different electrode combination on the clinical effect(s) may be determined by determining the electrode combinations that most influence the side-effect, and the graphical indication of the clinical effect(s) may comprise at least one non-target tissue region displayed adjacent the electrode combinations in the graphical electrode representation determined to most influence the side-effect. Optionally, this method may further comprise estimating one of an electric field or a region of tissue activation at the highest incremental intensity level at which the therapeutic effect(s) occurs for the each different electrode combination, in which case, the target tissue region may be based on the estimated electric field or region of tissue activation.

In accordance with a second aspect of the present inventions, an external programmer for use with a neurostimulator is provided. The neurostimulator comprises output circuitry configured for communicating with the neurostimulator, and control circuitry configured for instructing the neurostimulator via the output circuitry to serially convey electrical stimulation energy into tissue of a patient via different combinations of electrodes implanted within the patient, thereby creating one or more clinical effects (e.g., a therapeutic effect and/or a side-effect) for each of the different electrode combinations. In one embodiment, each electrode combination has only one electrode. In another embodiment, at least one of the electrode combinations comprises a fractionalized electrode combination.

The neurostimulator further comprises processing circuitry configured for determining an influence of each of the different electrode combinations on the clinical effect(s), and generating a graphical indication of the clinical effect(s) based on the determined electrode combination influences. The control circuitry is further configured for instructing a display device to display the graphical indication of the clinical effect(s) adjacent a graphical representation of the electrodes, such that the user can determine an extent to which each of the different electrode combinations influences the clinical effect(s). The control circuitry may further be configured for programming the neurostimulator via the output circuitry based on the determined extent to which the each different electrode combination influences the clinical effect(s).

The external programmer may further comprise a user interface configured for allowing a user to enter clinical information on the clinical effect(s) for each different electrode combination, in which case, the processing circuitry may be configured for determining the influence of the each different electrode combination on the clinical effect(s) based on the clinical information entered by the user. The processing circuitry may determine the influence of each of the different electrode combinations on the clinical effect(s) by, e.g., deriving such influence from the clinical information entered by the user, or if the clinical information entered by the user is, itself, an influence of each of the different electrode combinations on the clinical effect(s), by merely accepting the clinical information as such influence. The external programmer may further comprise monitoring circuitry configured for monitoring the clinical effect(s) for each different electrode combination, in which case, the processing circuitry may be configured for determining the influence of the each different electrode combination on the clinical effect(s) based on the monitored clinical effect(s). The external programmer may further comprise memory configured for storing data indicating the determined influence of the each different electrode combination on the clinical effect(s).

In one embodiment, control circuitry is further configured for instructing the neurostimulator via the output circuitry to incrementally increase an intensity level of the conveyed electrical stimulation energy for each of the different electrode combinations, and the processing circuitry is configured for determining the influence of the each different electrode combination on the clinical effect(s) for each of the incremental intensity levels. In this case, the clinical effect(s) may comprise one or more therapeutic effects, and the processing circuitry may be configured for determining the influence of the each different electrode combination on the therapeutic effect(s) by determining the range of incremental intensity levels at which a metric of the therapeutic effect(s) (e.g., a perception threshold of the therapeutic effect(s)) occurs.

In this embodiment, the clinical effect(s) may further comprises one or more side-effects, in which case, the processing circuitry may be further configured for determining the influence of the each different electrode combination on the side-effect(s) by determining the incremental intensity level at which a metric of the side-effect(s) (e.g., a perception threshold of the one or more side-effects, an uncomfortable threshold of the one or more side-effects, or an intolerable threshold of the one or more side-effects) initially occurs. The processing circuitry may be further configured for determining the influence of the each different electrode combination on the therapeutic effect(s) by determining the highest intensity level at which the therapeutic effect metric(s) occur prior to the initial occurrence of the side-effect metric(s). The graphical indication of the clinical effect(s) may comprise a bar map having a plurality of bars, each of which indicates for the each different electrode combination the highest intensity level at which the therapeutic effect metric(s) occur prior to the initial occurrence of the side-effect metric(s).

In this embodiment, the therapeutic effect metric may alternatively be a relative level of the one or more therapeutic effects, in which case, the graphical indication of the clinical effect(s) may comprises a bar map for each of the electrode combinations, each bar map having a bar indicating the relative level of the therapeutic effect(s) at each incremental intensity level. The therapeutic effect(s) may comprises a plurality of therapeutic effects, and the relative level ma be composite score as a function of individual scores of the therapeutic effects.

In this embodiment, the processing circuitry may alternatively be configured for determining the influence of the each different electrode combination on the clinical effect(s) by determining the electrode combinations that most influence the therapeutic effect(s), and the graphical indication of the clinical effect(s) may comprise at least one target tissue region displayed adjacent the electrode combinations in the graphical electrode representation determined to most influence the therapeutic effect(s). The processing circuitry may further be configured for determining the influence of the each different electrode combination on the clinical effect(s) by determining the electrode combinations that most influence the side-effect, in which case, the graphical indication of the clinical effect(s) may comprise at least one non-target tissue region displayed adjacent the electrode combinations in the graphical electrode representation determined to most influence the side-effect. The processing circuitry may further be configured for estimating one of an electric field or a region of tissue activation at the highest incremental intensity level at which the therapeutic effect(s) occurs for the each different electrode combination, wherein the target tissue region is based on the estimated electric field or region of tissue activation.

In accordance with a third aspect of the present inventions, a method of treating a patient is provided. The method comprises conveying electrical stimulation energy into tissue (e.g., brain tissue) of the patient via a specified combination of a plurality of electrodes, thereby creating one or more clinical effects, and determining an influence of the specified electrode combination on the clinical effect(s). The method further comprises displaying an anatomical region of interest in registration with a graphical representation of the plurality of electrodes. The anatomical region of interest may be, e.g., an anatomical structure functionally delineated from surrounding tissue or an arbitrarily defined anatomical region of interest. The anatomical region of interest may be a therapy tissue region or a side-effect tissue region.

The method further comprises modifying the displayed anatomical region of interest based on the determined influence of the specified electrode combination on the clinical effect(s). The displayed anatomical region of interest may be modified by, e.g., spatially translating the displayed anatomical region of interest relative to the graphical electrode representation or changing the shape of the displayed anatomical region of interest. The electrical stimulation energy may be conveyed from a neurostimulator, in which case, the method may further comprise programming the neurostimulator based on the modified anatomical region of interest. The method may further comprise recording the modified anatomical region of interest in computer memory.

One method further comprises determining a displayed proximity between the displayed anatomical region of interest and the specified electrode combination in the graphical electrode representation, and implying an actual proximity between the anatomical region of interest and the specified electrode combination based on the determined influence of the specified electrode combination on the clinical effect(s). In this case, the displayed anatomical region of interest may be modified by spatially translating the displayed anatomical region of interest relative to the specified electrode combination in the graphical electrode representation to better match the displayed proximity to the actual proximity. If the displayed proximity is greater than the actual proximity, the displayed anatomical region of interest may be spatially translated closer to the specified electrode combination in the graphical electrode representation. If the displayed proximity is less than the actual proximity, the displayed anatomical region of interest may be spatially translated further from the specified electrode combination in the graphical electrode representation.

Another method further comprises displaying another anatomical region of interest in registration with a graphical representation of the plurality of electrodes, in which case, the clinical effect(s) comprise a therapeutic effect and a side-effect, the anatomical region of interest is a therapy tissue region, and the other anatomical region of interest is a side-effect tissue region. The influence of the specified electrode combination on the clinical effect(s) can be determined by determining a relative influence of the specified electrode combination on the therapeutic effect and the side-effect, and the displayed therapy tissue region and displayed side-effect tissue region may be modified by spatially translating the displayed therapy tissue region and the side-effect tissue region relative to the specified electrode combination in the graphical electrode representation based on the determined relative influence of the specified electrode combination on the therapeutic effect and the side-effect.

For example, if the specified electrode combination in the graphical electrode representation is closer to the displayed therapy tissue region than the displayed side-effect tissue region, the displayed therapy tissue region may be spatially translated further from the specified electrode combination in the graphical electrode representation and the displayed side-effect tissue region may be spatially translated closer to the specified electrode combination in the graphical electrode representation if the specified electrode combination is determined to influence the side-effect more than the therapeutic effect.

As another example, if the specified electrode combination in the graphical electrode representation is closer to the displayed side-effect tissue region than the displayed therapy tissue region, the displayed therapy tissue region may be spatially translated closer to the specified electrode combination in the graphical electrode representation and the displayed side-effect tissue region is spatially translated further from the specified electrode combination in the graphical electrode representation if the specified electrode combination is determined to influence the therapeutic effect more than the side-effect.

Still another method further comprises serially conveying electrical stimulation energy into the tissue of the patient via first and second combinations of the electrodes, thereby creating the clinical effect(s), with the first electrode combination in the graphical electrode representation being further away from the displayed anatomical region of interest than the second electrode combination in the graphical electrode representation. The method further comprises determining an influence of each of the first and second electrode combinations on the clinical effect(s), wherein the first electrode combination is determined to have a higher influence on the clinical effect(s) than the second electrode combination. The displayed anatomical region of interest may then be modified by spatially translating the displayed anatomical region of interest away from the second electrode combination in the graphical electrode representation towards the first electrode combination in the graphical electrode representation.

Yet another method further comprises serially conveying electrical stimulation energy into tissue of the patient via different combinations of electrodes implanted within the patient, thereby creating one or more clinical effects for each of the different electrode combinations. The clinical effect(s) comprises one or more therapeutic effects and one or more side-effects, and the displayed anatomical region is a therapy tissue region. The method further comprises incrementally increasing an intensity level of the conveyed electrical stimulation energy for each of the different electrode combinations, determining the influence of each different electrode combination on the clinical effect(s) by determining the highest intensity level at which a metric of the therapeutic effect(s) occurs prior to an initial occurrence of a metric of the side-effect(s). The displayed therapy tissue region may be modified by changing the shape of the therapy tissue region based on the determined highest intensity levels for the specified electrode combinations.

In accordance with a fourth aspect of the present inventions, an external programmer for use with a neurostimulator is provided. The external programmer comprises output circuitry configured for communicating with the neurostimulator, and control circuitry configured for instructing the neurostimulator via the output circuitry to convey electrical stimulation energy into the tissue of the patient via a specified combination of a plurality of electrodes, thereby creating one or more clinical effects, and for instructing a display device to display an anatomical region of interest in registration with a graphical representation of a plurality of electrodes. The anatomical region of interest may be, e.g., an anatomical structure functionally delineated from surrounding tissue or an arbitrarily defined anatomical region of interest. The anatomical region of interest may be a therapy tissue region or a side-effect tissue region.

The external programmer further comprises processing circuitry configured for determining an influence of the specified electrode combination on the clinical effect(s). The processing circuitry may determine the influence of each of the different electrode combinations on the clinical effect(s) by, e.g., deriving such influence from clinical information entered by the user, or if the clinical information entered by the user is, itself, an influence of each of the different electrode combinations on the clinical effect(s), by merely accepting the clinical information as such influence. The processing circuitry is further configured for modifying the anatomical region of interest based on the determined influence of the specified electrode combination on the clinical effect(s). The displayed anatomical region of interest may be modified by, e.g., spatially translating the displayed anatomical region of interest relative to the graphical electrode representation or changing the shape of the displayed anatomical region of interest. The control circuitry may be further configured for programming the neurostimulator via the output circuitry based on the modified anatomical region of interest. The external programmer may further comprise memory configured for storing the modified anatomical region of interest.

In one embodiment, the processing circuitry is further configured for determining a displayed proximity between the displayed anatomical region of interest and the specified electrode combination in the graphical electrode representation, implying an actual proximity between the anatomical region of interest and the specified electrode combination based on the determined influence of the specified electrode combination on the clinical effect(s), and modifying the displayed anatomical region of interest by spatially translating the displayed anatomical region of interest relative to the specified electrode combination in the graphical electrode representation to better match the displayed proximity to the actual proximity. The processing circuitry may be configured for spatially translating the displayed anatomical region of interest closer to the specified electrode combination in the graphical electrode representation if the displayed proximity is greater than the actual proximity. The processing circuitry may be configured for spatially translating the displayed anatomical region of interest further from the specified electrode combination in the graphical electrode representation if the displayed proximity is less than the actual proximity.

In another embodiment, the control circuitry is further configured for instructing the display device to display another anatomical region of interest in registration with a graphical representation of a plurality of electrodes. In this case, the clinical effect(s) may comprise a therapeutic effect and a side-effect, the anatomical region of interest may be a therapy tissue region, the other anatomical region of interest may be a side-effect tissue region. The processing circuitry is configured for determining the influence electrode combination on the clinical effect(s) by determining a relative influence of the specified electrode combination on the therapeutic effect and the side-effect, and modifying the displayed therapy tissue region and displayed side-effect tissue region by spatially translating the displayed therapy tissue region and the side-effect tissue region relative to the specified electrode combination in the graphical electrode representation based on the determined relative influence of the specified electrode combination on the therapeutic effect and the side-effect.

In one example, if the specified electrode combination in the graphical electrode representation is closer to the displayed therapy tissue region than the displayed side-effect tissue region, the processing circuitry may be configured for spatially translating the displayed therapy tissue region further from the specified electrode combination in the graphical electrode representation and the displayed side-effect tissue region closer to the specified electrode combination in the graphical electrode representation if the specified electrode combination is determined to influence the side-effect more than the therapeutic effect.

In another example, if the specified electrode combination in the graphical electrode representation is closer to the displayed side-effect tissue region than the displayed therapy tissue region, the processing circuitry may be configured for spatially translating the displayed therapy tissue region closer to the specified electrode combination in the graphical electrode representation and the displayed side-effect tissue region further from the specified electrode combination in the graphical electrode representation if the specified electrode combination is determined to influence the therapeutic effect more than the side-effect.

In still another embodiment, the control circuitry is configured for serially conveying electrical stimulation energy into the tissue of the patient via first and second combinations of the electrodes, thereby creating the clinical effect(s), with the first electrode combination in the graphical electrode representation being further away from the displayed anatomical region of interest than the second electrode combination in the graphical electrode representation. The processing circuitry is configured for determining an influence of each of the first and second electrode combinations on the clinical effect(s). If the first electrode combinations is determined to have a higher influence on the clinical effect(s) than the second electrode combination, the processing circuitry may be further configured for modifying the displayed anatomical region of interest by spatially translating the displayed anatomical region of interest away from the second electrode combination in the graphical electrode representation towards the first electrode combination in the graphical electrode representation.

In yet another embodiment, the control circuitry is configured for serially conveying electrical stimulation energy into tissue of the patient via different combinations of electrodes implanted within the patient, thereby creating one or more clinical effects for each of the different electrode combinations. In this case, the clinical effect(s) comprises one or more therapeutic effects and one or more side-effects, and the displayed anatomical region is a therapy tissue region. The control circuitry is further configured for incrementally increasing an intensity level of the conveyed electrical stimulation energy for each of the different electrode combinations. The processing circuitry is configured for determining the influence of the each different electrode combination on the one or more clinical effects by determining the highest intensity level at which a metric of the therapeutic effect(s) occurs prior to an initial occurrence of a metric of the side-effect(s), and modifying the displayed therapy tissue region by changing the shape of the therapy tissue region based on the determined highest intensity levels for respective the specified electrode combinations.

In accordance with a fifth aspect of the present inventions, a method of treating a patient using a plurality of electrodes implanted within tissue (e.g., brain tissue) of the patient is provided. The method comprises selecting one of a plurality of different pre-defined shapes (e.g., a circular shape and a pear-shape) for an electric field, and defining a location of the electric field relative to a graphical representation of the electrodes. The method further comprises determining a combination of the electrodes (which may be fractionalized) based on the one selected shape and defined location of the electric field, and conveying electrical stimulation energy into the tissue of the patient via the determined electrode combination. In one method, the electrical stimulation energy is conveyed from a neurostimulator, in which case, the method may further comprise programming the neurostimulator to convey the electrical stimulation energy via the automatically determined electrode combination.

An optional method further comprises selecting another one of the plurality of different pre-defined shapes for another electric field, and defining a location of the other electric field relative to the graphical representation of the electrodes. In this case, the combination of the electrodes are determined based on both the one selected shape and defined location of the electric field and the other selected shape and defined location of the other electric field. Another optional method further comprises adjusting an intensity level of the conveyed electrical stimulation energy, wherein a size of the displayed electric field is adjusted in accordance with the adjusted intensity level.

A representation of the electric field may be displayed relative to the graphical electrode representation. In this case, the method may further comprise displaying a therapy tissue region, and comparing the displayed therapy tissue region to the plurality of different pre-defined electric field shapes, wherein the one pre-defined shape is selected based on the comparison. For example, the pre-defined shape that best matches the displayed therapy tissue region may be selected as the one pre-defined shape. In another method, the therapy tissue region is displayed relative to the graphical electrode representation, and the defined location of the electric field is defined to match the location of the displayed therapy tissue region relative to the graphical electrode representation.

In one method, the specified electrode combination is automatically determined based on the selected pre-defined shape and the defined location of the electric field. In this case, the method may further comprise automatically determining a plurality of different combinations of the electrodes based on the selected pre-defined shape and the defined location of the electric field, and serially conveying electrical stimulation energy into the tissue of the patient via the plurality of determined electrode combinations, thereby creating a clinical effect for each of the determined electrode combinations. The method may further comprise assigning a score to each of the determined electrode combinations based on the respective clinical effect, and selecting one of the determined electrode combinations based on the assigned scores.

In accordance with a sixth aspect of the present inventions, an external programmer for use with a neurostimulator is provided. The external programmer comprises memory storing a plurality of different pre-defined shapes (e.g., a circular shape and a pear-shape) for an electric field, and a user interface configured for allowing a user to select one of the pre-defined shapes, and for allowing the user to define a location of the electric field relative to a graphical representation of the electrodes. The external programmer further comprises output circuitry configured for communicating with the neurostimulator, processing circuitry configured for determining a combination of the electrodes (which may be fractionalized) based on the one selected shape and defined location of the electric field, and control circuitry configured for instructing the neurostimulator via the output circuitry to convey electrical stimulation energy into the tissue of the patient via the determined electrode combination. The control circuitry may be further configured for programming the neurostimulator with the determined electrode combination.

In one optional embodiment, the user interface is further configured for allowing a user to select another one of the plurality of different pre-defined shapes for another electric field, and allowing the user to define a location of the other electric field relative to the graphical representation of the electrodes. In this case, the processing circuitry may be configured for determining the combination of the electrodes based on both the one selected shape and defined location of the electric field and the other selected shape and defined location of the other electric field. In another optional embodiment, the control circuitry is further configured for adjusting an intensity level of the conveyed electrical stimulation energy, wherein a size of the displayed electric field is adjusted in accordance with the adjusted intensity level.

The control circuitry may further be configured for instructing a display device to display a representation of the electric field relative to the graphical electrode representation. In this case, the control circuitry may be configured for displaying a therapy tissue region to a user, and the user interface may be configured for allowing a user to compare the displayed therapy tissue region to the plurality of different pre-defined electric field shapes, such that the user may select the one pre-defined shape based on the comparison. In another embodiment, the control circuitry may be configured for displaying the therapy tissue region is displayed relative to the graphical electrode representation, and the user interface may be configured for allowing the user to define the location of the electric field to match the location of the displayed therapy tissue region relative to the graphical electrode representation.

In one embodiment, the processing circuitry is configured for automatically determining the electrode combination based on the selected pre-defined shape and the defined location of the electric field. In this case, the processing circuitry may be configured for automatically determining a plurality of different combinations of the electrodes based on the selected pre-defined shape and the defined location of the electric field, and the control circuitry may be configured for serially conveying electrical stimulation energy into the tissue of the patient via the plurality of determined electrode combinations, thereby creating a clinical effect for each of the determined electrode combinations. The processing circuitry may be configured for assigning a score to each of the determined electrode combinations based on the respective clinical effect, and the user interface may be configured for allowing the user to select one of the determined electrode combination based on the assigned scores.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 29 is a plan view of a program selection screen that can be generated by the CP of FIG. 8;

FIG. 30 is a block diagram of an optimization algorithm that can be used by the CP of FIG. 8 to suggest an optimal electrode configuration for obtaining clinical effects data.

DETAILED DESCRIPTION OF THE EMBODIMENTS

The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a spinal cord stimulator, peripheral nerve stimulator, microstimulator, or in any other neural stimulator configured to treat urinary incontinence, sleep apnea, shoulder subluxation, headache, etc.

Figure 1:
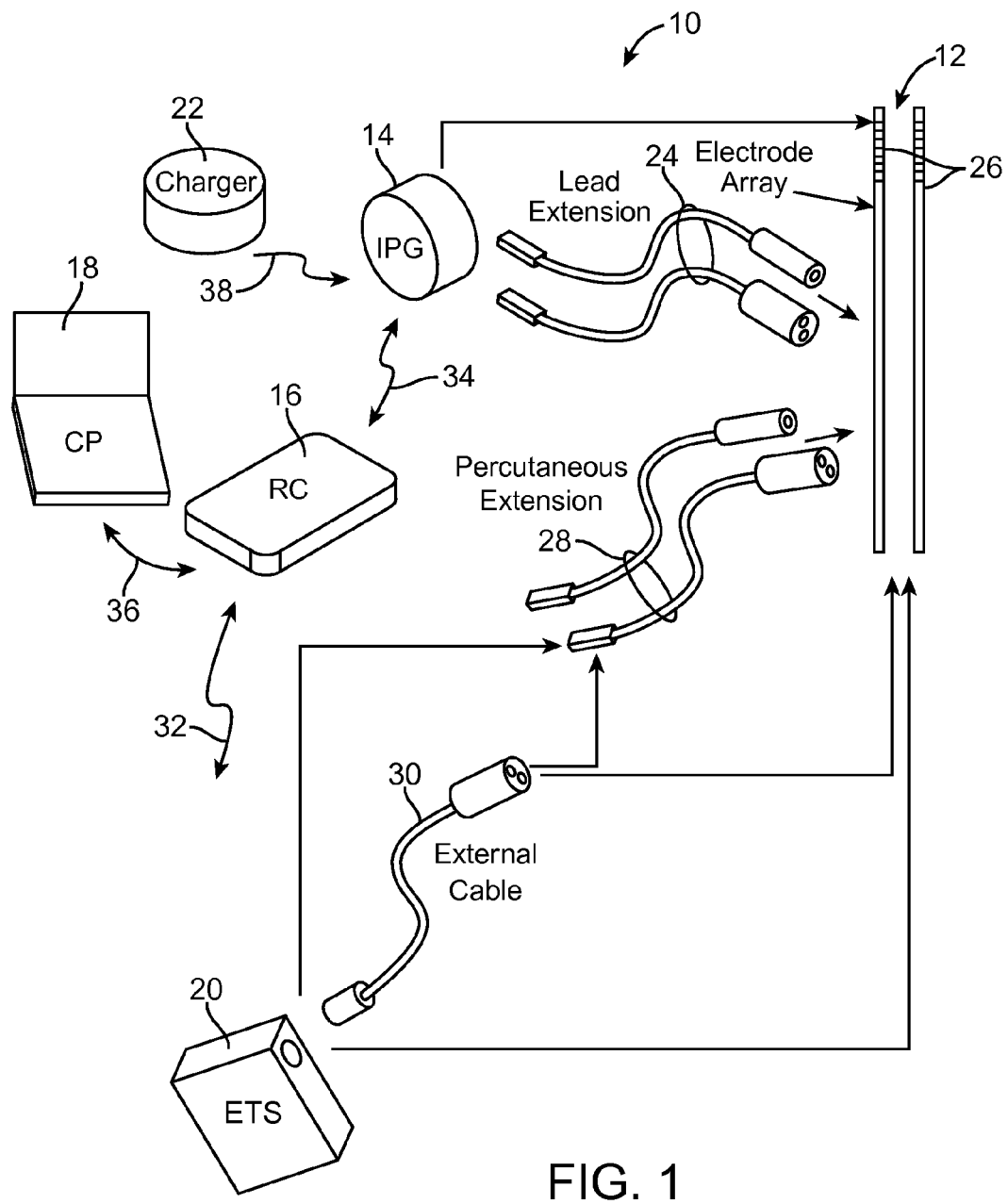
FIG. 1 is a plan view of a Deep Brain Stimulation (DBS) system constructed in accordance with one embodiment of the present inventions.

Turning first to FIG. 1, an exemplary DBS neurostimulation system 10 generally includes at least one implantable stimulation lead 12 (in this case, two), a neurostimulator in the form of an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 may be arranged in-line along the neurostimulation leads 12. In alternative embodiments, the electrodes 26 may be arranged in a two-dimensional pattern on a single paddle lead if, e.g., cortical brain stimulation is desired. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
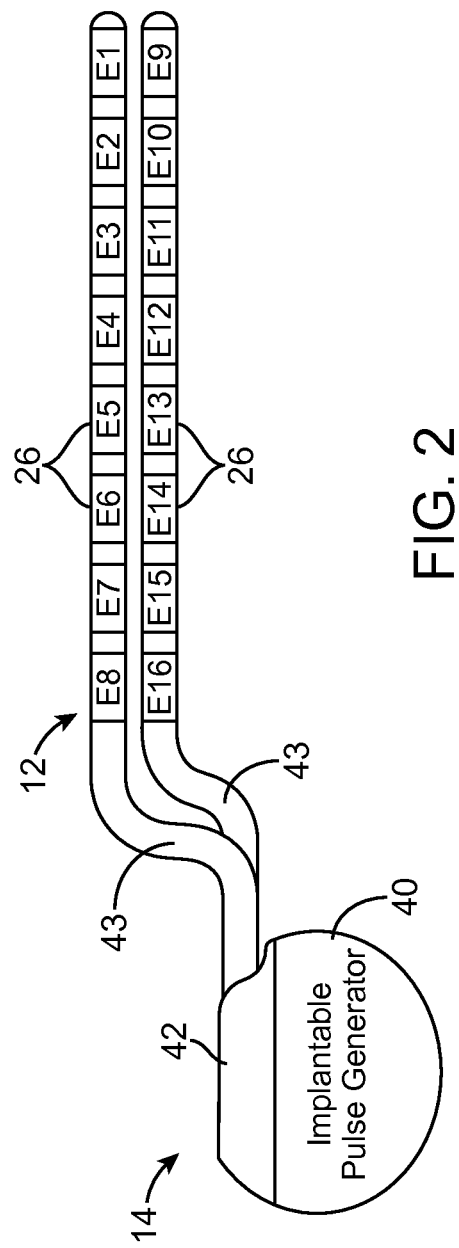
FIG. 2 is a profile view of an implantable pulse generator (IPG) and a first embodiment of neurostimulation leads used in the DBS system of FIG. 1.

Referring to FIG. 2, the IPG 14 comprises an outer case 40 for housing the electronic and other components (described in further detail below), and a connector 42 to which the proximal end of the neurostimulation lead 12 mates in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

Each of the neurostimulation leads 12 comprises an elongated cylindrical lead body 43, and the electrodes 26 take the form of ring electrodes mounted around the lead body 43. One of the neurostimulation leads 12 has eight electrodes 26 (labeled E1-E8), and the other neurostimulation lead 12 has eight electrodes 26 (labeled E9-E16). The actual number and shape of leads and electrodes will, of course, vary according to the intended application.

Figure 3:
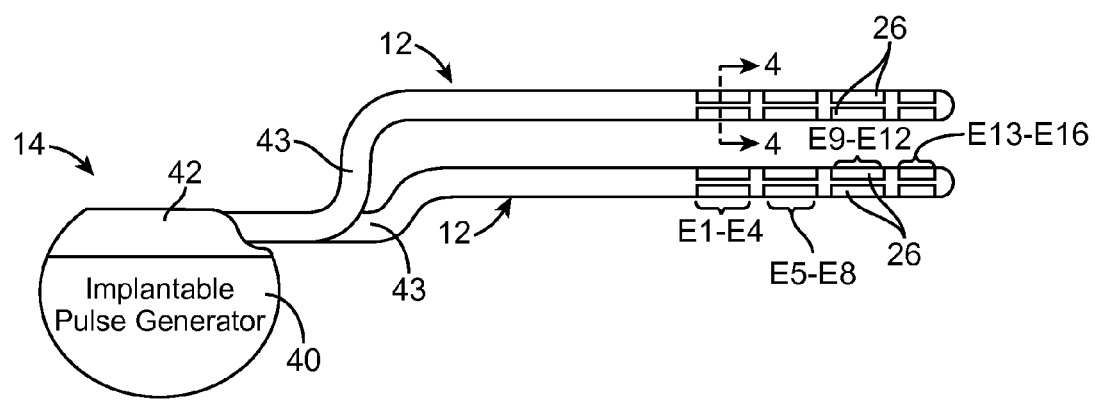
FIG. 3 is a profile view of an implantable pulse generator (IPG) and a second embodiment of neurostimulation leads used in the DBS system of FIG. 1.
Figure 4:
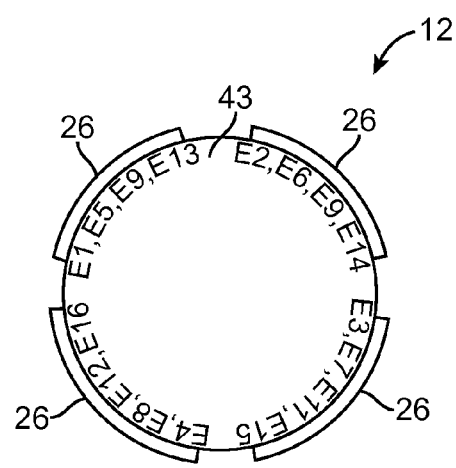
FIG. 4 is a cross-sectional view of one of the neurostimulation leads of FIG. 3, taken along the line 4-4.

In an alternative embodiment illustrated in FIG. 3, the electrodes 26 take the form of segmented electrodes that are circumferentially and axially disposed about the lead body 43. By way of non-limiting example, and with further reference to FIG. 4, one neurostimulation lead 12 may carry sixteen electrodes, arranged as four rings of electrodes (the first ring consisting of electrodes E1-E4; the second ring consisting of electrodes E5-E8; the third ring consisting of electrodes E9-E12; and the fourth ring consisting of E13-E16) or four axial columns of electrodes (the first column consisting of electrodes E1, E5, E9, and E13; the second column consisting of electrodes E2, E6, E10, and E14; the third column consisting of electrodes E3, E7, E11, and E15; and the fourth column consisting of electrodes E4, E8, E12, and E16).

Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

As will be described in further detail below, the IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y). The IPG 14 may be capable of delivering the stimulation energy to the array 22 over multiple channels or over only a single channel.

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. Multipolar stimulation occurs when at least three of the lead electrodes 26 are activated, e.g., two as anodes and the remaining one as a cathode, or two as cathodes and the remaining one as an anode.

In the illustrated embodiment, IPG 14 can individually control the magnitude of electrical current flowing through each of the electrodes. In this case, it is preferred to have use current generators, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention.

Further details discussing the detailed structure and function of IPGs are described more fully in U.S. Pat. Nos. 6,516, 227 and 6,993,384, which are expressly incorporated herein by reference.

Figure 5:
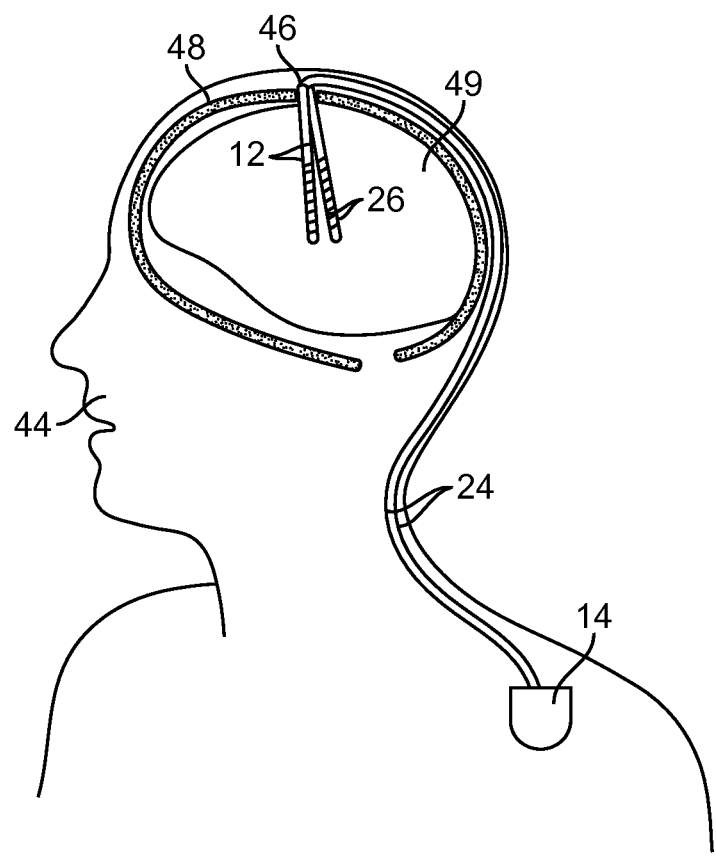
FIG. 5 is a cross-sectional view of a patient's head showing the implantation of stimulation leads and an IPG of the DBS system of FIG. 1.

As shown in FIG. 5, two percutaneous neurostimulation leads 12 are introduced through a burr hole 46 (or alternatively, two respective burr holes) formed in the cranium 48 of a patient 44, and introduced into the parenchyma of the brain 49 of the patient 44 in a conventional manner, such that the electrodes 26 are adjacent a target tissue region, the stimulation of which will treat the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the neurostimulation leads 12 exit the burr hole 46, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the neurostimulation leads 12.

Figure 6:
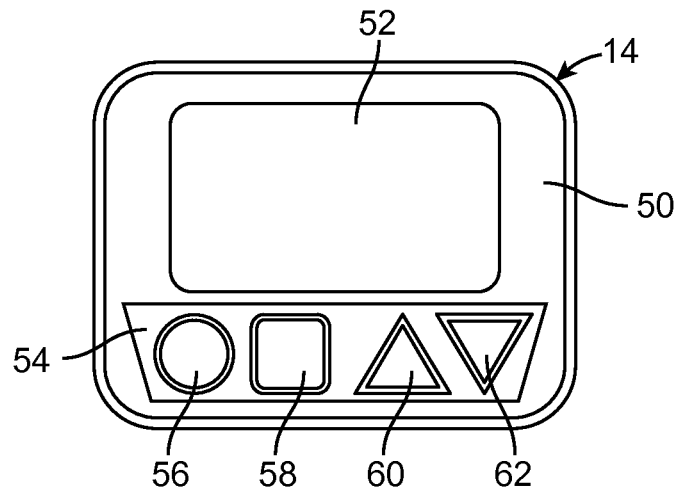
FIG. 6 is front view of a remote control (RC) used in the DBS system of FIG. 1.

Referring now to FIG. 6, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display screen 52 and button pad 54 carried by the exterior of the casing 50. In the illustrated embodiment, the display screen 52 is a lighted flat panel display screen, and the button pad 54 comprises a membrane switch with metal domes positioned over a flex circuit, and a keypad connector connected directly to a PCB. In an optional embodiment, the display screen 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can actuated to increment or decrement any of stimulation parameters of the pulse generated by the IPG 14, including pulse amplitude, pulse width, and pulse rate. For example, the selection button 58 can be actuated to place the RC 16 in an "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 7:
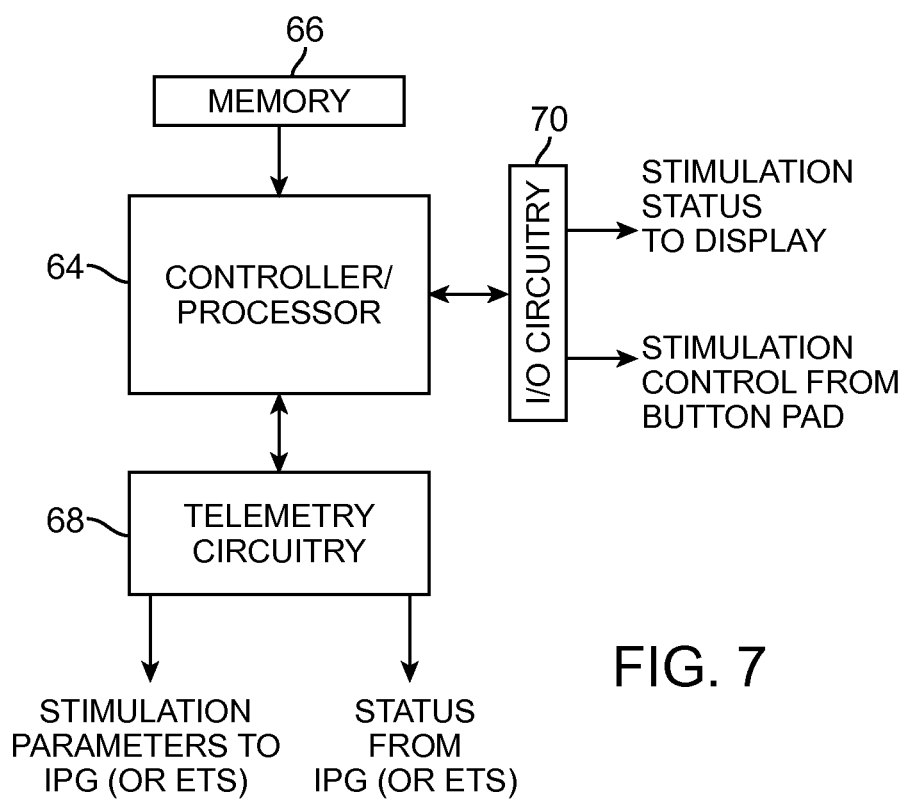
FIG. 7 is a block diagram of the internal components of the RC of FIG. 6.

Referring to FIG. 7, the internal components of an exemplary RC 16 will now be described. The RC 16 generally includes a controller/processor 64 (e.g., a microcontroller), memory 66 that stores an operating program for execution by the controller/processor 64, as well as stimulation parameter sets in a look-up table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display screen 52 (shown in FIG. 6). As well as controlling other functions of the RC 16, which will not be described herein for purposes of brevity, the controller/processor 64 generates new stimulation parameter sets in response to the user operation of the button pad 54. These new stimulation parameter sets would then be transmitted to the IPG 14 (or ETS 20) via the telemetry circuitry 68. Further details of the functionality and internal componentry of the RC 16 are disclosed in U.S. Pat. No. 6,895,280, which has previously been incorporated herein by reference. Notably, while the controller/processor 64 is shown in FIG. 7 as a single device, the processing functions and controlling functions can be performed by a separate controller and processor.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 in the brain.

The overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), smartphone, etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

Figure 8:
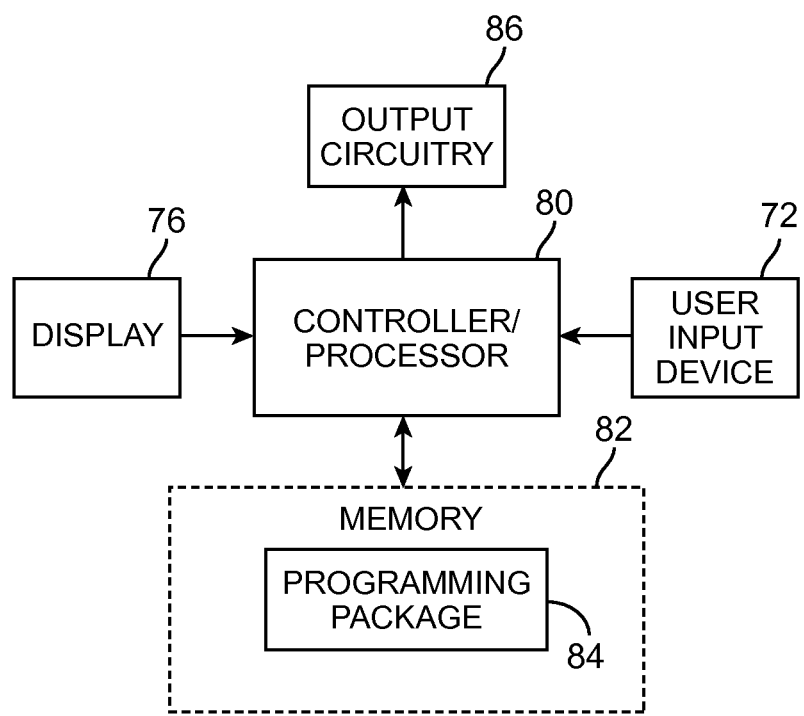
FIG. 8 is a block diagram of the internal components of a clinician's programmer (CP) used in the DBS system of FIG. 1.

Referring to FIG. 8, to allow the user to perform these functions, the CP 18 includes a standard user input device 72 (e.g., a keyboard, mouse, joystick, etc.) to allow a clinician to input information and control the process and a display monitor 76 housed in a case. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch. The CP 18 generally includes a controller/processor 80 (e.g., a central processor unit (CPU)) and memory 82 that stores a stimulation programming package 84, which can be executed by the controller/processor 80 to allow the user to program the IPG 14, and RC 16. The CP 18 further includes output circuitry 86 for downloading stimulation parameters to the IPG 14 and RC 16 and for uploading stimulation parameters already stored in the memory 66 of the RC 16, via the telemetry circuitry 68 of the RC 16. Notably, while the controller/processor 80 is shown in FIG. 8 as a single device, the processing functions and controlling functions can be performed by a separate controller and processor. Thus, it can be appreciated that the controlling functions described below as being performed by the CP 18 can be performed by a controller, and the processing functions described below as being performed by the CP 18 can be performed by a processor.

Execution of the programming package 84 by the controller/processor 80 provides a multitude of display screens (not shown) that can be navigated through via use of the user input device 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a therapeutic map (e.g., body regions targeted for therapy, body regions for minimization of side-effects, along with metrics (e.g., Unified Parkinson's Disease Rating Scale (UPDRS)) of success for said targets) of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

The user interface includes a series of programming screens with various control elements that can be actuated to perform functions corresponding to the control elements. In the illustrated embodiment, control elements are implemented as a graphical icon that can be clicked with a mouse in the case of a conventional display device. Alternatively, the display device may have a digitizer screen (e.g., a touchscreen) that can be touched or otherwise activated with an active or passive digitizer stylus. More alternatively, the control elements described herein may be implemented as a joy stick, touchpad, button pad, group of keyboard arrow keys, mouse, roller ball tracking device, horizontal or vertical rocker-type arm switches, etc., that can be pressed or otherwise moved to actuate the control elements. Alternatively, other forms of entering information can be used, such as textual input (e.g., text boxes) or microphones.

Figure 9:
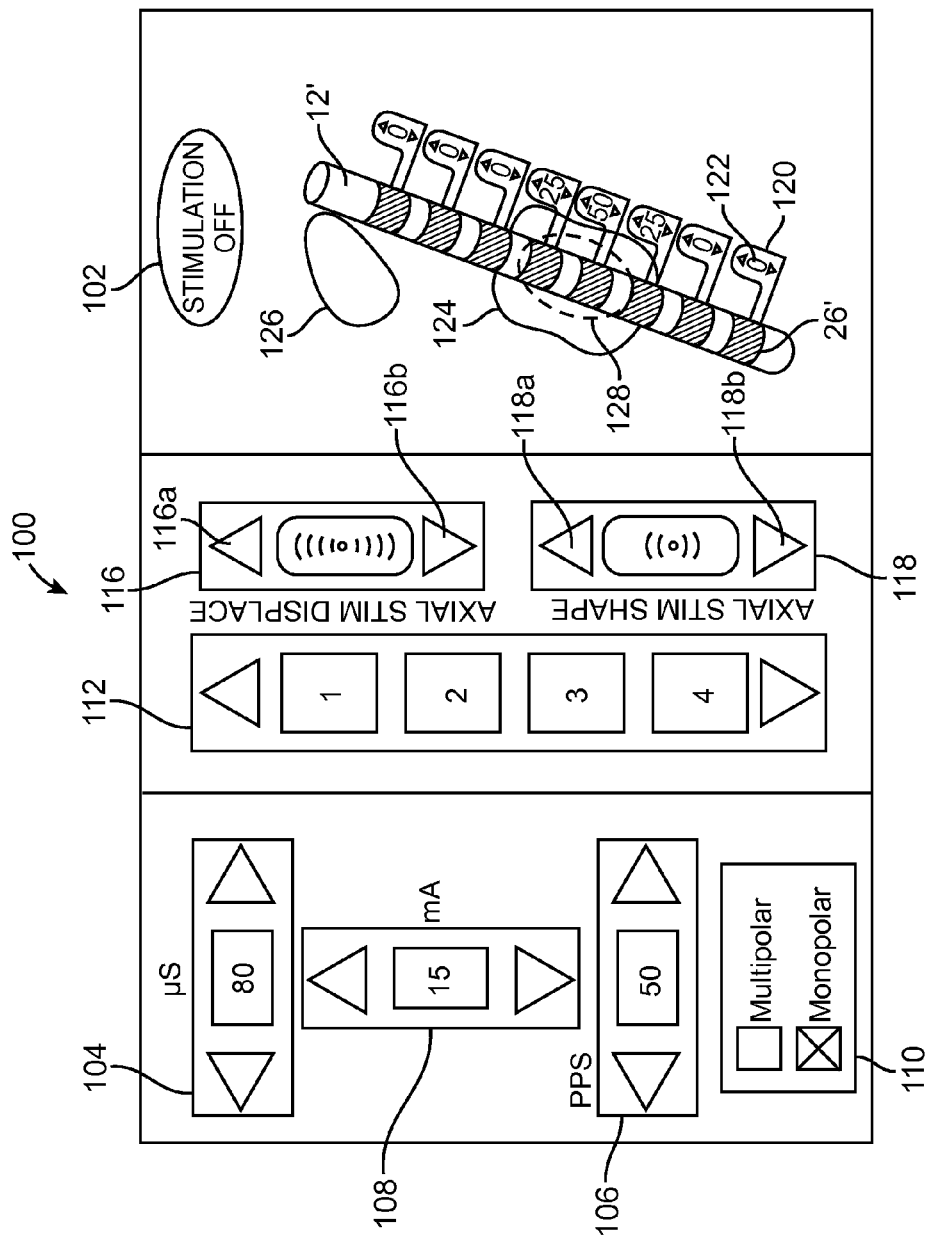
FIG. 9 is a plan view of a one embodiment of a programming screen that can be generated by the CP of FIG. 8.

In particular, a programming screen 100 can be generated by the CP 18, as shown in FIG. 9. The programming screen 100 allows a user to perform stimulation parameter testing. To this end, the programming screen 100 comprises a stimulation on/off control 102 that can be alternately clicked to turn the stimulation on or off. The programming screen 100 further includes various stimulation parameter controls that can be operated by the user to manually adjust stimulation parameters. In particular, the programming screen 100 includes a pulse width adjustment control 104 (expressed in microseconds (µs)), a pulse rate adjustment control 106 (expressed in pulses per second (pps), and a pulse amplitude adjustment control 108 (expressed in milliamperes (mA)). Each control includes a first arrow that can be clicked to decrease the value of the respective stimulation parameter and a second arrow that can be clicked to increase the value of the respective stimulation parameter. The programming screen 100 also includes multipolar/monopolar stimulation selection control 110, which includes check boxes that can be alternately clicked by the user to provide multipolar or monopolar stimulation. In an optional embodiment, the case 40 of the IPG 14 may be treated as one of the lead electrodes 26, such that both the case electrode 40 and at least one of the lead electrodes 26 can be used to convey anodic electrical current at the same time. Additionally, the case electrode may be configured with all the programmability of a lead electrode, with full anodic and cathodic fractionalization.

The programming screen 100 also includes an electrode combination control 112 having arrows that can be clicked by the user to select one of four different electrode combinations 1-4. Each of the electrode combinations 1-4 can be created using a variety of control elements. The programming screen 100 also includes a set of axial electrical stimulation field displacement control elements 116 and a set of axial electrical stimulation field shaping control elements 118.

When any of the axial electrical stimulation field displacement control elements 116 is actuated, control signals are generated in response to which the controller/processor 80 is configured for generating stimulation parameter sets designed to axially displace the locus of the electrical stimulation field relative to the axis of the lead 12. Preferably, the control signals that are generated in response to the actuation of the axial electrical stimulation field displacement control elements 116 or the alternative control elements are directional, meaning that the locus of the electrical stimulation field will be displaced in a defined direction in response to a continual actuation of a single control element irrespective of the current position of the locus electrical stimulation field locus. When any of the axial electrical stimulation field shaping control elements 118 is actuated, control signals are generated in response to which the controller/processor 80 is configured for generating stimulation parameter sets designed to axially expand or contract the electrical stimulation field relative to its locus.

The control elements 116, 118 may be continually actuated (i.e., by continuously actuating one of the control elements 116, 118, e.g., by clicking on one of the control elements 116, 118 and holding the click (i.e., continuous actuation of the control following the initial "click"), or repeatedly actuating one of the control elements 116, 118, e.g., by repeatedly clicking and releasing one of the control elements 116, 118) to generate a series of control signals in response to which the controller/processor 80 is configured for generating the plurality of stimulation parameter sets. The output telemetry circuitry 86 is configured for transmitting these stimulation parameters sets to the IPG 14.

Each of the sets of control elements 116, 118 takes the form of a double arrow (i.e., two oppositely pointing control element arrows) that can be actuated to modify the electrical stimulation field depending on the mode of operation. For example, an upper arrow control element 116a can be clicked to axially displace the locus of the electrical stimulation field (i.e., along the axis of the lead 12) in the proximal direction; a lower arrow control element 116b can be clicked to axially displace the locus of the electrical stimulation field (i.e., along the axis of the lead 12) in the distal direction; a lower arrow control element 118a can be clicked to axially contract the electrical stimulation field about its locus, and an upper arrow control element 118b can be clicked to axially expand the electrical stimulation field about its locus.

The locus of the electrical stimulation field may be displaced, e.g., by gradually "steering" or shifting electrical current between electrodes in a single timing channel. For example, the locus of the electrical stimulation field can be gradually displaced axially in the distal direction along the lead 12 by gradually including electrodes in a stimulating electrode group and gradually excluding other electrodes from the stimulating electrode group in the single timing channel.

Although the programming screen 100 illustrates only one neurostimulation lead 12 with electrodes arranged in only one dimension, thereby allowing the electrical current to only be steered in one dimension, it should be appreciated that the programming screen 100 may additionally illustrate the other neurostimulation lead 12, thereby arranging the electrodes in two dimensions and allowing the electrical current to be steered in two dimensions. In this case, using appropriate control elements (e.g., left and right arrows), the locus of the electrical stimulation field can be displaced in the transverse direction (perpendicular to the axial direction, and in this case, left or right) and/or the electrical stimulation field can be expanded or contracted in the transverse direction. Of course, the electrodes can be arranged in three-dimensions (e.g., by arranging three neurostimulation leads in three-dimensions or by using electrodes on a single neurostimulation lead that are arranged in three-dimensions, e.g., the segmented neurostimulation leads described in U.S. Provisional Patent Application Ser. No. 61/374,879), in which case, the electrical current can be steering in three-dimensions.

Further details discussing different techniques for modifying an electrical stimulation field is disclosed in U.S. Provisional Patent Application 61/374,879, entitled "User Interface for Segmented Neurostimulation Leads," which is expressly incorporated herein by reference. In an optional embodiment where the neurostimulation lead 12 with segmented electrodes 26 (see FIG. 3) are used, additional control elements can be provided to circumferentially displace the locus of the electrical stimulation field, circumferentially contract or expand the electrical stimulation field, radially displace the locus of the electric field, or radially contract or expand the electrical stimulation field, as disclosed in U.S. Provisional Patent Application 61/374,879.

The programming screen 100 displays three-dimensional graphical renderings of the lead 12' and electrodes 26'. In an optional embodiment, iconic control elements 120 are graphically linked to the three-dimensional electrode renderings 26'. Continual actuation of the control elements 120 generates control signals that prompt the controller/processor 80 to generate stimulation parameters designed to modify the electrical stimulation field, which stimulation parameters are then transmitted from the output circuitry 86 of the CP 18 to the IPG 14. In the illustrated embodiment, each of the control elements 120 has an up arrow and a down arrow that can be respectively actuated (e.g., by clicking) to respectively increase or decrease the electrical current flowing through the electrode 26 corresponding to the graphical electrode rendering 26' to which the actuated control element 120 is graphically linked.

Actuation of any of the control elements 120 essentially steers electrical current from other active electrodes to the electrode associated with the actuated control element 120 or from the electrode associated with the actuated control element 120 to other active electrodes. In this manner, the locus of the electrical stimulation field can be displaced, the shape of the electrical stimulation field can be modified, and if two separate electrical stimulation fields current exist, electrical current can be shifted from one of the electrical stimulation fields (effectively decreasing its size) to another of the electrical stimulation fields (effectively increasing its size).

The control element 120 also includes an indicator 122 that provides an indication of the amount of electrical current flowing through each of the electrodes 26 in terms of a fractionalized current value. The indicators 122 may perform this function when the respective control elements 120 are actuated or when the axial electrical stimulation field displacement control elements 116 and axial electrical stimulation field shaping control elements 118 are actuated.

The programming screen 100 displays the three-dimensional graphical renderings of the lead 12' and electrodes 26' in registration with anatomical regions of interest, and in particular, a therapy tissue region 124, the stimulation of which is known or believed to provide the needed therapy to the patient, and a side-effect tissue region 126, the stimulation of which is known or believed to provide an undesirable side-effect for the patient. The anatomical regions of interest may be anatomical structures, the boundaries of which are naturally defined, or may be arbitrary volumes of interest known to result in therapy or a side-effect when stimulated. In the illustrated embodiment, the anatomical regions of interest are obtained from a generally available atlas. In the illustrated embodiment, the anatomical regions of interest are shown as being two-dimensional, although in other embodiments, the anatomical regions of interest may be three-dimensional in nature.

Based on the current stimulation parameter set, the CP 18 may estimate of a resulting region of tissue activation (RTA) 128, which can be displayed on the programming screen 100 with the graphical lead 12' and anatomical regions of interest 124, 126. Further details discussing technique for computing the estimate of a RTA 128 are disclosed in A. M. M. Frankemolle, et al., *Reversing Cognitive-Motor Impairments in Parkinson's Disease Patients Using a Computational Modelling Approach to Deep Brain Stimulation Programming*, Brain 2010; pp. 1-16), which is expressly incorporated herein by reference.

Alternatively, instead of computing and displaying a RTA, the CP 18 may compute an electric field (not shown) from the current stimulation parameter set, which may be displayed relative to the graphical lead 12' and anatomical regions of interest 124,126. In the illustrated embodiment, although the graphical lead 12', anatomical regions of interest 124,126, and the RTA 128 are displayed in an oblique view, they can be alternatively displayed in any one or more of traditional planes of section (e.g., axial, coronal, and sagittal.

Most pertinent to the present inventions, execution of the programming package 84 provides a more intuitive user interface that allows a user to readily determine the extent that to which specified electrodes influence one or more clinical effects (e.g., a therapeutic effect and/or side-effect), modify anatomical regions of interest (e.g., a therapy tissue region and/or a side-effect tissue region) to be specific to the patient, and/or matching a electric field, and thus the electrode combination that best generates the electric field, to a therapy tissue region. To this end, the user interface allows the user to select one or more brain disorders to be treated (FIG. 10), perform a clinical analysis to determine the extent to which each of the electrodes 26 influences anatomical regions of interest (FIGS. 11-12, 15-16, and 19-20), determine the shape and/or boundaries of target and non-target tissue regions (FIGS. 13-14 and 17-18), optionally modify the shape and/or location of anatomical regions of interest (FIGS. 21-24), determining the shape of the electric field that best matches the target tissue region(s) (FIGS. 25-28), determining the program that best emulates the shape of the electric field (FIG. 29), and programming the IPG 14/RC 16 with the selected program.

Figure 10:
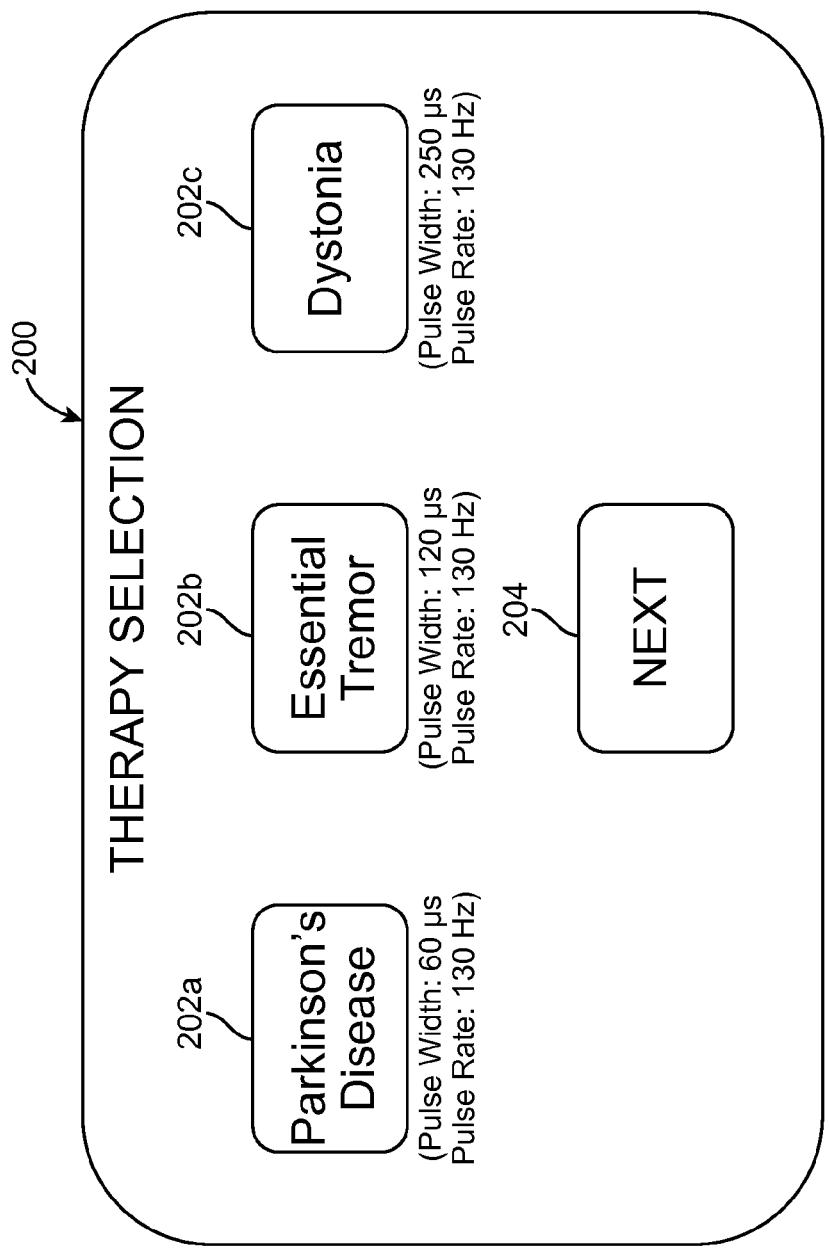
FIG. 10 is a plan view of one embodiment of a therapy selection screen that can be generated by the CP of FIG. 8.

As shown in FIG. 10, a therapy selection screen 200, which allows a user to select one or more brain disorders to be treated, can be initially generated by the CP 18. In particular, the therapy selection screen 200 includes graphical controls in the form of a series of disorder boxes 202a, 202b, 202c that can be clicked to select the brain disorder to be treated. In the illustrated embodiment, the disorder box 202a can be clicked to treat Parkinson's Disease, the disorder box 202b can be clicked to treat Essential Tremor, and the disorder box 202c can be clicked to treat Dystonia. Additional disorder boxes may be displayed in the therapy selection screen 200, so that other types of brain disorders can be treated. Default stimulation parameters, and in this case, a default pulse width and pulse rate, for each disorder to be treated are shown below the respective disorder box 202. In the illustrated embodiment, a default pulse width of 60 μs and a default pulse rate of 130 Hz is shown for treatment of the Parkinson's Disease, a default pulse width of 120 μs and a default pulse rate of 130 Hz is shown for the treatment of Essential Tremor, and a default pulse width of 250 μs and a default pulse rate of 130 Hz is shown for the treatment of Dystonia. The default pulse width and default pulse rate, as well as the pulse amplitude, can be varied by the user using the programming screen 100. More than one of the disorder boxes can be clicked to treat multiple brain disorders. The therapy selection screen 200 further includes a next button 204 that can be clicked to continue to the next screens described below.

Figure 11:
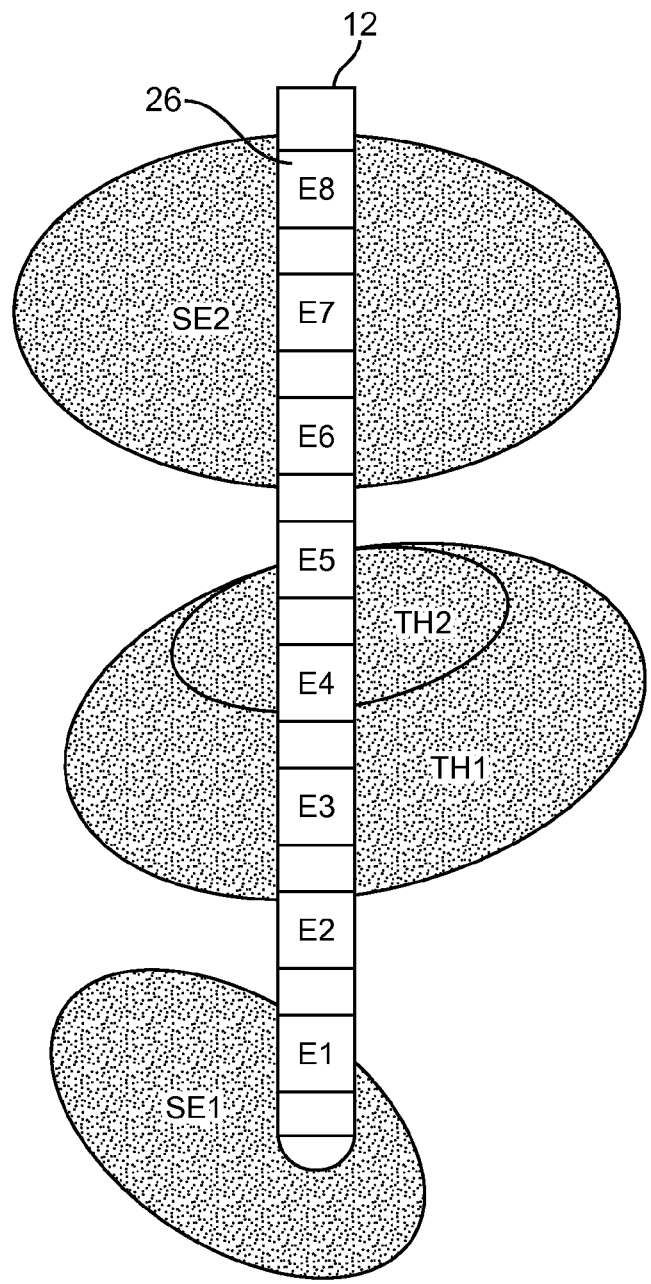
FIG. 11 is a plan view of a neurostimulation lead implanted in tissue with therapy tissue regions and side-effect tissue regions.

Significantly, the CP 18 can be used to instruct the IPG 14 to serially convey electrical stimulation energy into the tissue via different combinations of the electrodes 26, thereby creating one or more clinical effects for each of the different electrode combinations. For example, assuming that a neurostimulation lead 12 is implanted in tissue containing a first therapy region TH1 (e.g., one the stimulation of which alleviates or eliminates the symptoms of Parkinson's Disease), a second therapy region TH2 (e.g., one the stimulation of which alleviates or eliminates the symptoms of Dystonia), a first side-effect region SE1 (e.g., one the stimulation of which causes nausea), and a second side-effect region SE2 (e.g., one the stimulation of which causes headache), as shown in FIG. 11, conveyance of electrical stimulation energy via different combinations of the electrodes will cause either a therapeutic effect, a side-effect, or both.

The CP 18 quantifies the influence of each of the different electrode combinations on the clinical effects. For example, if electrode E1 is activated to convey electrical stimulation energy, it may be concluded that this electrode somewhat influences the side-effect associated with the first side-effect region SE1. If electrode E2 is activated to convey electrical stimulation energy, it may be concluded that this electrode somewhat influences the therapeutic effect associated with the first therapy region TH1 and the side-effect associated with the first side-effect region SE1. If electrode E3 is activated to convey electrical stimulation energy, it may be concluded that this electrode highly influences the therapeutic effect associated with the first therapy region TH1. If electrode E4 is activated to convey electrical stimulation energy, it may be concluded that this electrode highly influences therapeutic effects associated with the first and second therapy regions TH1, TH2. If electrode E5 is activated to convey electrical stimulation energy, it may be concluded that this electrode somewhat influences a side-effect associated with the second side-effect region SE2 and therapeutic effects associated with the first and second therapy regions TH1, TH2. If any of electrodes E6-E8 is activated to convey electrical stimulation energy, it may be concluded that these electrodes highly influence a side-effect associated with the second side-effect region SE2.

In the preferred embodiment, the intensity level of the electrical stimulation energy conveyed via each electrode combination is incrementally varied, such that the influence by a specific electrode combination on the clinical effects can be determined by the CP 18 for each of the different intensity levels. The influence by a specific electrode combination on the clinical effects can be determined by the CP 18, e.g., based on clinical information entered by the user. For example, as described in further detail below, the user may enter into the CP 18 the intensity level at which the patient experiences a therapeutic effect or a side-effect for the specific electrode combination. Alternatively, the influence by a specific electrode combination on the clinical effects can be determined by the CP 18, e.g., based on monitored clinical information automatically provided to the CP 18 from monitoring circuitry (not shown).

As will be described in further detail below with respect to various embodiments, once the influences of each electrode combination on the clinical effects have been determined, the CP 18 can then generate and display graphical indications of these determined influences, such that the user can determine an extent to which each of the different electrode combinations influences the clinical effects. For the purposes of this specification, the term "graphical" means a textual or non-textual representation. Although the embodiments described herein display non-textual representations of the determined influences, which provides a readily understandable visual from which the user may determine the extent to which each of the different electrode combinations influences the clinical effects, textual representations of the determined influences can be used in addition to, or alternative, to the non-textual graphical indications of the determined influences.

Figure 12:
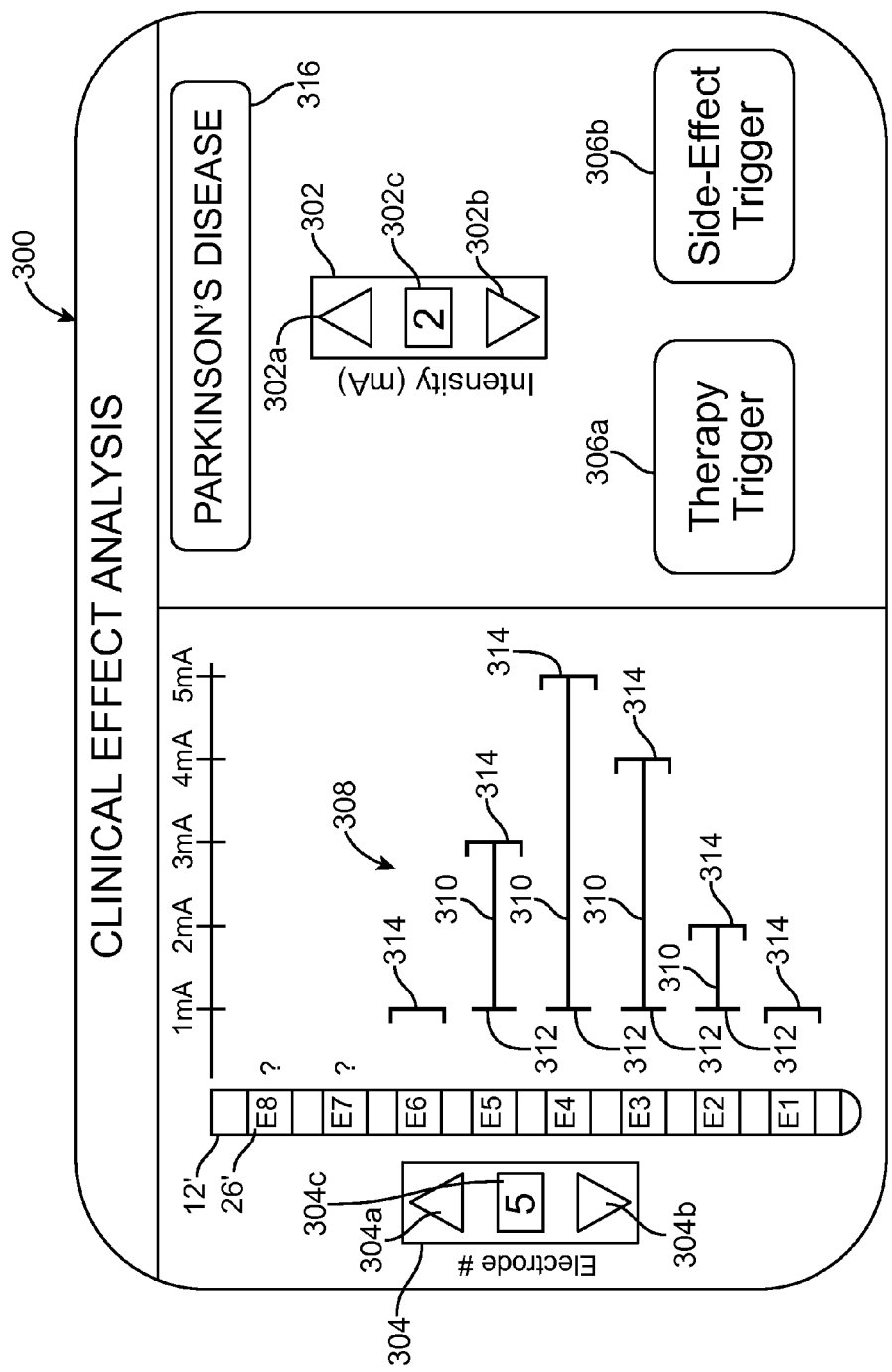
FIG. 12 is a plan view of one embodiment of a clinical effects analysis screen that can be generated by the CP of FIG. 8.

In one embodiment shown in FIG. 12, a clinical effect analysis screen 300 allows a user to readily determine the extent to which each of the different electrode combinations influences the clinical effects. In particular, the clinical effect analysis screen 300 includes an intensity level adjustment control 302, which includes an upper arrow 302a that can be clicked to increase the intensity value of the electrical stimulation energy conveyed via a specified electrode combination, and a lower arrow 302b that can be clicked to decrease the intensity value of the electrical stimulation energy conveyed via a specified electrode combination. The intensity level adjustment control 302 also includes an indicator 302c that provides an indication of the intensity of the conveyed electrical stimulation energy, and in the illustrated embodiment, the amount of electrical current flowing through a specified electrode combination in milliamperes. In the illustrated embodiment, the range of intensity values that can be selected is 0-5 mA in one milliampere increments, although in other embodiments, the range of intensity values may be larger or smaller, or have a higher or lower resolution. The pulse width and pulse rate of the conveyed electrical stimulation energy will correspond to the default parameters of the disorder selected to be treated in the therapy selection screen 200. In an optional embodiment, the clinical effect analysis screen 300 may include a pulse width adjustment control and a pulse rate adjustment control (not shown) similar to the adjustment controls 104 and 106 described above with respect to FIG. 9, so that the pulse width and/or pulse rate of the conveyed electrical stimulation energy may be adjusted from their default values.

The clinical effect analysis screen 300 also includes a graphical representation of the neurostimulation lead 12' and corresponding electrodes 26'. In the illustrated embodiment, only the graphical representation for one neurostimulation lead 12' having electrodes E1-E8 is displayed, although graphical representations for multiple neurostimulation leads 12 or alternative neurostimulation leads (e.g., the segmented neurostimulation lead illustrated in FIG. 3) can be displayed.

The clinical effect analysis screen 300 also includes an electrode selection control 304 that can be used to select the specific electrode combination to be currently tested (i.e., the specific electrode combination through which the electrical stimulation energy will flow). In the illustrated embodiment, each electrode combination has a single electrode. To this end, the electrode selection control 304 includes an upper arrow 304a that can be clicked to increase the index number of the electrode 26, and a lower arrow 304b that can be clicked to decrease the index number of the electrode 26. The electrode selection control 304 also includes an indicator 304c that provides an indication of the selected electrode 26. In the illustrated embodiment, electrical stimulation energy is conveyed through each selected electrode 26 in a monopolar manner.

The clinical effect analysis screen 300 further includes clinical information entry buttons 306 that allows the user to enter clinical information, and in this embodiment, a therapeutic effect trigger button 306a that can be actuated when the patient experiences a therapeutic effect, and a side-effect trigger button 306b that can be actuated when the patient experiences a side-effect. Verbal feedback from the patient may prompt the user to actuate either of the clinical information entry buttons 306. A therapeutic effect may be considered to be a mitigation of a symptom (or a component of the symptom) caused by a disorder, whereas a side-effect can be considered a symptom (or a component of the symptom) of the electrical stimulation. The CP 18 will be capable of determining the influence of each electrode 26 on the therapeutic and side-effects based on the clinical information entered by the user via the clinical information entry buttons 306.

In this embodiment, the CP 18 quantifies the influence of each electrode 26 on the therapeutic effect by determining the range of incremental intensity levels at which a metric of a therapeutic effect occurs based on clinical information entered by the user via the clinical information entry buttons 306, and further determining the incremental intensity level at which a metric of a side-effect initially occurs. In this embodiment, the metric of the therapeutic effect is an absolute metric, and in particular, whether the perception threshold of the therapeutic effect has been reached or exceeded, and the metric of the side-effect is also an absolute metric, and in particular, whether the perception threshold of the therapeutic effect has been reached or exceeded.

In the illustrated embodiment, for each activated electrode, the intensity level adjustment control 302 can be manipulated to incrementally increase the intensity level of the electrical stimulation energy, and at each intensity level, the patient may provide feedback as to whether a therapeutic effect or a side-effect is experienced. For example, for electrode E1, the intensity level of the electrical stimulation energy can be incrementally increased, with the patient providing feedback at each of the incremental intensity levels; for electrode E2, the intensity level of the electrical stimulation energy can be incrementally increased, with the patient providing feedback at each of the incremental intensity levels; and so on.

Thus, at each intensity level for each activated electrode, the user may actuate the therapeutic effect trigger button 306a if the therapeutic effect is perceived at all by the patient, and may actuate the side-effect trigger button 306b if a side-effect is perceived at all by the patient, such that the CP 18 may determine the range of intensity levels at which the perception threshold of the therapeutic effect is met or exceeded and the intensity level at which the perception threshold of the side-effect is initially met or exceeded for each activated electrode. Preferably, in the case where the patient has multiple disorders to be treated, the user will actuate the therapeutic effect trigger button 306a if a therapeutic effect associated with any of the multiple disorders is perceived, even though a therapeutic effect associated with other multiple disorders may not be perceived.

In other embodiments, the metric of the therapeutic effect may be, e.g., whether a relative level (e.g., a particular comfort level) of the therapeutic effect has been reached or exceeded, and the metric of the side-effect may be, e.g., whether a relative level (e.g., an annoyance level or an intolerable level) has been reached or exceeded. As will be described in other embodiments below, the metric of the therapeutic effect and/or side-effect may take the form of a score that can be separately assigned to a therapeutic effect or side-effect or a wellness score that takes into account both the therapeutic effect or the side-effect.

Based on the clinical information entered by the user (in this embodiment, by pushing the therapeutic effect trigger button 306a or the side-effect trigger button 306b at the appropriate times), the CP 18 may determine the highest intensity level at which the therapeutic effect occurs prior to the initial occurrence of a side-effect. The CP 18 may then graphically generate and display this information in the form of a bar map 308 having a plurality of bars 310, each of which indicates for each of the electrodes E1-E8 the highest intensity level at which a therapeutic effect occurs prior to the initial occurrence of the side-effect. The horizontal axis of the bar map represents intensity level in increments of one milliamp here, and the vertical axis of the bar map represents the electrode number.

In the case where there is at least one intensity level at which the therapeutic effect occurs prior to the initial occurrence of a side-effect, the bar 310 will be a particular color (e.g., green) indicating the range of the intensity levels at which the therapeutic effect occurs. A first tick 312 (e.g., green color) can be placed at the beginning of the bar 310, indicating the intensity level at which the therapeutic effect initially occurs, and a second tick 314 (e.g., red color) can be placed on the bar 310, indicating the intensity level at which the side-effect initially occurs. In the case where there is no intensity level at which the therapeutic effect occurs prior to the initial occurrence of the side-effect (i.e., the side-effect occurs prior to the therapeutic effect). In this case where an electrode has not been tested, a question mark "?" is displayed next to that electrode.

For example, as shown in FIG. 12 and with further reference to FIG. 11, only a side-effect tick 314 is displayed adjacent electrode E1, indicating that a side-effect was perceived prior to a therapeutic effect. Viewing this, a user may understand electrode E1 to highly influence a side-effect region without influencing a therapeutic effect at all, which corresponds to electrode E1 being partially contained in the first side-effect region SE1. The relatively short bar 310 displayed adjacent electrode E2 (in the range of 1 mA-2 mA) indicates to the user that electrode E2 somewhat influences a therapeutic effect and a side-effect, which corresponds to electrode E2 being between the first therapy region TH1 and the first side-effect region SE1. The relatively long bar 310 displayed adjacent electrode E3 (in the range of 1 mA-4 mA) indicates to the user that electrode E3 highly influences a therapeutic effect, which corresponds to electrode E3 being fully within the first therapy region TH1. The longer bar 310 displayed adjacent electrode E4 (in the range of 1 mA-5 mA) indicates to the user that electrode E4 influences a therapeutic effect the most out of all of the electrodes, which corresponds to electrode E4 being in the center of the first therapy region TH1. The relatively moderate length bar 310 displayed adjacent electrode E5 (in the range of 1 mA-3 mA) indicates to the user that electrode E5 somewhat influences a therapeutic effect and a side effect, which corresponds with electrode E5 being partially contained in the first and second therapy regions TH1, TH2, and near the second side-effect region SE2. Only a side-effect tick 314 is displayed adjacent electrode E6, indicating that electrode E6 to highly influence a side-effect region without influencing a therapeutic effect at all, which corresponds to electrode E6 being contained in the second side-effect region SE1. The question marks adjacent electrodes E7 and E8 have not been tested, presumably by choice of the user based on the fact that the therapeutic effect substantially diminished at electrode E6.

Although this embodiment has been described as activating each of the electrodes E1-E8 to either an "on" state (100% of the stimulation energy is provided by the electrode) or an "off" state (0% of the stimulation energy is provided by the electrode), in effect, allowing the electrodes to be sequentially turned on and off up or down the neurostimulation lead 12, electrical current can be steered along the neurostimulation lead 12, such that a plurality of the electrodes can have fractionalized current values. For example, electrical current can be steered up or down the neurostimulation lead 12 in 10% increments by, e.g., clicking the up and down arrows of a control mechanism similar to the electrode selection control 304.

For example, the process may start with 100% of the electrical current at electrode E1, then 90% of the electrical current at electrode E1 and 10% of the electrical current at electrode E2, then 80% of the electrical current at electrode E1 and 20% of the electrical current at electrode E2, and so forth, until a sufficient number of electrodes have been tested. At each fractionalized electrode combination, the user may incrementally increase the intensity level of the stimulation energy in the manner discussed above, so that clinical information can be obtained for each fractionalized electrode combination. A bar map can be generated in the same manner discussed above, with the exception that there will be many more bars (one for each fractionalized electrode combination).

In any event, with knowledge that electrode E4 and the adjacent electrodes influence a therapeutic effect, the user may accordingly program the IPG 14 with the appropriate electrode combination. In one embodiment, the CP 18 dynamically generates and displays the bar map 308 as the user enters the clinical information via the clinical trigger buttons 306. In an alternative embodiment, the CP 18 generates and displays the bar map 308 only after the user has entered all of the clinical information necessary to complete the bar map 308, e.g., when prompted by the user via a control button (not shown). The bar map 308 is preferably stored in memory 82 for use in a subsequent programming session, which may be fully manually performed by the user or may be automated by the CP 18. Optionally, the bar map 308 may be displayed and stored in memory 82 for other purposes. For example, the bar map 308 may be displayed in a report or on another device, in a database (e.g., for population analysis), or in a computer file that could be used by another application.

The clinical effect analysis screen 300 further includes a disorder treatment indicator 316 that provides an indication to the user of the current disorder that is being treated (i.e., the disorder selected in the therapy selection screen 200 illustrated in FIG. 10). This indicator can be stored with the bar map 308 in memory 82, such that the user may knows the treated disorder to which the bar map 308 corresponds when subsequently recalled from memory 82. It should also be appreciated that if multiple disorders are treated, several bar maps 308 may be generated, displayed, and stored in memory, one bar map 308 for each disorder to be treated. For example, after generating, displaying, and storing a bar map 308 for one disorder, the user can return to the therapy selection screen 200, select another disorder via the disorder boxes 202, and then go to the clinical effects analysis screen 300 to prompt the CP 18 to generate, display, and store another bar map 308 for the new disorder to be treated.

Figure 13:
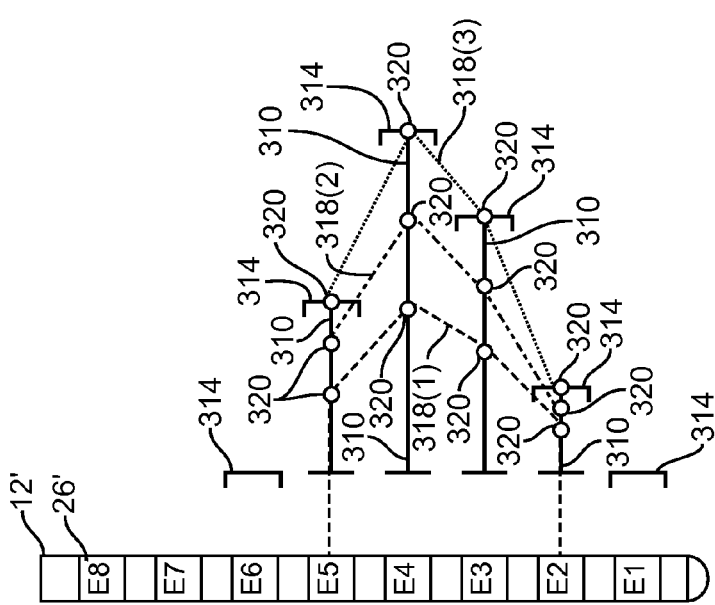
FIG. 13 is a plan view of a method used by the CP of FIG. 8 to determine one-half of a target tissue region from a bar map generated in the clinical effects analysis screen of FIG. 12.
Figure 15A:
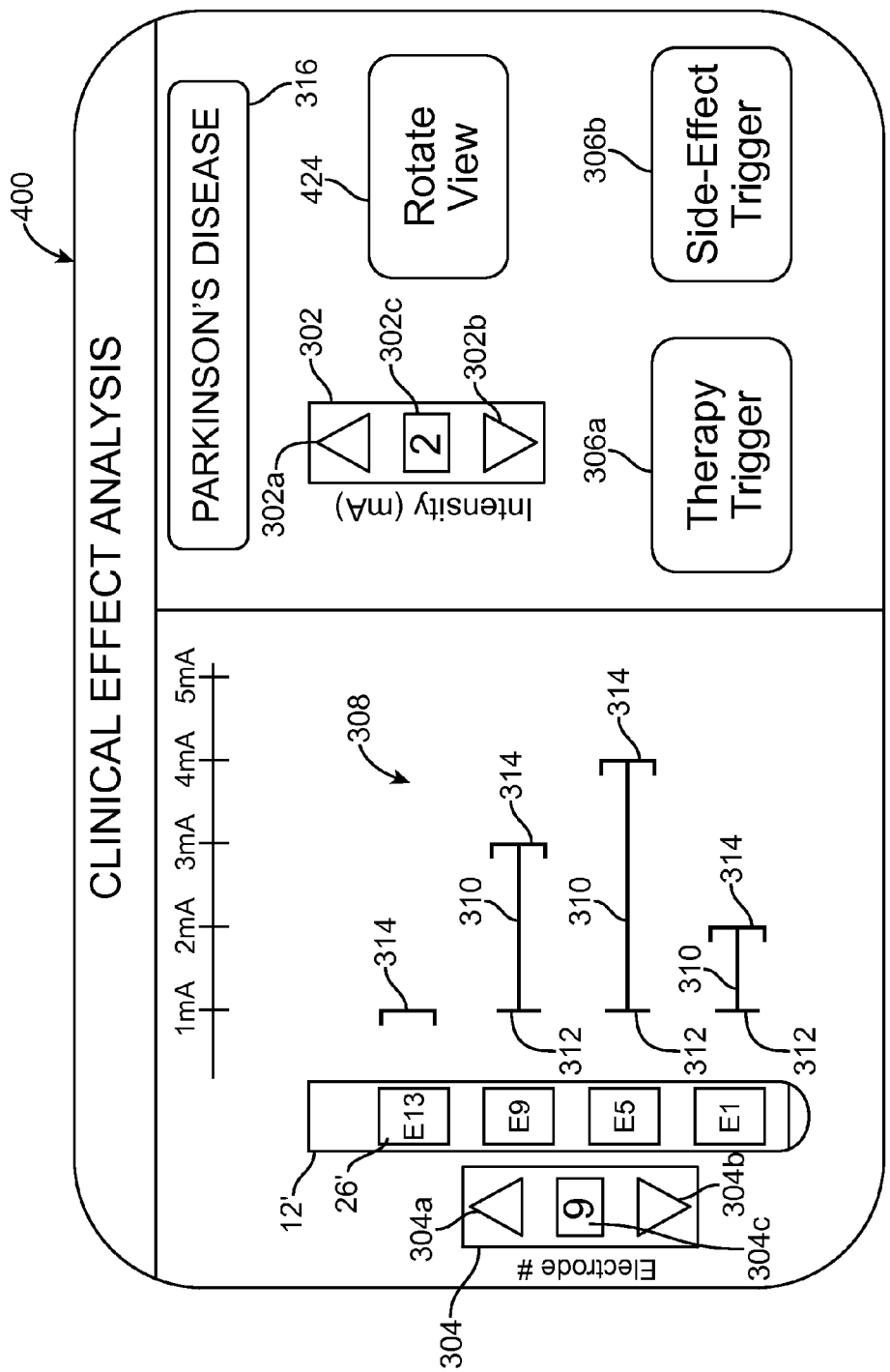
FIGS. 15a-15d are plan views of another embodiment of a clinical effects analysis screen that can be generated by the CP of FIG. 8.
Figure 15B:
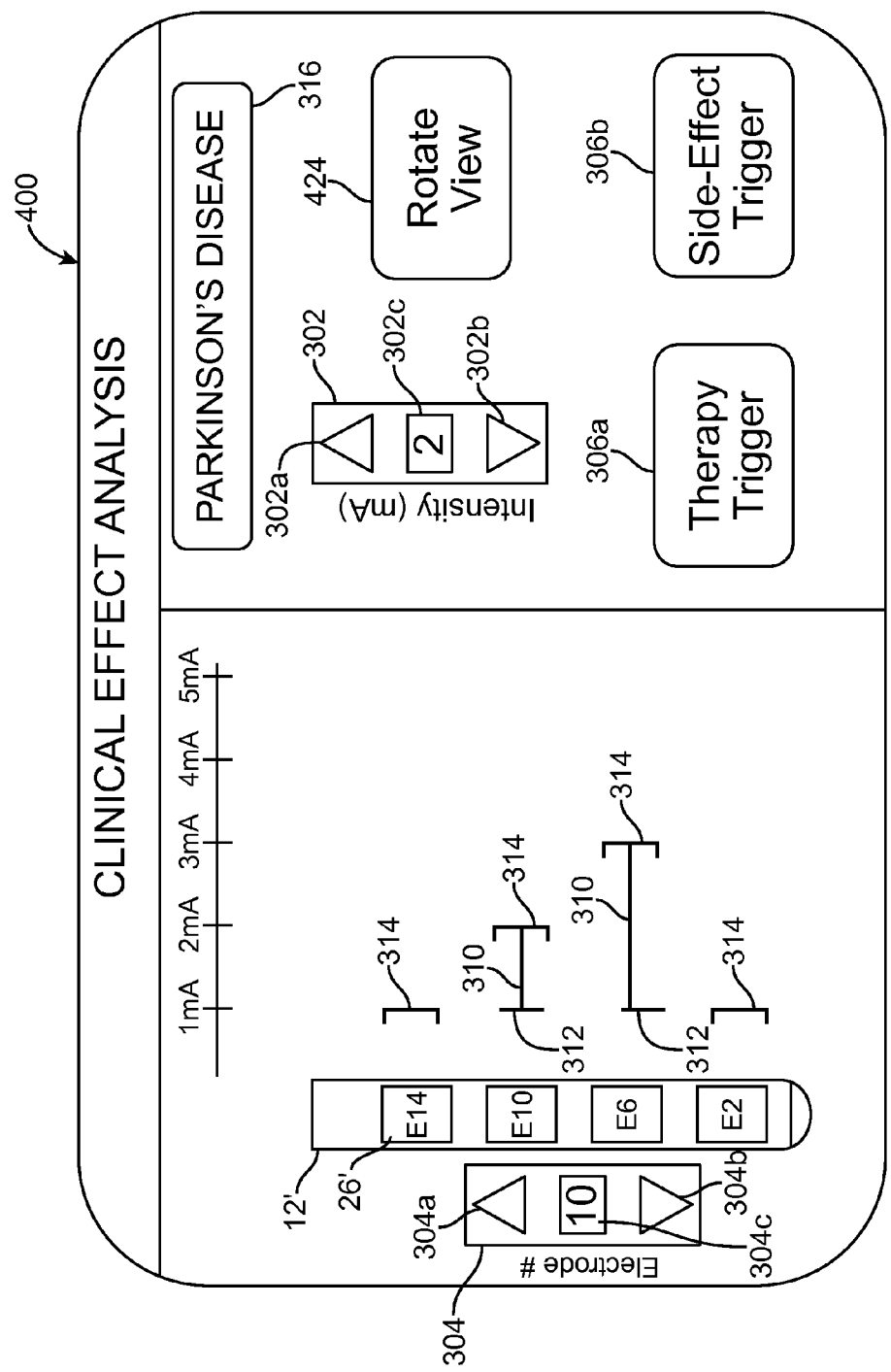
Figure 15C:
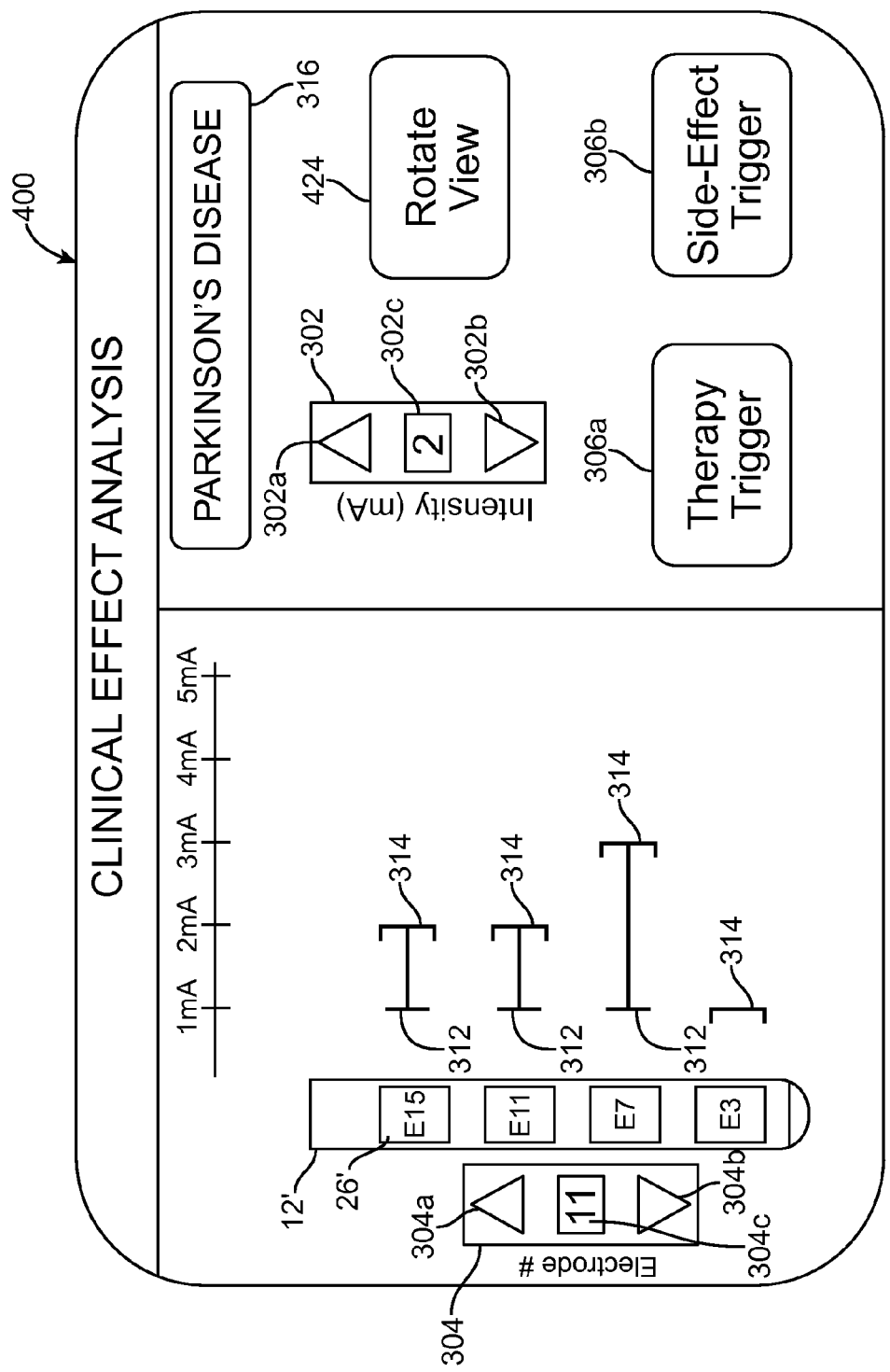
Figure 15D:
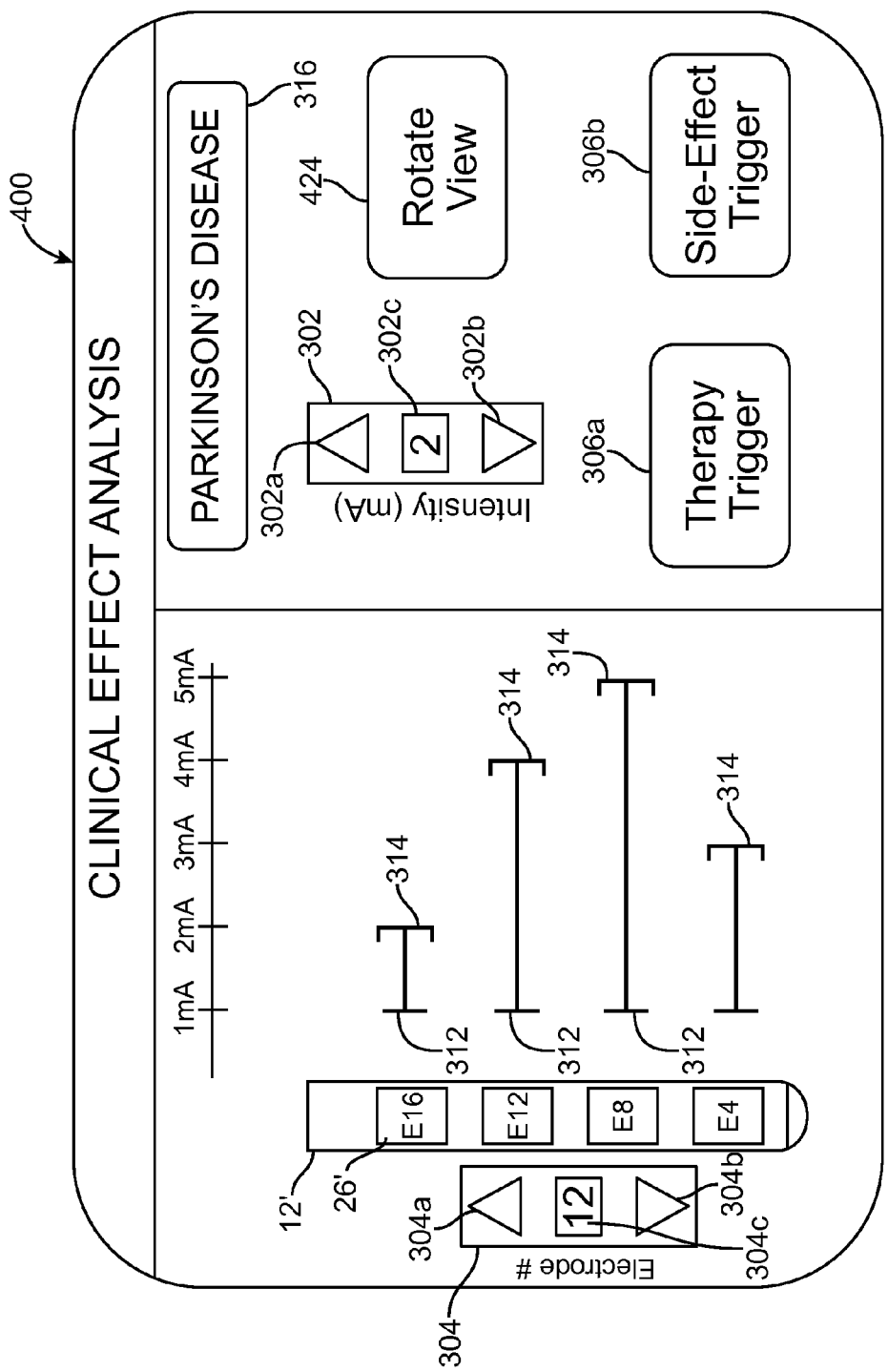

In an optional embodiment, the bar map 308 is used by the CP 18 to define and display a target tissue region for stimulation. In particular, as shown in FIG. 13, the CP 18 may automatically define a line 318(1) that connects relevant points 320 within the bars 310 of the bar map 308. In the illustrated embodiment, these points 320 are located halfway between the initial intensity levels of the therapeutic effects (to the extent that there is a therapeutic intensity level) and the side-effect ticks 314 indicated in the respective bars 310 of the bar map 308.

Figure 14:
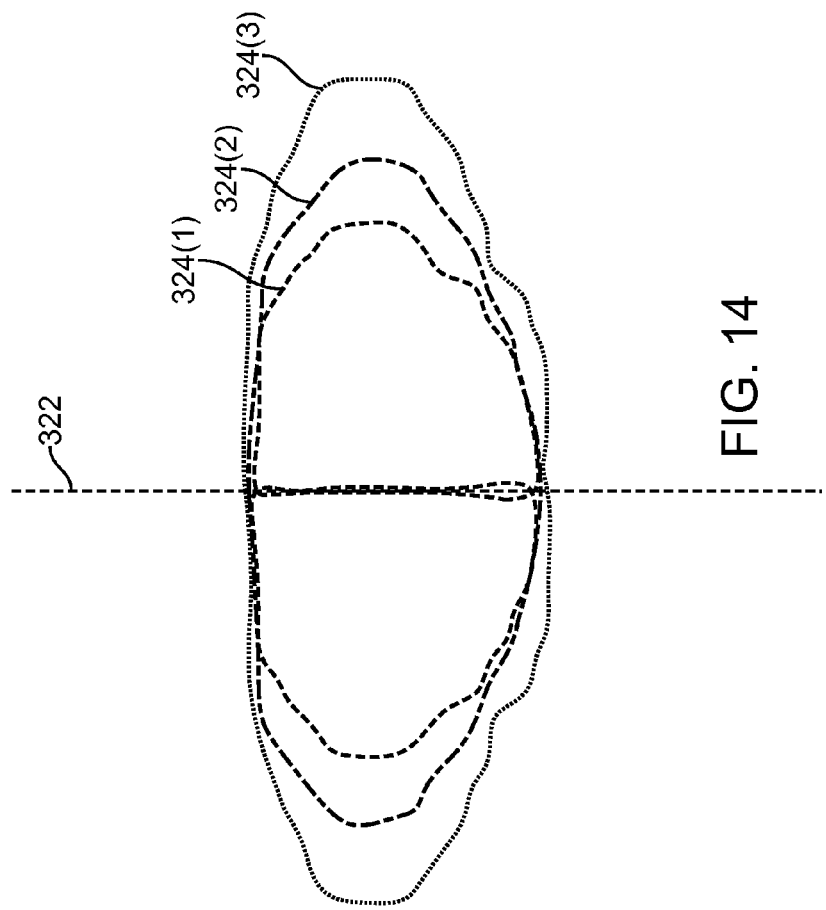
FIG. 14 is a plan view of a method used by the CP of FIG. 8 to generate the entire target tissue region from the one-half target tissue region generated in FIG. 13.

The CP 18 may then smooth the line 318(1) and revolve it around a vertical axis 322 defined by the electrodes to create a bi-laterally symmetrical target tissue region 324(1), as shown in FIG. 14, which can be displayed to the user to aid in programming the IPG 14. In the case, where a three-dimensional target tissue region is generated and displayed, the line 318(1) is revolved around the vertical axis 322 of the electrodes to define a three-dimensional volume. Although the target tissue region 324 may not identically match the therapy regions TH1, TH2 illustrated in FIG. 11, it still provides a suitable visual guide for the user to facilitate the programming of the IPG 14 with one or more effective electrode combinations.

In alternative embodiments, the connecting points 320 may be located at other locations in the bar map 308, such as, e.g., at the end of the bars 310 (i.e., at the highest intensity levels of the therapeutic effect) or three-quarters between the initial intensity levels of the therapeutic effects (to the extent that there is a therapeutic intensity level) and the side-effect ticks 314 indicated in the respective bars 310 of the bar map 308. In these cases, the CP 18 may automatically define line 318(2) and 318(2) that connect the relevant points 320 within the bars 310 of the bar map 308, smooth the lines 318(2) and 318(3), and revolve them around the vertical axis 322 defined by the electrodes to respectively create bi-laterally symmetrical target tissue regions 324(2) and 324(3), as shown in FIG. 14.

Notably, the line 318(1) and the corresponding target tissue region 324(1) provides the least aggressive therapy (e.g., when the patient is asleep), the line 318(2) and the corresponding target tissue region 324(2) provides moderately aggressive therapy (e.g., when the patient is talking), and the line 318(3) and the corresponding target tissue region 324(3) provides the most aggressive therapy (e.g., when the patient is walking). A control (not shown) can be provided, which can be actuated by the user to select a "low" setting that prompts the CP 18 to create target tissue regions having the least aggressive therapy, a "medium" setting that prompts the CP 18 to create target tissue regions having a moderately aggressive therapy, and a "high" setting that prompts the CP 18 to create target tissue regions having the most aggressive therapy.

Although the previous embodiment has been described in the context of a neurostimulation lead 12 having ring electrodes 26 (e.g., the neurostimulation lead 12 illustrated in FIG. 2), a neurostimulation lead 12 having segmented electrodes 26 can be used (e.g., the neurostimulation lead 12 illustrated in FIG. 3).

For example, referring to FIGS. 15a-15d, a clinical effect analysis screen 400 allows a user to readily determine the extent to which each of the different electrode combinations influences the clinical effects. The clinical effect analysis screen 400 is similar to the clinical effect analysis screen 300 illustrated in FIG. 12, with the exception that a bar map 308 is generated and displayed for the electrode segments 26 on one side of the neurostimulation lead 12 (i.e., a first bar map 308a for electrodes E1, E5, E9, and E13 (FIG. 15a); a second bar map 308b for electrodes E2, E6, E10, and E14 (FIG. 15b); a third bar map 308c for electrodes E3, E7, E11, and E15 (FIG. 15c); and a fourth bar map 308d for electrodes E4, E8, E12, and E16 (FIG. 15d)). In the same manner discussed above with respect to the clinical effect analysis screen 300, the intensity level of the electrical stimulation energy conveyed through each electrode can be incrementally increased using the intensity level adjustment control 302, and the clinical information can be gathered via the clinical effect trigger buttons 306, such that the bar maps 308 can be generated. However, the clinical effect analysis screen 400 includes a view rotation button 424 that rotates the view of the electrodes 26 and corresponding bar map 308 in a carousel-like fashion. In an optional embodiment where the generation and display of a target tissue region is desired, the CP 18, for each bar map 308, may define a line that connects relevant points within the bars 310, such that a total of four lines spaced 90 degrees from each other are defined. In this case, the CP 18 may conform a three-dimensional surface to the lines to create a three-dimensional target tissue region.

As briefly discussed above, instead of entering clinical information indicating whether or not a therapeutic effect or side-effect has been perceived by the patient, as score can be assigned to a therapeutic effect or even a side-effect to allow the CP 18 to better quantify the clinical effects. The use of scores to aid in determining clinical effects is particularly useful when multiple disorders are being treated for the patient.

Figure 16:
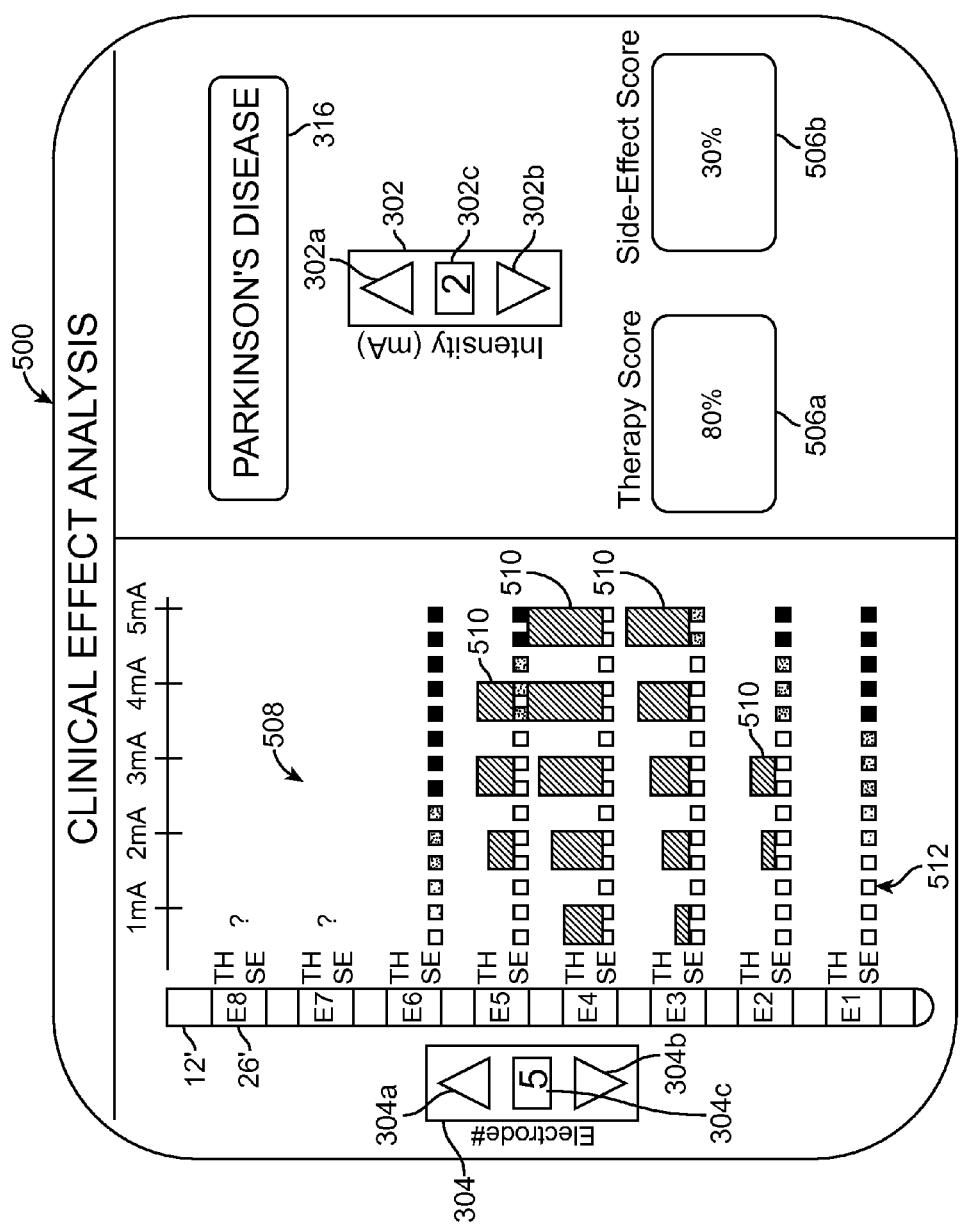
FIG. 16 is a plan view of still another embodiment of a clinical effects analysis screen that can be generated by the CP of FIG. 8.

For example, referring to FIG. 16, a clinical effect analysis screen 500 is similar to the clinical effect analysis screen 300 described above, with the exception that, instead of having clinical trigger buttons 306 that allow the user to enter when a therapeutic effect or side-effect is perceived, this screen includes score entry boxes 506, and in particular, a therapeutic score box 506a and a side-effect score box 506b, that allows the user to enter scores for the therapeutic effect or side-effect. Thus, for each incremental intensity level of the electrical stimulation energy conveyed via the currently selected electrode, the user may enter a score for a therapeutic effect (if any) in the therapeutic score box 506a, and a score for a side-effect (if any) in the side-effect score box 506b.

Of course, a different means for entering scores into the CP 18 and displaying the scores to the user other than text entry boxes can be used, controls similar to the intensity level adjustment control 302 and electrode selection control 304. Whereas the user preferably incrementally increased the intensity level of the stimulation energy via the intensity level adjustment control 302 until a side-effect was perceived (i.e., up until the perception threshold of the side-effect is met or exceeded) in the clinical effects analysis screen 300 above, when using the clinical effect analysis screen 500, as long as a therapeutic effect is perceived, the user preferably incrementally increases the intensity level of the stimulation energy via the intensity level adjustment control 302 until the side-effect is intolerable, so that the side-effect can be fully determined by the CP 18.

The user may enter the score into the therapeutic score box 506a as a relative improvement in a symptom, with 0% representing no improvement in the symptom, and 100% representing total elimination of the symptom as if there were no disease state. In contrast to the clinical effect analysis screen 300 of FIG. 12 where a bar map 308 is generated for each of the disorders, the clinical effect analysis screen 500 generates a composite score from the individual scores corresponding to the respective disorders, so that one bar map is generated for the multiple disorders. For example, at a particular intensity level for a particular electrode, if a score of 10% is entered for Parkinson's Disease, and a score of 40% is entered for Essential Tremor, the CP 18 will determine the composite score to be 25%. In an optional embodiment, the disorders may be weighted, such that the scores for one disorder affect the composite score more than the scores for another disorder. For example, if Parkinson's Disease is weighted twice as much as Essential Tremor, the composite score in the exemplary case may be 35% instead of 25%. If multiple side-effects are perceived by the patient, the user may enter the worst-case score into the side-effect score box 506b. For example, if two side-effects are experienced by the patient (e.g., nausea and slurred speech), and one side-effect is really bad, whereas the other side-effect is minimal, the score for the one side-effect can be entered into the side-effect score box 506b, whereas the score for the other side-effect can be ignored. In an alternative embodiment, a general wellness score box (not shown) can be used to enter a wellness score that takes into account the therapeutic effect and side-effect resulting from the electrical stimulation energy at each incremental intensity level.

In this embodiment, the CP 18 graphically generates and displays this information in the form of bar map 508 for the electrodes E1-E8. The bar map 508 includes a sets of vertical bars 510, each set being displayed on a line "Th" next to the electrode that is currently selected for testing. Each of the vertical bars 510 indicates the relative level (in this case, a score) of the therapeutic effect at each incremental intensity level for each of the electrodes E1-E8. The height of each vertical bar 510 is proportional to the score that it indicates, such that as the score increases, the height of the corresponding vertical bar 510 increases. In the case where there is no therapeutic effect at an incremental intensity level, no bar is generated and displayed.

The bar map 508 also includes horizontal bars 512, each of which is displayed on a line "SE" next to the electrode that is currently selected for testing. Each of the horizontal bars 512 is graduated with different shades to indicate the relative level (in this case, a score) of the side-effect at the incremental intensity levels for each of the electrodes E1-E8. The darkness of the shades in each of the horizontal bars 510 is proportion to the score that it indicates, such that as the score increases, the shade becomes darker. Thus, the beginning of where the shading in the horizontal bar 510 appears indicates the beginning of the side-effect (i.e., when the side-effect is initially perceived), which increases in darkness, with a black shading indicating that the side-effect has become intolerable. In this case where there is no side-effect at an incremental intensity level, no shade is displayed. In an optional embodiment, the bar map 508 further includes an intolerable side-effect indicator (not shown) that can be generated and displayed at the respective incremental intensity level that it is perceived. To this end, the clinical effect analysis screen 500 may include a trigger button (not shown) that can be actuated by the user to indicate when a side-effect is intolerable to the patient.

Notably, because the pulse width and pulse rate of stimulation energy used to treat different disorders will differ from each other, the user will typically test all of the electrodes for one disorder before testing all of the electrodes for another disorder. For example, after testing all of the relevant electrodes and entering the clinical information for one disorder, the user can return to the therapy selection screen 200, select another disorder via the disorder boxes 202, and then go to the clinical effects analysis screen 500 to test the relevant electrodes and enter the clinical information for the other disorder.

In the example illustrated in FIG. 16, and with further reference to FIG. 11, no vertical bar 510 and a moderate intensity shading for the horizontal bar 512 is displayed adjacent electrode E1, indicating to the user that electrode E1 highly influences a side-effect region without influencing a therapeutic effect at all, which corresponds to electrode E1 being partially contained in the first side-effect region SE1. The highest score vertical bar 510 displayed adjacent electrode E2 is 40%; however, the side-effect is initially perceived before that vertical bar 510, indicating to the user that electrode E2 somewhat influences a therapeutic effect and a side-effect, which corresponds to electrode E2 being between the first therapy region TH1 and the first side-effect region SE1. The highest score vertical bar 510 displayed adjacent electrode E3 is 80%, with the side-effect being initially perceived after this vertical bar 510, indicating that electrode E3 highly influences a therapeutic effect, which corresponds to electrode E3 being fully within the first therapy region TH1. The highest score vertical bar 510 displayed adjacent electrode E4 is 100%, with the side-effect never being perceived at all, indicating that electrode E4 highly influences a therapeutic effect, which corresponds to electrode E4 being in the center of the first therapy region TH1. The highest score vertical bar 510 displayed adjacent electrode E5 is 40%; however, the side-effect is initially perceived before that vertical bar 510, indicating to the user that electrode E5 somewhat influences a therapeutic effect and a side-effect, which corresponds with electrode E5 being partially contained in the first and second therapy regions TH1, TH2, and near the second side-effect region SE2. No vertical bar 510 and a moderate intensity shading for the horizontal bar 512 is displayed adjacent electrode E6, indicating to the user that electrode E6 highly influences a side-effect region without influencing a therapeutic effect at all, which corresponds to electrode E6 being contained in the second side-effect region SE1. The question marks adjacent electrodes E7 and E8 have not been tested, presumably by choice of the user based on the fact that the therapeutic effect diminished at electrode E6.

Figure 18:
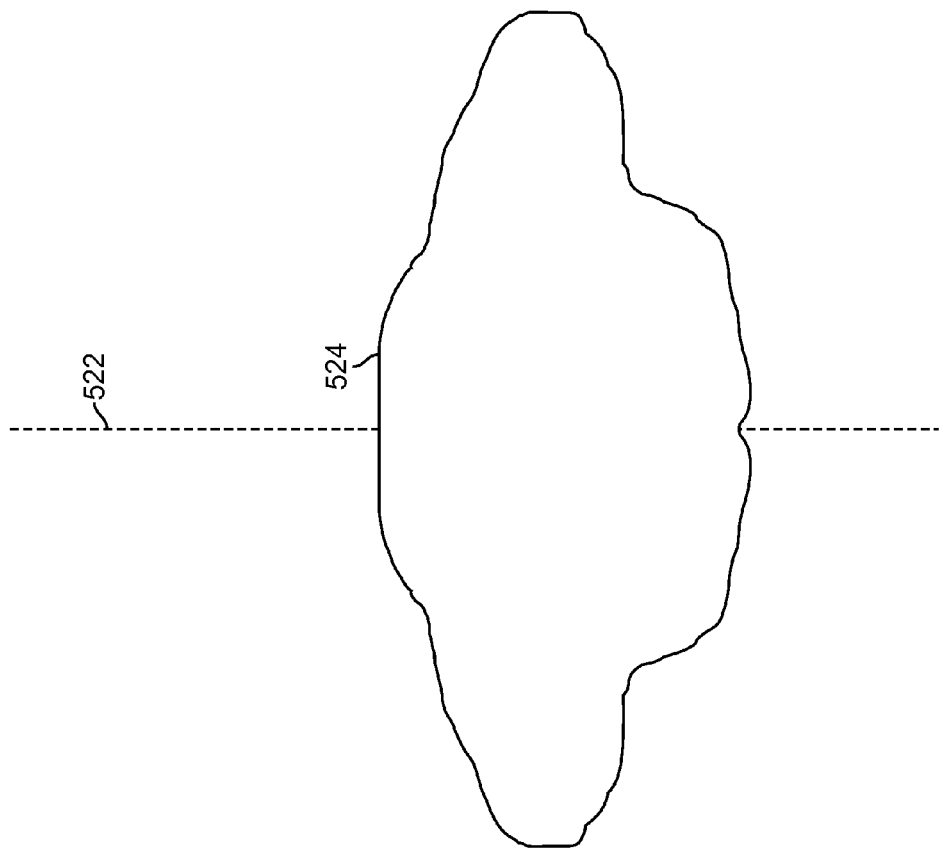
FIG. 18 is a plan view of a method used by the CP of FIG. 8 to generate the entire target tissue region from the one-half target tissue region generated in FIG. 17.
Figure 17:
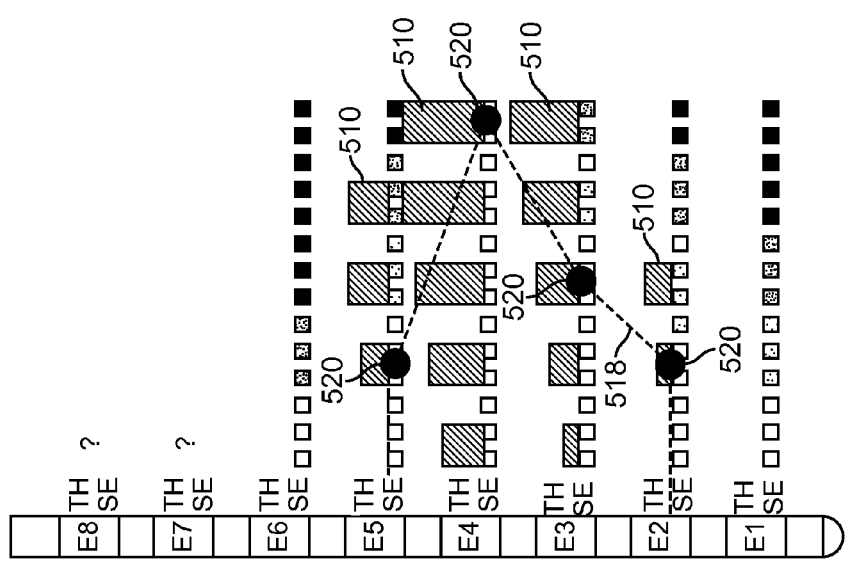
FIG. 17 is a plan view of a method used by the CP of FIG. 8 to determine one-half of a target tissue region from a bar map generated in the clinical effects analysis screen of FIG. 16.

In an optional embodiment, the bar map 508 is used by the CP 18 to define and display a target tissue region for stimulation. In particular, as shown in FIG. 17, the CP 18 may automatically define a line 518 that connects relevant points 520 within the bar map 508. In the illustrated embodiment, each of the points 520 are located in the gap between the incremental intensity level corresponding to the highest score vertical bar 510 and the incremental intensity level at which a side-effect is initially perceived for the respective electrode. The CP 18 may then smooth the line 518 and revolve it around a vertical axis 522 defined by the electrodes to create a bi-laterally symmetrical target tissue region 524, as shown in FIG. 18, which can be displayed to the user to aid in programming the IPG 14. In the case, where a three-dimensional target tissue region is generated and displayed, the line 518 is revolved around the vertical axis of the electrodes to define a three-dimensional volume.

In alternative embodiments, the connecting points 520 may be located at other locations in the bar map 508, such as, e.g., at the incremental intensity levels corresponding to the highest score vertical bars 510, at a point halfway between the incremental intensity level corresponding to the highest score vertical bar 510 and the incremental intensity level at which an intolerable side-effect is perceived for the respective electrode. In the same manner as discussed above with respect to FIGS. 13 and 14, a range of differently aggressive target tissue regions 524 may be created with the different lines 518.

Figure 19:
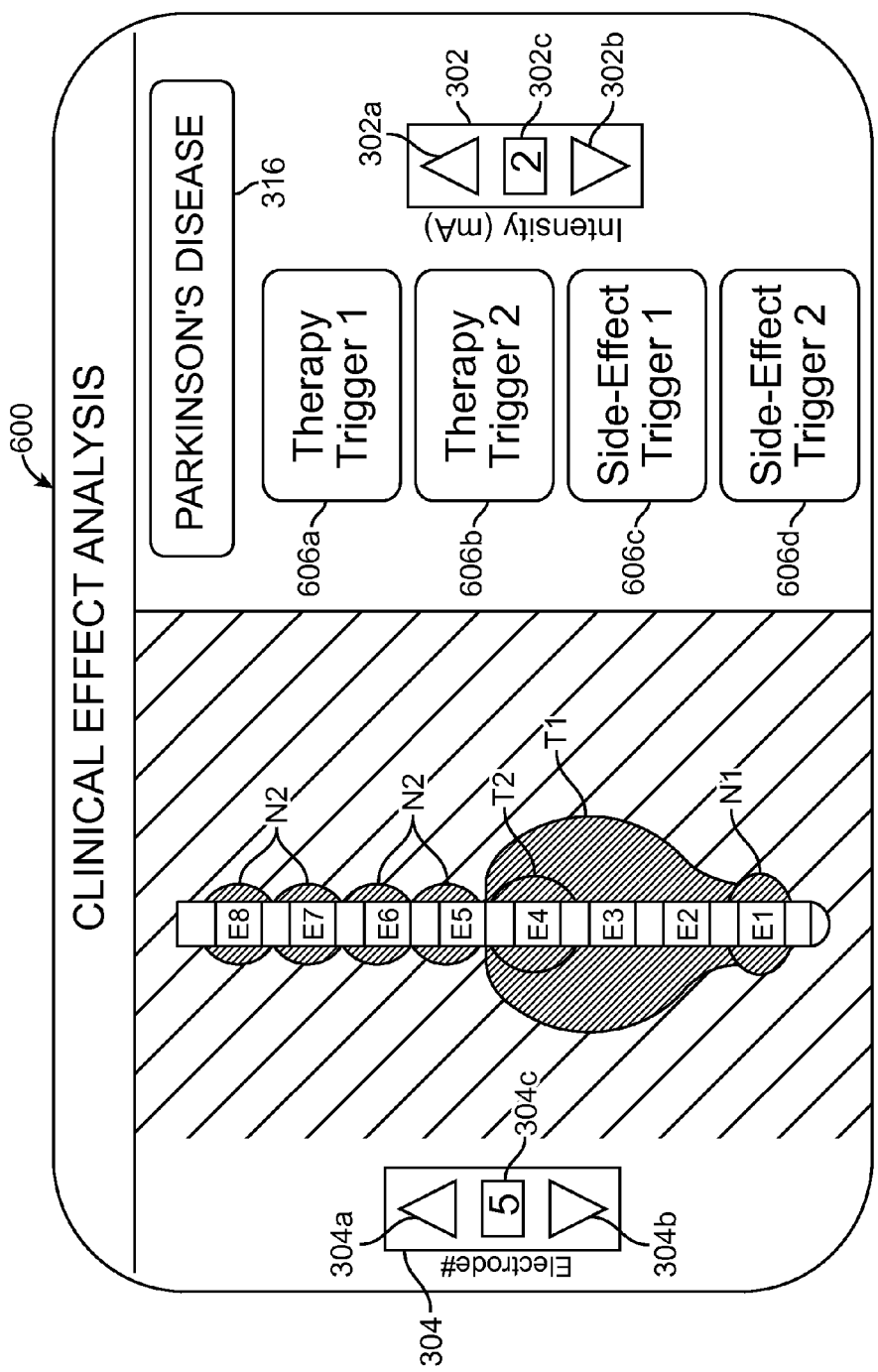
FIG. 19 is a plan view of yet another embodiment of a clinical effects analysis screen that can be generated by the CP of FIG. 8.

Referring to FIG. 19, a clinical effect analysis screen 600 is similar to the clinical effect analysis screen 300 described above, with the exception that the CP 18 generates a volume map 608 instead of a bar map 308. The clinical effect analysis screen 600 also includes a plurality of therapeutic effect trigger buttons (in this case, two therapeutic trigger buttons 606a, 606b) that can be actuated when the patient respectively experiences a plurality of different therapeutic effects, and a plurality of side-effect trigger buttons (in this case, two side-effect trigger buttons 606c, 606d) that can be actuated when the patient respectively experiences a plurality of different side-effects. For example, if the patient experiences one therapeutic effect, the user may actuate the first therapeutic trigger button 606a, and if the patient experiences another different therapeutic effect, the user may actuate the other therapeutic trigger button 606b. Likewise, if the patient experiences one side-effect, the user may actuate the first side-effect trigger button 606c, and if the patient experiences another different side-effect, the user may actuate the other side-effect trigger button 606d.

The different therapeutic effects (and likewise, the different side-effects) can be concurrently experienced by the patient or may be experienced by the patient during different times. In the same manner discussed above with respect to the clinical effect analysis screen 300, the CP 18 quantifies the influence of each electrode 26 on the therapeutic effect by determining the range of incremental intensity levels at which a metric of each of the therapeutic effects occurs based on verbal feedback from the patient, and further determining the incremental intensity level at which a metric of each of the side-effects initially occurs. However, the CP 18 further quantifies the influence of each electrode 26 on the clinical effects by determining the electrodes that most influence the therapeutic effects and the side-effects, and generates the volume map 608 based on this determined clinical information.

The volume map 608 includes one or more target tissue regions (in this case, two target regions T1, T2) displayed adjacent the electrodes that are determined to most influence the therapeutic effects, and one or more non-target tissue regions (in this case, two non-target tissue regions N1, N2) displaced adjacent the electrodes that are determined to most influence the side-effects. In the illustrated embodiment, the regions are illustrates as being two-dimensional, although in other embodiments, the regions can be illustrated as being three-dimensional in nature. The portion of the map 608 that is hatched represents unexplored area, thereby allowing the user to readily determine the portion of the tissue has been explored and the portion of the tissue that has been explored (i.e., either designated as target tissue or non-target tissue). The different target regions T1, T2 and non-target tissue regions N1, N2 may be coded with different colors to enable the user to more easily distinguish the different target regions from each other and the target regions from the non-target regions. For example, the border of the first target tissue region T1 may be colored green, the border of the second target tissue region T2 maybe colored purple, and the borders of the non-target tissue regions N1, N2 may be colored orange. The target tissue regions T1, T2 and non-target tissue regions N1, N2 may also be filled in with different colors.

In one embodiment, the CP 18 estimates the size and shape of the target tissue region based on the highest incremental intensity level of therapeutic effects for each electrode. The CP 18 estimates the size and shape of the non-target tissue regions as being closely surrounding the electrode determined to influence the side-effects corresponding to the non-target tissue regions. Notably, the exact boundaries of the volume or region of tissue influenced by the electrodes may not be initially known (only that the volume or region of tissue is close by). However, the boundaries of the volume or region of tissue influenced by the electrodes may be estimated using an atlas of known target and non-target tissue regions or may be deduced as clinical information is collected by the CP 18 in subsequent stimulation scenario steps. In another embodiment, the CP 18 estimates either an electric field or a region of tissue activation at the highest incremental intensity level at which the therapeutic effects occur for each electrode, and determines the size and shape of the target tissue regions based on this information. Logical operators may be used to estimate each influencing electrode's contribution on the relevant target tissue region.

For example, when electrode E1 is activated at an amplitude high enough to evoke a side-effect, the stimulated region could be modeled and one could deduce that somewhere on the outer boundary of the stimulation field model the excitation has resulted in a side-effect, but not know exactly which part of the stimulation field model boundary is responsible. If electrode E2 is then activated, it may be that at some amplitude where a side effect is not yet reached, a new stimulation field model could be generated that overlaps the stimulation field model generated during the test with electrode E1 (which evoked the side effect). It can now be deduced that the part of the boundary of the stimulation field model from the test of electrode E1 (at side effect threshold) that is overlapping with the stimulation field model with the test of electrode E2 (no side effect) is not responsible for the side effect, and this information can be graphically provided to the user (e.g., change in color, etc. of some part of the clinical effects map). Note that other logical deductions can be performed as more information is gathered, and these deductions can be graphically conveyed to the user.

For example, as shown in FIG. 19 and with further reference to FIG. 11, a relatively small non-target tissue region N1 surrounds electrode E1, indicating to the user that electrode E1 influences a side-effect, which corresponds to electrode E1 being partially contained in the first side-effect region SE1. A relatively large target tissue region T1 surrounds electrodes E2-E5, indicating to the user that electrodes E2-E5 influence a therapeutic effect, with the width of the target tissue region T1 being greatest at electrode E4 and tapering down at electrodes E2, E3, and E5, indicating that electrode E4 highly influences the therapeutic effect. This corresponds with electrode E2 being adjacent the first therapy region TH1, electrode E3 being fully within the first therapy region TH1, electrode E4 being in the center of the first therapy region TH1, and electrode E5 being partially contained in the first therapy region TH1. A relatively small target tissue region T2 surrounds electrodes E4-E5, indicating to the user that electrodes E4 and E5 influence another therapeutic effect, which corresponds to electrode E4 being fully contained within the second therapy region TH2 and electrode E5 being partially contained in the second therapy region TH2. A long scalloped non-target region surrounds electrodes E6-E8, indicating to the user that electrodes E6-E8 influence another side-effect region, which corresponds to electrodes E6-E8 being contained within the second side-effect region SE2.

Figure 20D:
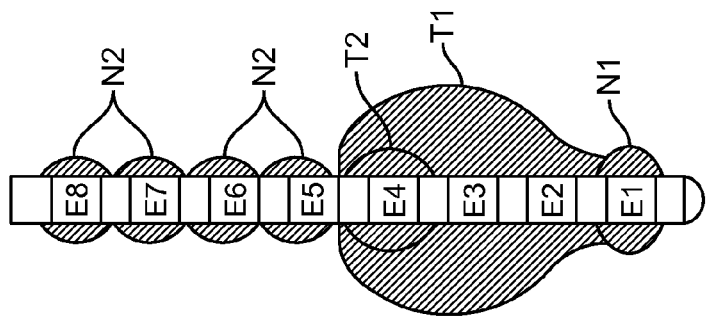
FIGS. 20a-20d are plan views illustrating a series of steps in generating a volume map in the clinical effects analysis screen of FIG. 19.
Figure 20C:
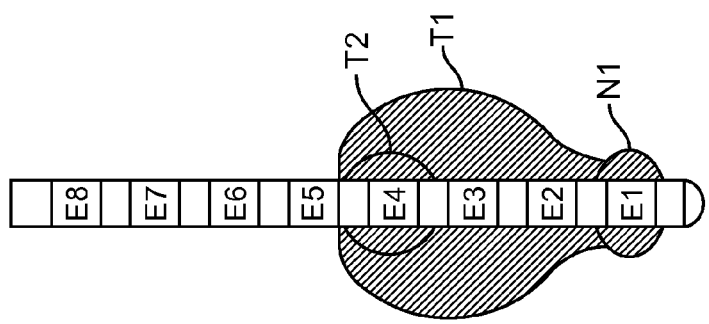
Figure 20B:
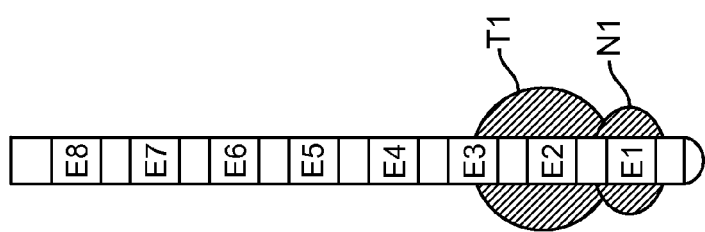
Figure 20A:
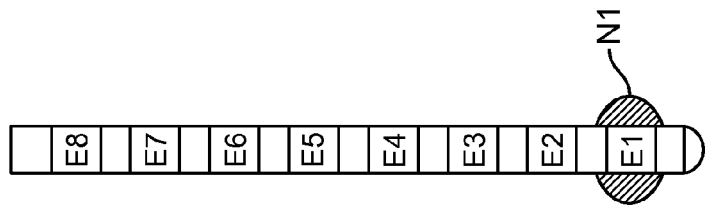

Referring to FIGS. 20a-20d, the CP 18 may generate and display the volume map 608 in a progressive manner as clinical information is entered by the user. For example, after clinical information is entered for electrode E1, the CP 18 may generate and display the first non-target tissue region N1 around electrode E1 (FIG. 20a). After clinical information is entered for electrode E2, the CP 18 may generate and display the first target tissue region T1 around electrode E2 (FIG. 20b). As clinical information is gathered for electrodes E3-E5, the first target tissue region T1 grows larger, and the second target tissue region T2 is added (FIG. 20c). As clinical information is gathered for electrodes E6-E8, the second non-target tissue region N2 is added around these electrodes (FIG. 20d).

In an optional embodiment, instead of having the user manually test each electrode for clinical effects in a methodical manner, the CP 18 may suggest electrodes or electrode combinations that can be subsequently tested by the user to obtain the best clinical information. For example, referring to FIG. 30, an optimization algorithm can be used to estimate the best electrode configuration that provides the best therapeutic stimulation. The user may enter the position of the neurostimulation lead or leads into the CP 18 (e.g., based on atlas, stereotactic coordinates, user estimate, etc.), and the clinical effects data collected during programming, and the CP 18 may output the optimal electrode configuration, and optionally, the optimum pulse amplitude, pulse width and pulse rate. The optimization algorithm may be an optimization cost function designed with the objective of providing the "best guess" optimal electrode configuration and/or other stimulation parameters. Alternatively, the cost function could be designed to reveal all or a specific part of the clinical effects "map" or explore part of the anatomy. This latter objective could have the purpose of obtaining information that will subsequently inform an estimate of optimal therapeutic stimulation (e.g., the explored data may contribute to refining the lead-to-therapeutic region relationship).

Referring back to FIG. 9, the CP 18 is capable of modifying the anatomical regions of interest (namely, the therapy tissue region 124 and the side-effect tissue region 126), as obtained from the atlas, to be more patient-specific and to correct any mis-registration between the anatomical regions of interest and the neurostimulation lead 12. This is accomplished by conveying electrical stimulation into the tissue of the patient via selected electrodes, thereby creating one or more clinical effects, determining an influence of the specified electrodes on the clinical effects, and modifying the anatomical regions of interest (e.g., by spatially translating the anatomical regions of interest relative to the graphical electrode representation 26' or by changing the shape of the anatomical regions of interest) based on the determined influence of the specified electrodes on the clinical effects.

Figure 21:
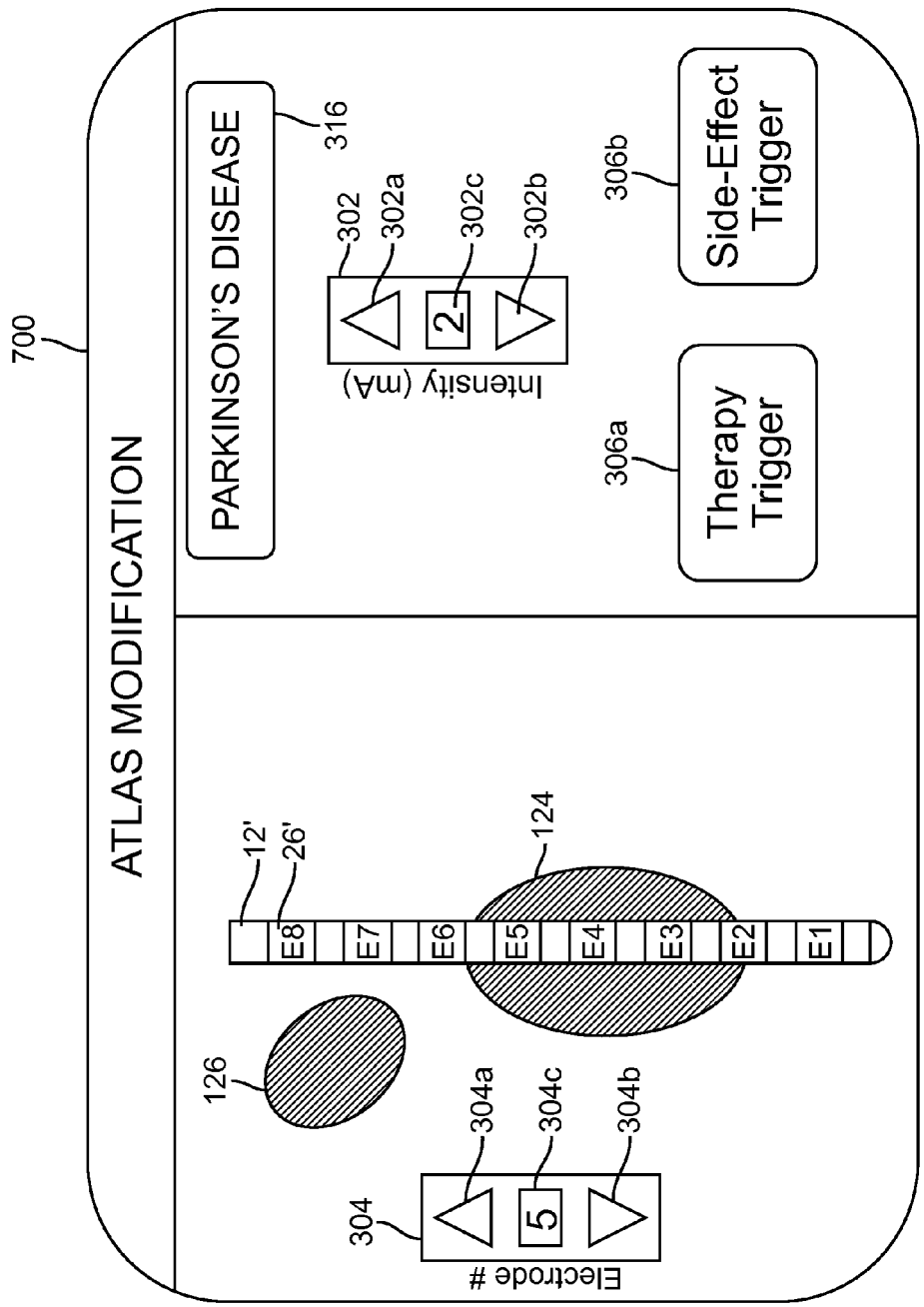
FIG. 21 is a plan view of one embodiment of an atlas modification screen that can be generated by the CP of FIG. 8.

In one embodiment shown in FIG. 21, an atlas modification screen 700 includes the previously described intensity level adjustment control 302, electrode selection control 304, and clinical information entry buttons 306 that can be actuated in the same manner described above with respect to the clinical effect analysis screen 300 to adjust the intensity of the electrical stimulation energy and select the electrode via which the electrical stimulation energy will be conveyed, and to enter clinical information as a result of such conveyed electrical stimulation energy, and in particular, to indicate to the CP 18 the intensity level at which the patient experiences a therapeutic effect or side-effect. The atlas modification screen 700 also includes the graphical representation of the neurostimulation lead 12' and the corresponding electrodes 26', as well as the registered anatomical regions of interest, and in this example, the therapy tissue region 124 and side-effect tissue region 126. Based on clinical information entered by the user in response to conveying electrical stimulation energy via selected ones of the electrodes, the CP 18 may heuristically determine the manner in which the anatomical regions of interest should be modified.

Figure 22B:
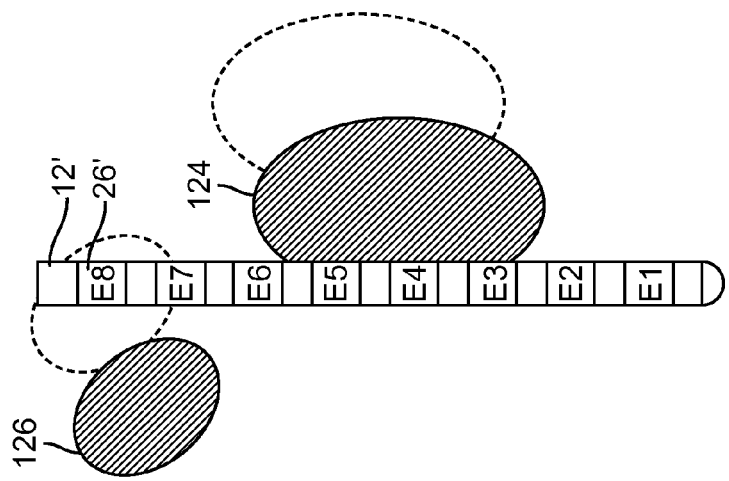
FIGS. 22a-22b are plan views showing an exemplary method used by the CP to modify an atlas via the atlas modification screen of FIG. 21.
Figure 22A:
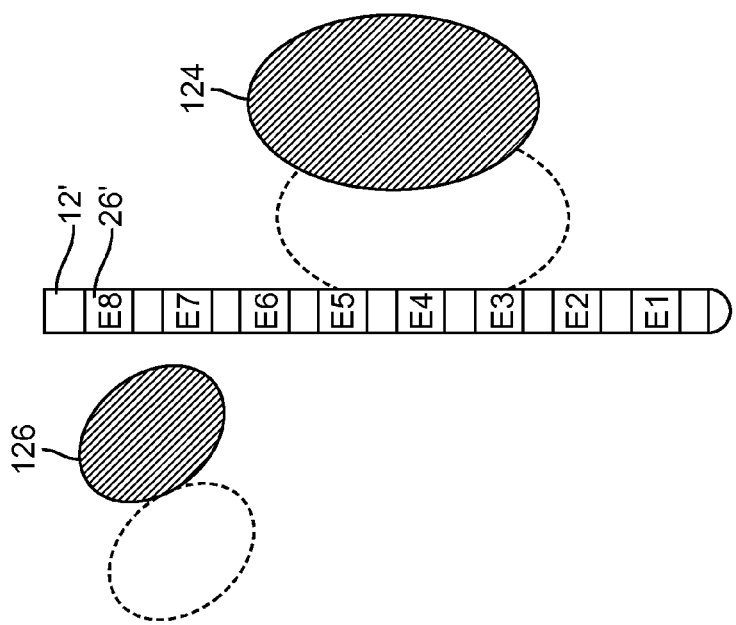

In one embodiment, the CP 18 may determine the proximity between a displayed anatomical region of interest and a specified electrode in the graphical electrode representation 26'. The determined proximity may simply be a rough estimate, such as, e.g., a relatively large proximity or a relatively small proximity. For example, as shown in FIG. 22a, the proximity between the displayed therapy tissue region 124 and electrode E3 may be determined to be relatively large. In another example, as shown in FIG. 22b, the proximity between the displayed therapy tissue region 124 and electrode E3 may be determined to be relatively small.

The CP 18 may then imply an actual proximity between the displayed anatomical region of interest and the specified electrode based on the determined influence of the specified electrode on the clinical effects. For example, electrode E3 can be selected for conveying the electrical stimulation energy via the electrode selection control 304, and the intensity of the conveyed electrical stimulation energy can be incrementally increased via the intensity adjustment control 302 until a therapeutic effect is perceived by the patient. If the intensity level at which the therapeutic effect is initially perceived is relatively low, the CP 18 may determine the actual proximity between the therapy tissue region 124 and electrode E3 to be relatively small, and if the intensity level at which the therapeutic effect is initially perceived is relatively high, the CP 18 may determine the actual proximity between the therapy tissue region 124 and electrode E3 to be relatively large.

The CP 18 may then spatially translate the displayed anatomical region of interest relative to the specified electrode in the graphical electrode representation 26' to better match the displayed proximity to the actual proximity. This can be accomplished by moving either the displayed anatomical region of interest within the screen 700 or moving the graphical electrode representation 26' within the screen 700, such that there is a relative displacement between the displayed anatomical region of interest and the graphical electrode representation 26'.

For example, in the case where the proximity between the displayed therapy tissue region 124 and electrode E3 is relatively large, as shown in FIG. 22a, the CP 18 may displace the displayed therapy tissue region 124 toward electrode E3 (as shown in phantom) if the actual proximity between the therapy tissue region 124 and electrode E3 is determined to be relatively small. This is because the initial perception of a therapeutic effect at a relatively low intensity level, which indicates that the actual proximity between the therapy tissue region 124 and electrode E3 is relatively small, contradicts the displayed proximity between the therapy tissue region 124 and electrode E3 as being relatively large, and therefore, the displayed therapy tissue region 124 should be moved toward electrode E3 to better match the actual proximity between the therapy tissue region 124 and electrode E3. Assuming that the actual proximity between the therapy tissue region 124 and the side-effect tissue region 126 are the same, the displayed side-effect tissue region 126 may also be spatially translated away from electrode E3 in the same distance in the same direction that the displayed therapy tissue region 124 is spatially translated away from electrode E3 (as shown in phantom) in order to maintain the spatial relationship between the therapy tissue region 124 and the side-effect tissue region 126.

As another example, in the case where the proximity between the displayed therapy tissue region 124 and electrode E3 is relatively small, as shown in FIG. 22b, the CP 18 may displace the displayed therapy tissue region 124 away from electrode E3 (as shown in phantom) if the actual proximity between the therapy tissue region 124 and electrode E3 is determined to be relatively large. This is because the initial perception of a therapeutic effect at a relatively high intensity level, which indicates that the actual proximity between the therapy tissue region 124 and electrode E3 is relatively large, contradicts the displayed proximity between the therapy tissue region 124 and electrode E3 as being relatively small, and therefore, the displayed therapy tissue region 124 should be moved away from electrode E3 to better match the actual proximity between the therapy tissue region 124 and electrode E3. Assuming that the actual proximity between the therapy tissue region 124 and the side-effect tissue region 126 are the same, the displayed side-effect tissue region 126 may also be spatially translated away from electrode E3 the same direction in the same direction that the displayed therapy tissue region 124 is spatially translated away from electrode E3 (as shown in phantom) in order to maintain the spatial relationship between the therapy tissue region 124 and the side-effect tissue region 126.

The CP 18 may displace the displayed side-effect tissue region 126 relative to electrode E3 or any other specified electrode using the same technique described above to displace the therapeutic tissue region 126 relative to electrode E3.

In another embodiment, the CP 18 may determine a relative influence of a specified electrode on a therapeutic effect and a side-effect, and spatially translate or rotate the displayed anatomical region of interest relative to the specified electrode in the graphical electrode representation 26' based on the determined relative influence of the specified electrode on the therapeutic effect and the side-effect.

Figure 23B:
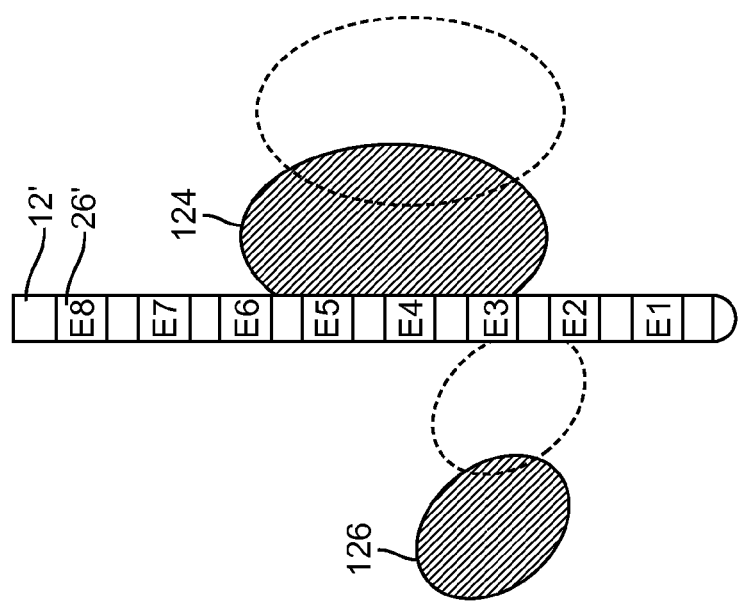
FIGS. 23a-23b are plan views showing another exemplary method used by the CP to modify an atlas via the atlas modification screen of FIG. 21.
Figure 23A:
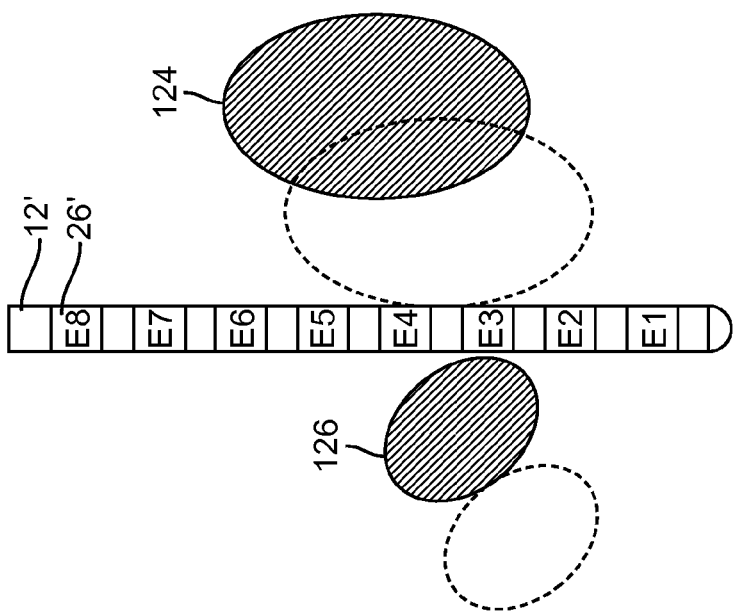

As one example, in the case where the proximity between the displayed therapy tissue region 124 and electrode E3 is relatively large, and the proximity between the displayed side-effect region 124 and electrode E3 is relatively small, as shown in FIG. 23a, electrode E3 can be selected for conveying the electrical stimulation energy via the electrode selection control 304, and the intensity of the conveyed electrical stimulation energy can be incrementally increased via the intensity adjustment control 302 until a clinical effect is perceived by the patient. If a therapeutic effect is entered by the user as the first clinical effect that is perceived by the patient, the CP 18 may spatially translate the displayed therapy tissue region 124 toward electrode E3, and spatially translate the displayed side-effect tissue region 126 away from electrode E3 (as shown in phantom). That is, because the initial perception of a therapeutic effect contradicts the display of electrode E3 closer to the side-effect tissue region 126 than the therapy tissue region 124, it is determined that electrode E3 is actually closer to the therapy tissue region 124 than the side-effect tissue region 126, and therefore, the displayed therapy tissue region 124 should be moved toward electrode E3, and the displayed side-effect tissue region 126 should be moved away from electrode E3.

As one example, in the case where the proximity between the displayed therapy tissue region 124 and electrode E3 is relatively small, and the proximity between the displayed side-effect region 124 and electrode E3 is relatively large, as shown in FIG. 23b, electrode E3 can be selected for conveying the electrical stimulation energy via the electrode selection control 304, and the intensity of the conveyed electrical stimulation energy can be incrementally increased via the intensity adjustment control 302 until a clinical effect is perceived by the patient. If a side-effect is entered by the user as the first clinical effect that is perceived by the patient, the CP 18 may spatially translate the displayed therapy tissue region 124 away from electrode E3 and spatially translate the displayed side-effect tissue region 126 toward electrode E3 (as shown in phantom). That is, because the initial perception of a side-effect contradicts the display of electrode E3 closer to the therapy tissue region 124 than the side-effect tissue region 126, it is determined that electrode E3 is actually closer to the side-effect region 126 than the therapy tissue region 124, and therefore, the displayed therapy tissue region 124 should be moved away from electrode E3, and the displayed side-effect tissue region 126 should be moved toward electrode E3.

Figure 24:
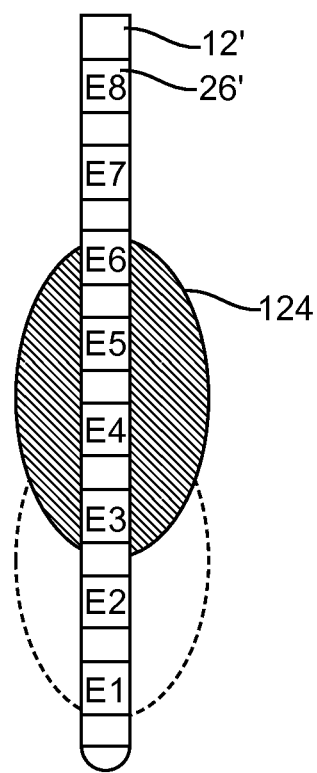
FIG. 24 is a plan view showing still another exemplary method used by the CP to modify an atlas via the atlas modification screen of FIG. 21.
Figure 25:
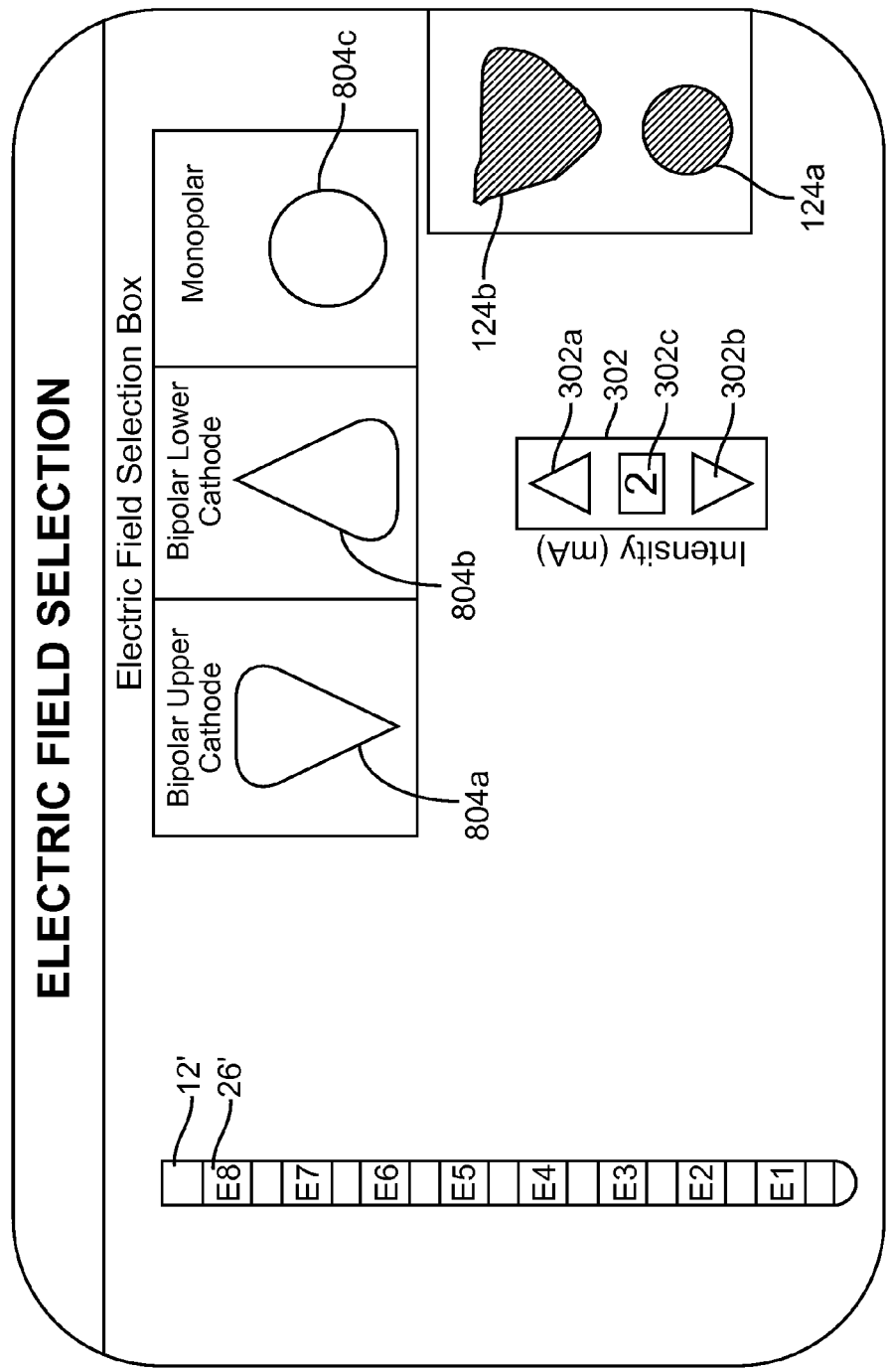
FIG. 25 is a plan view of one embodiment of an electric field selection screen that can be generated by the CP of FIG. 8.

In another embodiment, two different electrodes are selected via the electrode selection control 304. The electrodes are selected, such that one of the electrodes is further away from the displayed anatomical region of interest than the other electrode in the graphical electrode representation 26'. For example, electrodes E2 and E4 can be selected, with electrode E2 being further away than electrode E4 from the displayed therapy tissue region 124, as shown in FIG. 24. The intensity of the electrical stimulation conveyed via the two different electrodes is adjusted via the intensity level adjustment control 302, such that the CP 18 may quantify an influence of each of electrodes E2 and E4 on a therapeutic effect.

For example, the intensity of the electrical stimulation energy conveyed via electrode E2 can be incrementally increased via the intensity adjustment control 302 until a therapeutic effect is perceived by the patient, and then the intensity of the electrical stimulation energy conveyed via electrode E4 can be incrementally increased via the intensity adjustment control 302 until a therapeutic effect is perceived by the patient. If the intensity level at which the therapeutic effect is initially perceived for electrode E2 is lower than the intensity level at which the therapeutic effect is initially perceived for electrode E4 (i.e., electrode E2 has a higher influence than electrode E4 on the therapeutic effect), the CP 18 spatially translate the displayed therapeutic tissue region 124 away from electrode E4 and towards electrodes E2 in the graphical electrode representation 26'. That is, because the intensity levels at which the therapeutic effect for electrodes E2 and E4 contradict the display of electrode E2 being further than electrode E4 from the therapy tissue region 124, it is determined that electrode E2 is actually closer than electrode E4 to the therapy tissue region 124, and therefore, the displayed therapy tissue region 124 should be toward electrode E2 and away from electrode E4.

In still another embodiment, the CP 18 may change the shape of, warp, or morph an anatomical region of interest based on the clinical information entered via the clinical effect analysis screens 300, 400, 500, or 600 discussed above. For example, electrical stimulation energy may be serially conveyed via different ones of the electrodes E1-E8, and for each electrode, the intensity level of the conveyed electrical stimulation energy may be incrementally increased. The CP 18 may quantify the therapeutic effect by determining the highest intensity level at which a metric of the therapeutic effect occurs prior to an initial occurrence of a metric of a side-effect, and change the shape of the therapy tissue region based on the determined highest intensity levels for the different electrodes. That is, the higher the intensity level, the larger the therapy region at the respective electrode should be, and the CP 18 will accordingly modify the shape of the displayed therapy tissue region 124.

In one example, the additional clinical effects information could be used by an algorithm (or manually by the user) to refine an atlas and/or the atlas and lead relationship such that a new atlas-to-lead relationship is more consistent with the clinical effects information that has been gathered, based on knowledge or expectations about stimulation of certain anatomical regions resulting in certain known clinical or physiological effects. If algorithm based, the algorithm is likely to include stimulation field models and their overlap or proximity to certain anatomical structures. Note that to get robust congruence of clinical data and the atlas-to-lead relationship, the warping or the morphing of the atlas may require more than translations and rotations, but perhaps also stretching and affine transformations, spline-type transformations, non-uniform rational B-spline transformations, and alternatives or the like.

Although We need to include rotating, warping, morphing, or generally reshaping. One imagines an algorithm that takes into account the imaging data and the clinical effects data, to get an overall best match Referring to FIG. 25, the CP 18 is capable of allowing a user to more easily match an electric field corresponding to a set of stimulation parameters to a desired electric field via an electric field selection screen 800, which allows the user to select for an electric field one of a plurality of different pre-defined shapes stored within memory 82, and define a location of the electric field relative to the graphical electrode representation 26'. To this end, the programming screen 800 includes the intensity level adjustment control 302 that can be actuated in the same manner described above to adjust the intensity of the conveyed electrical stimulation energy. The programming screen 800 also includes a graphical representation of the neurostimulation lead 12' and the corresponding electrodes 26', as well as anatomical regions of interest, and in this example, two therapy tissue regions 124a and 124b, set off from the graphical representation of the neurostimulation lead 12' and corresponding electrodes 26'.

Significantly, the electric field selection screen 800 includes an electric field selection control 802 that allows the user to select pre-defined electric field shapes that can be located relative to the graphical electrode representation 26'. In particular, the electric field selection control 802 displays various graphical shapes 804a-804c that can be dragged and dropped onto the graphical electrode representation 26'. In the illustrated embodiment, the first graphical shape 804a is an upside down pear shape (which emulates a bipolar electric field with the cathode at the top), the second graphical shape 804b is a right-side up pear shape (which emulates a bipolar electric field with the cathode at the bottom), and the third graphical shape 804a is a sphere (which emulates a monopolar electric field). In alternative embodiment, other types of shapes, such as a triangle or oval, may be provided.

Figure 26:
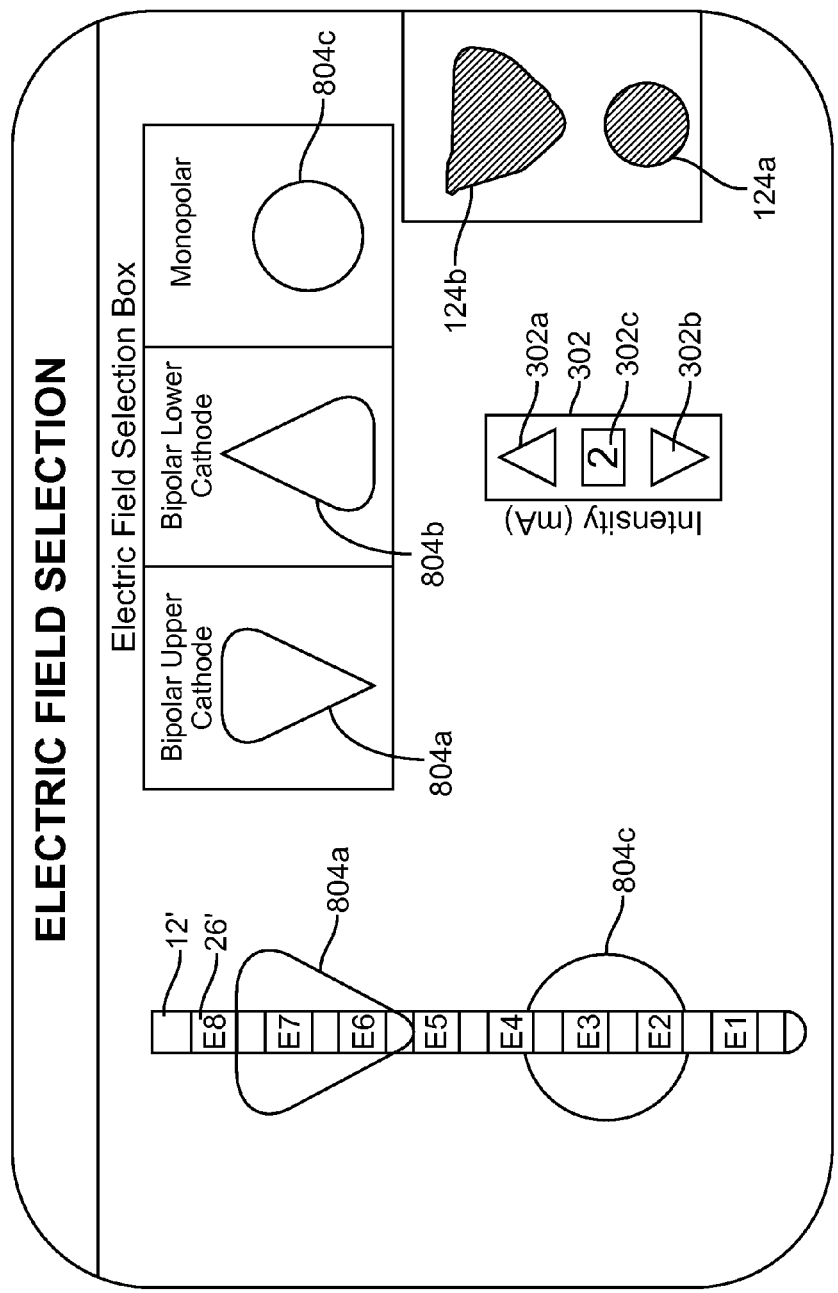
FIG. 26 is a plan view of the electric field selection screen of FIG. 25, particularly illustrating the user selection of two shapes for an electric field.

Preferably, the user compares the pre-defined graphical shapes 804 to the therapeutic tissue region 124, and selects the graphical shape 804 that best matches the shape of the therapeutic region 124. The user preferably locates the selected shape 804 to match the location of the therapeutic tissue region 124 relative to the graphical electrode representation 26'. In an optional embodiment, the CP 18 will automatically locate the user-selected graphical shape 804 to match the location of the therapeutic tissue region 124. Notably, as shown in FIG. 26, multiple graphical shapes 804 can be selected, dragged, and dropped onto the graphical electrode representation 26'. The selected graphical shapes 804 may either be different from each other, as illustrated in FIG. 26, or may be identical to each other. In either case, the CP 18 will prevent the multiple graphical shapes 804 from intersecting each other if the user attempts to move one of the selected graphical shapes 804 into another selected graphical shape 804.

The manner in which a graphical shape 804 is selected, dragged, and dropped will depend on the nature of the user interface. For example, if the display screen 76 is conventional, a virtual pointing device (e.g., cursor controlled by the mouse 72, joy stick, trackball, etc.) can be used to select, drag, and drop the graphical shape 804 onto the graphical electrode representation 26'. If the display screen 76 is a digitizer screen, a physical pointing device (e.g., a stylus or finger) can be used to select, drag, and drop the graphical shape 804 onto the graphical electrode representation 26'.

Figure 27:
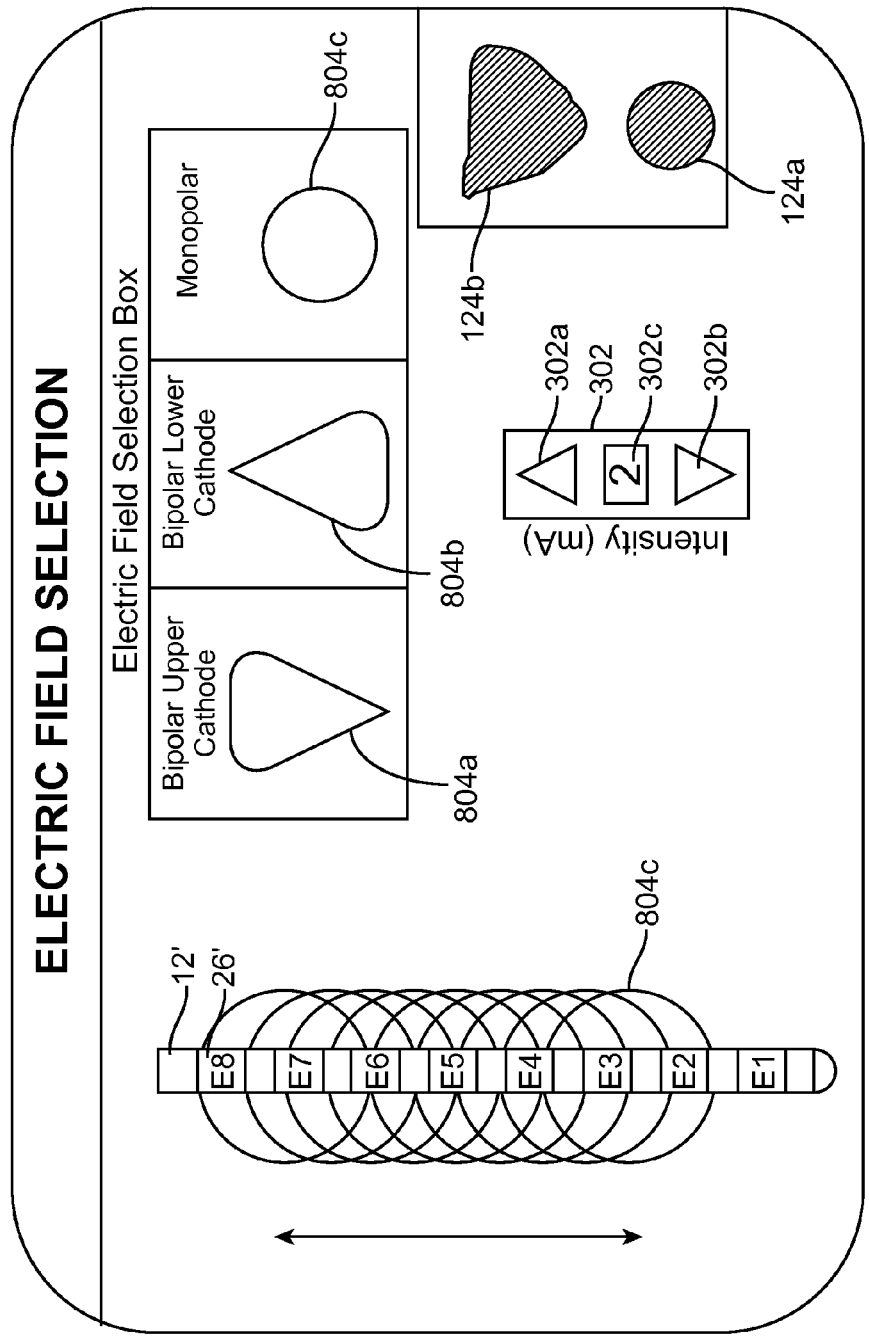
FIG. 27 is a plan view of the electric field selection screen of FIG. 25, particularly showing the movement of a selected electric field shape along a graphical representation of the neurostimulation lead.
Figure 28:
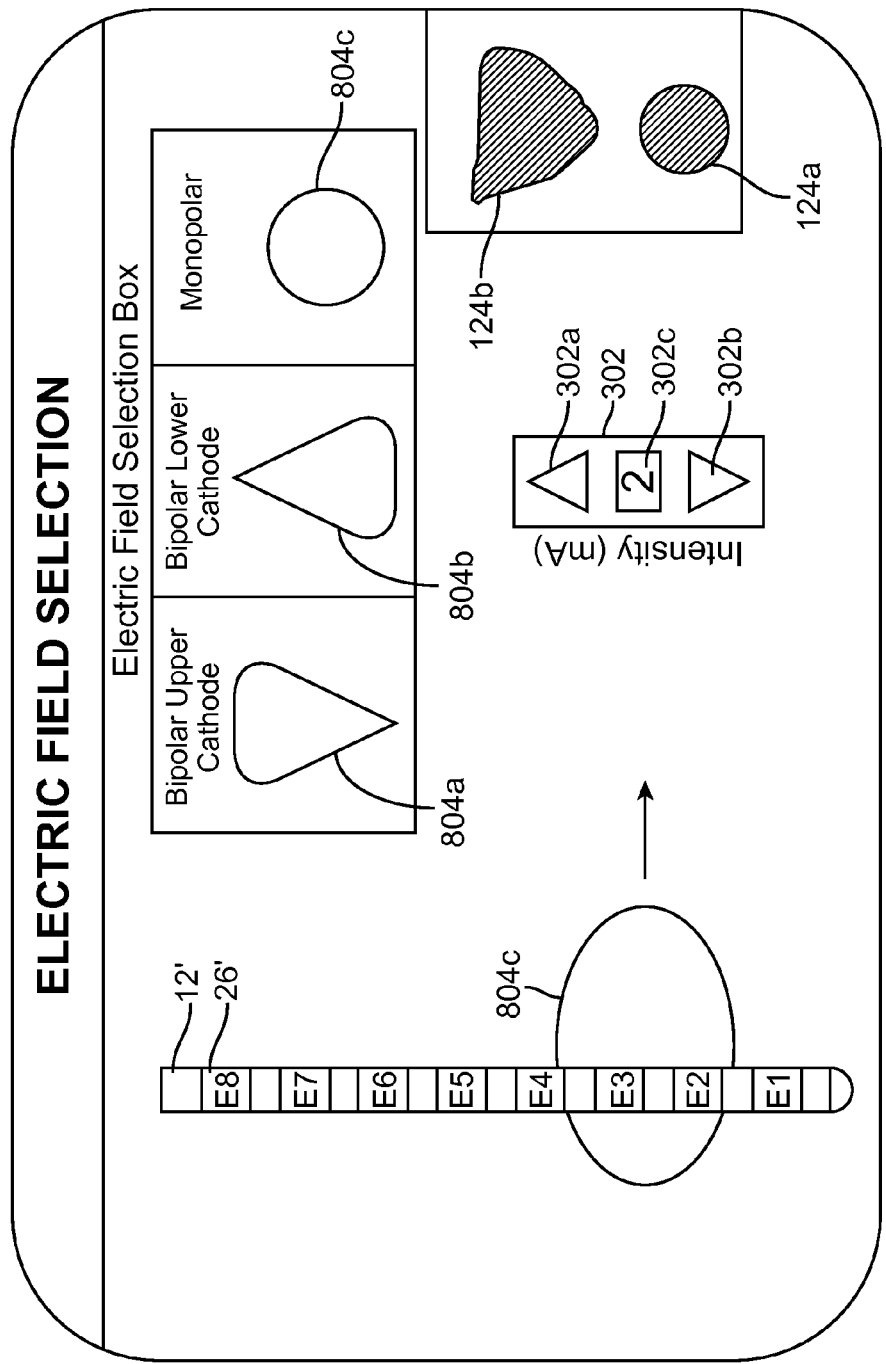
FIG. 28 is a plan view of the electric field selection screen of FIG. 25, particularly illustrating the modification of a user-selected electric field shape.

In the preferred embodiment, the CP 18 determines the combination of electrodes that best emulates the selected shape and defined location of the electric field. In the illustrated embodiment, the electrode combination that is determined to best match the electric field is a fractionalized electrode combination. The CP 18 may dynamically determine the fractionalized electrode combination as the graphical shape 804 is moved relative to the graphical electrode representation 26'. For example, as the graphical shape 804a is moved along the length of the graphical electrode representation 26' (as shown by arrows), as shown in FIG. 27, the CP 18 may compute the fractionalized electrode combination corresponding to each of the locations of the graphical shape 804a relative to the electrodes. In an optional embodiment, once the graphical shape 804 is dragged and dropped onto the graphical electrode representation 26', one side of the graphical shape 804 may be moved (e.g., in the direction of the arrow) in order to expand or contract the graphical shape 804 in one direction, as shown in FIG. 28. Furthermore, the size of the selected graphical shape 804 may be changed (either making it larger or smaller) by actuating the intensity level adjustment control 302 (i.e., increasing the intensity increases the size of the selected graphical shape 804, and decreasing the intensity decreases the size of the selected graphical shape 804).

The CP 18 may alternatively automatically determine the combination of electrodes that best emulates the selected shape and defined location of the electric field using any one of a variety of known techniques. For example, the CP 18 may theoretically overlay a grid of spatial observation points over the electric field, with each point assuming an electric field magnitude value. It can be assumed that the magnitude at the center of the electric field is highest, which exponentially tapers off towards the edges of the electric field.

Linearly independent constituent sources are then selected at the locations of electrodes E1-E8. Preferably, the constituent current sources are linearly independents. In the illustrated embodiment, bipoles are selected as constituent sources, because they are simple, and lend themselves well to conservation of current (i.e., if all constituent sources have conserved current (net zero), then any linear combination of them will also have conserved current). For example, a first constituent current source can be defined at the locations of electrodes E1 and E2 as −100% and +100%, respectively; a second constituent current source can be defined at the locations of electrodes E2 and E3 as −100% and +100%, respectively; a third constituent current source can be defined at the locations of electrodes E3 and E4 as −100% and +100%, respectively; and so on.

Once the constituent sources are selected, the CP 18 determines the relative strengths of the constituent current sources that, when combined, result in estimated electric field potential values at the spatial observation points that best matches the desired field potential values at the spatial observation points. In particular, the CP 18 models the constituent current sources (e.g., using analytical and/or numerical models) and estimates the field potential values per unit current (V/mA) generated by each of the constituent current sources at the spatial observation points, and generating an m×n transfer matrix from the estimated field potential values per unit current, with m equaling the number of spatial observation points and n equaling the number of constituent sources. The relative strengths of the constituent current sources are determined using an optimization function that includes the transfer matrix A and the desired field potential values. This technique is described in further detail in U.S. patent application Ser. No. 12/938,282, entitled "System and Method for Mapping Arbitrary Electric Fields to Pre-Existing Lead Electrodes," which is expressly incorporated herein by reference.

The CP 18 may instruct the IPG 14 to convey electrical stimulation energy to the fractionalized electrode combination determined to emulate the electric field, thereby creating one or more clinical effects. If the user selects different ones of the graphical shapes 804 and/or different locations for a selected graphical shape 804, the IPG 14 may instruct the IPG 14 to convey electrical stimulation energy for each of the fractionalized electrode combinations determined to emulate the different electrical fields corresponding to the different graphical shapes and/or different locations for the graphical shapes, thereby creating a clinical effect for each of the determined fractionalized electrode combinations. The user may enter a score for each of the fractionalized electrode combinations, in which case, the CP 18 may subsequently present the top-rated fractionalized electrode combinations to the user for therapy.

In another embodiment, the CP 18 may generate a plurality of different electric fields that best match a target tissue region (which may correspond to the target tissue region 324 generated in response to clinical information entered by the user or may be imported into the CP 18). The CP 18 can also determine the fractionalized electrode combinations that best emulate the different electric fields, e.g., in the manner described above. The CP 18 may present the best matching electric fields to the user (e.g., the top three matching electric fields), as shown in a program selection screen 900 shown in FIG. 29.

In particular, the program selection screen 900 may display three graphical shapes 902 corresponding to the shape of the there best matching electric fields, and a percentage coverage 904 for each electric field (i.e., the percentage of the area of the corresponding target tissue region covered by the respective electric field). The program selection screen 900 further includes selection buttons 906 that can be clicked by the user to prompt the CP 18 to instruct the IPG 14 to convey electrical stimulation energy in accordance with the fractionalized electrode combination corresponding to the selected electric field. The user may be prompted to incrementally increase the intensity of the conveyed electrical stimulation energy (e.g., via an intensity level adjustment control) until the therapy is optimum.

There may be instances where side-effects and therapy overlap. Hence, it may be useful to convey a constant amount of electrical stimulation energy, while varying the pulse amplitude and pulse width (i.e., inversely varying the pulse amplitude and pulse width, such that if the pulse amplitude is increased, the pulse width is decreased, and if the pulse amplitude is decreased, the pulse width is increased). For example, if the conveyed electrical stimulation energy has a pulse width of 60 μs and a pulse amplitude of 2 mA, the pulse width can be slowly decreased to 30 μs while the pulse amplitude is increased to slowly increased to 4 mA (stopping at various points to evaluate the therapy/side-effects). Similarly, the pulse width can be slowly increased to 120 μs from 60 μs while the pulse amplitude is decreased from 4 mA to 1 mA.

Once optimum therapy is achieved, the user may enter a score 908 and save the fractionalized electrode combination along with the adjusted intensity as a program. In the illustrated embodiment, this score 908 is a wellness that takes into account both therapy and side-effects. The different programs can be designated as either very conservative (e.g., minimal or moderate therapy with very little or no side-effects) that can be used during a period of time when maximum therapy is not needed (e.g., during sleep); very aggressive (e.g., maximum therapy with substantial side-effects) that can be used during a period of time when maximum therapy is desired (e.g., during performance of intricate physical tasks); or moderate (moderate therapy with little side-effects). The CP 18 may have a control for selecting the program based on how conservative or aggressive it is.

Although the foregoing techniques have been described as being implemented in the CP 18, it should be noted that this technique may be alternatively or additionally implemented in the RC 16. Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external programmer for use with a neurostimulator, comprising:
   output circuitry configured to communicate with the neurostimulator;
   control circuitry configured to instruct the neurostimulator via the output circuitry to convey electrical stimulation energy into tissue of a patient via different combinations of electrodes implanted within the patient, thereby creating one or more clinical effects for each of the different electrode combinations; and
   processing circuitry configured to determine an influence of each of the different electrode combinations on the one or more clinical effects, and generate a graphical indication of the one or more clinical effects based on the influence of different electrode combinations;
   wherein the control circuitry is further configured to
      instruct a display device to display an electrode selection control configured to allow user selection of the different electrode combinations, and
      instruct display of the graphical indication of the one or more clinical effects based upon electrical stimulation energy conveyed into the tissue of the patient via the neurostimulator adjacent a graphical rendering of the electrodes such that the user can view a data map that quantifies an extent to which each of the different electrode combinations influences the one or more clinical effects, and modify display of the graphical indication of the one or more clinical effects by at least one of spatially translating the graphical indication of the one or more clinical effects and changing a shape of the graphical indication relative to the graphical rendering of the electrodes based on the determined influence of the user selection of different electrode combinations.

2. The external programmer of claim 1, further comprising a user interface configured to allow a user to enter clinical information on the one or more clinical effects for the each different electrode combination, wherein the processing circuitry is configured to determine the influence of the each different electrode combination on the one or more clinical effects based on the clinical information entered by the user, wherein the data map is a bar map representing the extent to which each of the different electrode combinations influences the one or more clinical effects.

3. The external programmer of claim 1, further comprising monitoring circuitry configured to monitor the one or more clinical effects for the each different electrode combination, wherein the processing circuitry is configured to determine the influence of the each different electrode combination on the one or more clinical effects based on the monitored one or more clinical effects.

4. The external programmer of claim 1, wherein each of the electrode combinations has only one electrode.

5. The external programmer of claim 1, wherein at least one of the electrode combinations comprises a fractionalized electrode combination.

6. The external programmer of claim 1, wherein the one or more clinical effects comprises a therapeutic effect.

7. The external programmer of claim 1, wherein the one or more clinical effects comprises a side-effect.

8. The external programmer of claim 1,
wherein the control circuitry is further configured to instruct the neurostimulator via the output circuitry to incrementally increase an intensity level of the conveyed electrical stimulation energy for each of the different electrode combinations; and
wherein the processing circuitry is configured for determining the influence of the each different electrode combination on the one or more clinical effects for each intensity level.

9. The external programmer of claim 8, wherein the one or more clinical effects comprises one or more therapeutic effects, and the processing circuitry is configured to determine the influence of the each different electrode combination on the one or more therapeutic effects by determining a range of incremental intensity levels at which a metric of the one or more therapeutic effects occurs.

10. The external programmer of claim 9, wherein the one or more clinical effects further comprises one or more side-effects, and the processing circuitry is further configured to determine the influence of the each different electrode combination on the one or more side-effects by determining an incremental intensity level at which a metric of the one or more side-effects initially occurs.

11. The external programmer of claim 10, wherein the processing circuitry is further configured to determine the influence of the each different electrode combination on the one or more therapeutic effects by determining a highest intensity level at which the one or more therapeutic effect metrics occur prior to the initial occurrence of one or more side-effect metrics.

12. The external programmer of claim 11, wherein the graphical indication of the one or more clinical effects comprises a bar map having a plurality of bars, each of which indicates for the each different electrode combination the highest intensity level at which the one or more therapeutic effect metrics occur prior to the initial occurrence of the one or more side-effect metrics.

13. The external programmer of claim 12, wherein the therapeutic effect metric is a perception threshold of the one or more therapeutic effects, and the side-effect metric is one of a perception threshold of the one or more side-effects, an uncomfortable threshold of the one or more side-effects, and an intolerable threshold of the one or more side-effects.

14. The external programmer of claim 9, wherein the therapeutic effect metric is a relative level of the one or more therapeutic effects.

15. The external programmer of claim 14, wherein the one or more therapeutic effects comprises a plurality of therapeutic effects, and the relative level is a composite score as a function of individual scores of the therapeutic effects.

16. The external programmer of claim 14, wherein the graphical indication of the one or more clinical effects comprises a bar map for each of the electrode combinations, each bar map having a bar indicating the relative level of the one or more therapeutic effects at the each incremental intensity level.

17. The external programmer of claim 9, wherein the processing circuitry is configured to determine the influence of the each different electrode combination on the one or more clinical effects by determining electrode combinations that most influence the one or more therapeutic effects, and wherein the graphical indication of the one or more clinical effects comprises at least one target tissue region displayed adjacent the graphical rendering of the electrodes determined to most influence the one or more therapeutic effects.

18. The external programmer of claim 17, wherein the processing circuitry is further configured to determine the influence of the each different electrode combination on the one or more clinical effects by determining electrode combinations that most influence the side-effect, and wherein the graphical indication of the one or more clinical effects comprises at least one non-target tissue region displayed adjacent the electrode combinations in a graphical electrode representation determined to most influence the side-effect.

19. The external programmer of claim 17, wherein the processing circuitry is further configured to estimate one of an electric field or a region of tissue activation at a highest incremental intensity level at which the one or more therapeutic effects occurs for the each different electrode combination, wherein the at least one target tissue region is based on the estimated electric field or region of tissue activation.

20. The external programmer of claim 1, wherein the control circuitry is further configured to program the neurostimulator via the output circuitry based on the extent to which the each different electrode combination influences the one or more clinical effects.

21. The external programmer of claim 1, further comprising memory configured to store data indicating the determined influence of the each different electrode combination on the one or more clinical effects.

22. A method of treating a patient using the external programmer of claim 1, comprising:
conveying the electrical stimulation energy into tissue of the patient via the different combinations of electrodes implanted within the patient, thereby creating the one or more clinical effects for each of the different electrode combinations;

determining the influence of each different electrode combinations on the one or more clinical effects;

generating the graphical indication of the one or more clinical effects based on the determined electrode combination influences;

displaying the graphical rendering of the electrodes; and displaying the graphical indication of the one or more clinical effects adjacent the graphical electrode representation, such that the user can determine the extent to which each of the different electrode combinations influences the one or more clinical effects.

23. The method of claim 22, wherein each of the electrode combinations has only one electrode.

24. The method of claim 22, wherein at least one of the electrode combinations comprises a fractionalized electrode combination.

25. The method of claim 22, wherein the one or more clinical effects comprises a therapeutic effect.

26. The method of claim 22, wherein the one or more clinical effects comprises a side-effect.

27. The method of claim 22, further comprising incrementally increasing an intensity level of the conveyed electrical stimulation energy for each of the different electrode combinations, wherein the influence of the each different electrode combination on the one or more clinical effects is determined for each of the incremental intensity levels.

28. The method of claim 27, wherein the one or more clinical effects comprises one or more therapeutic effects, and the influence of the each different electrode combination on the one or more therapeutic effects is determined by determining the range of incremental intensity levels at which a metric of the one or more therapeutic effects occurs.

29. The method of claim 28, wherein the one or more clinical effects further comprises one or more side-effects, and the influence of the each different electrode combination on the one or more side-effects is determined by determining the incremental intensity level at which a metric of the one or more side-effects initially occurs.

30. The method of claim 29, wherein the influence of the each different electrode combination on the one or more therapeutic effects is further determined by determining the highest intensity level at which the one or more therapeutic effect metrics occur prior to the initial occurrence of the one or more side-effect metrics.

31. The method of claim 30, wherein the graphical indication of the one or more clinical effects comprises a bar map having a plurality of bars, each of which indicates for the each different electrode combination the highest intensity level at which the one or more therapeutic effect metrics occur prior to the initial occurrence of the one or more side-effect metrics.

32. The method of claim 31, wherein the therapeutic effect metric is a perception threshold of the one or more therapeutic effects, and the side-effect metric is one of a perception threshold of the one or more side-effects, an uncomfortable threshold of the one or more side-effects, and an intolerable threshold of the one or more side-effects.

33. The method of claim 28, wherein the therapeutic effect metric is a relative level of the one or more therapeutic effects.

34. The method of claim 33, wherein the one or more therapeutic effects comprises a plurality of therapeutic effects, and the relative level is a composite score as a function of individual scores of the therapeutic effects.

35. The method of claim 33, wherein the graphical indication of the one or more clinical effects comprises a bar map for each of the electrode combinations, each bar map having a bar indicating the relative level of the one or more therapeutic effects at the each incremental intensity level.

36. The method of claim 28, wherein the influence of the each different electrode combination on the one or more clinical effects is determined by determining the electrode combinations that most influence the one or more therapeutic effects, and wherein the graphical indication of the one or more clinical effects comprises at least one target tissue region displayed adjacent the electrode combinations in the graphical electrode representation determined to most influence the one or more therapeutic effects.

37. The method of claim 36, wherein the influence of the each different electrode combination on the one or more clinical effects is determined by determining the electrode combinations that most influence the side-effect, and wherein the graphical indication of the one or more clinical effects comprises at least one non-target tissue region displayed adjacent the electrode combinations in the graphical electrode representation determined to most influence the side-effect.

38. The method of claim 36, further comprising estimating one of an electric field or a region of tissue activation at the highest incremental intensity level at which the one or more therapeutic effects occurs for the each different electrode combination, wherein the target tissue region is based on the estimated electric field or region of tissue activation.

39. The method of claim 22, wherein the electrical stimulation energy is conveyed from a neurostimulator, the method further comprising programming the neurostimulator based on the determined extent to which the each different electrode combination influences the one or more clinical effects.

40. The method of claim 22, further comprising recording data in computer memory indicating the determined influence of the each different electrode combination on the one or more clinical effects.

41. The method of claim 22, wherein the tissue is brain tissue.

* * * * *